US010973879B2

(12) United States Patent
Vitti et al.

(10) Patent No.: US 10,973,879 B2
(45) Date of Patent: Apr. 13, 2021

(54) USE OF A VEGF ANTAGONIST TO TREAT ANGIOGENIC EYE DISORDERS

(71) Applicant: REGENERON PHARMACEUTICALS, INC., Tarrytown, NY (US)

(72) Inventors: Robert L. Vitti, Old Tappan, NJ (US); Alyson J. Berliner, New York, NY (US); Karen Chu, White Plains, NY (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 169 days.

(21) Appl. No.: 16/204,262

(22) Filed: Nov. 29, 2018

(65) Prior Publication Data
US 2019/0290725 A1    Sep. 26, 2019

Related U.S. Application Data

(60) Provisional application No. 62/644,425, filed on Mar. 17, 2018, provisional application No. 62/748,782, (Continued)

(51) Int. Cl.
*A61K 38/18* (2006.01)
*A61K 38/17* (2006.01)
(Continued)

(52) U.S. Cl.
CPC .......... *A61K 38/179* (2013.01); *A61K 9/0019* (2013.01); *A61K 47/65* (2017.08); *A61P 27/02* (2018.01)

(58) Field of Classification Search
CPC ............................ A61K 38/179; A61K 9/0019
See application file for complete search history.

(56) References Cited

U.S. PATENT DOCUMENTS 7,070,959 B1    7/2006  Papdopoulos et al.
7,303,747 B2 *  12/2007 Wiegand ................ C07K 14/71
                                                             424/134.1
(Continued)

FOREIGN PATENT DOCUMENTS

WO   WO 2000/075319   12/2000
WO   WO2002/060489    8/2002
(Continued)

OTHER PUBLICATIONS

ClinicalTrials.gov, Vascular Endothelial Growth Factor (VEGF) Trap-Eye: Investigation of Efficacy and Safety in Wet Age-Related Macular Degeneration (AMD) (VIEW 2), Retrieved online <URL:https://clinicaltrials.gov/ct2/show/study/NCT00637377>, on Jul. 13, 2020, Dec. 12, 2014.*

(Continued)

*Primary Examiner* — Claire Kaufman
(74) *Attorney, Agent, or Firm* — Thomas Triolo; Karl Bozicevic

(57) ABSTRACT

The present invention provides methods for treating or preventing diabetic retinopathy, e.g., nonproliferative diabetic retinopathy, by sequentially administering multiple doses of a VEGF antagonist to a patient. The methods of the present invention include the administration of a 2 mg aflibercept by intravitreal injection q8 weeks after three or five initial monthly doses (2q8) or 2 mg q16 weeks after three initial monthly doses and one 8-week interval (2q16). Moreover, the present invention provides methods for reversing or halting the progression NPDR to PDR (e.g., such that the DRSS is reduced by 2 or 3 levels) or preventing the occurrence or reoccurrence of a vision threatening complication by administering aflibercept according to the dosing regimens set forth herein.

21 Claims, 32 Drawing Sheets

Specification includes a Sequence Listing.

Related U.S. Application Data filed on Oct. 22, 2018, provisional application No. 62/593,033, filed on Nov. 30, 2017.

(51) Int. Cl.
- *A61K 47/65* (2017.01)
- *A61P 27/02* (2006.01)
- *A61K 9/00* (2006.01)

(56) References Cited

U.S. PATENT DOCUMENTS

| | | |
|---|---|---|
| 9,254,338 B2 | 2/2016 | Yancopoulos |
| 9,669,069 B2 | 6/2017 | Yancopoulos |
| 10,130,681 B2 | 11/2018 | Yancopoulos |
| 2005/0260203 A1 | 11/2005 | Wiegand |
| 2018/0339018 A1 | 11/2018 | Yancopoulos |
| 2019/0046609 A1 | 2/2019 | Yancopoulos |
| 2019/0247463 A1 | 8/2019 | Yancopoulos |
| 2019/0343918 A1 | 11/2019 | Graham et al. |

FOREIGN PATENT DOCUMENTS

| | | |
|---|---|---|
| WO | WO 2005/000895 | 1/2005 |
| WO | WO 2012/097019 | 7/2012 |
| WO | WO 2014/203183 A1 | 12/2014 |
| WO | WO 2012/097019 A1 | 7/2017 |

OTHER PUBLICATIONS

De Oliveira Dias et al., Fusion proteins for treatment of retinal diseases: aflibercept, ziv-aflibercept, and conbercept, Int. J. Retina Vitreous, 2:3, pp. 1-9, 2016.*
Dadgostar et al.,The evolving role of vascular endothelial growth factor inhibitors in the Eye, 22:761-767, 2008.*
Avitabile et al., Aflibercept in the treatment of diabetic macular edema: a review and consensus paper, Eur. J. Ophthalmol. 27(6): 627-639, published online Oct. 2017.*
Cui et al., Comparison of effectiveness and safety between conbercept and ranibizumab for treatment of neovascular age-related macular degeneration. A retrospective case-controlled non-inferiority multiple center study, Eye, 32:391-399, published online Sep. 2017.*
Do et al., The DA VINCI study: Phase 2 primary results of VEGF Trap-Eye in patients with diabetic macular edema, Ophthalmol. 118:1819-1825, 2011.*
Brown, Poster: Intravitreal Aflibercept Injection (IAI) for Moderately Severe to Severe Nonproliferative Diabetic Retinopathy (NPDR): The Phase 3 PANORAMA Study—Association for Research in Vision and Ophthalmology (ARVO) Annual Meeting (Apr. 29-May 3, 2018—Honolulu, HI).
Brown, Abstract PO213: Intravitreal Aflibercept Injection for Moderately Severe to Severe Nonproliferative Diabetic Retinopathy, Annual 2018 Meeting—American Academy of Opthamology (AAO) (Oct. 28, 2018).
Brown, Abstract: Diabetic Retinopathy (NPDR): The Phase 3 PANORAMA Study, 2018 Annual Meeting—(Association for Research in Vision and Ophthalmology (ARVO) (Apr. 29-May 3, 2018—Honolulu, HI).
Association for Research in Vision and Ophthalmology (ARVO) 2018 Program Summary Book, 2018 Annual Meeting (Apr. 29-May 3, 2018—Honolulu, HI), pp. 1-481.
Regeneron announces two-year results from Phase 3 PANORAMA evaluating EYLEA, Theflyonthewall.com (Feb. 9, 2020).
Event Brief of Q1 2016 Regeneron Pharmaceuticals Inc Earnings Call—Final, FD (Fair Disclosure) Wire (May 5, 2016).
Event Brief of Q1 2017 Regeneron Pharmaceuticals Inc Earnings Call—Final, FD (Fair Disclosure) Wire (May 4, 2017).
Event Brief of Q4 2016 Regeneron Pharmaceuticals Inc Earnings Call—Final, FD (Fair Disclosure) Wire (Feb. 9, 2017).
EYLEA® (aflibercept) Injection Demonstrates Positive Topline Results in Phase 3 Non-Proliferative Diabetic Retinopathy Trial; Expect U.S. regulatory submission for diabetic retinopathy later this year, PE Newswire (Mar. 19, 2018).
Q1 2016 Regeneron Pharmaceuticals Inc Earnings Call—Final, FD (Fair Disclosure) Wire (May 5, 2016).
Q1 2017 Regeneron Pharmaceuticals Inc Earnings Call—Final, FD (Fair Disclosure) Wire (May 4, 2017).
Q1 2019 Regeneron Pharmaceuticals Inc Earnings Call—Final, FD (Fair Disclosure) Wire (May 7, 2019).
Q2 2019 Regeneron Pharmaceuticals Inc Earnings Call—Final, FD (Fair Disclosure) Wire (Aug. 6, 2019).
Q4 2015 Regeneron Pharmaceuticals Inc Earnings Call—Final, FD (Fair Disclosure) Wire (Feb. 9, 2016).
Q4 2016 Regeneron Pharmaceuticals Inc Earnings Call—Final, FD (Fair Disclosure) Wire (Feb. 9, 2017).
Q4 2019 Regeneron Pharmaceuticals Inc Earnings Call—Final, FD (Fair Disclosure) Wire (Feb. 6, 2020).
Regeneron Announces Positive Two Year EYLEA Results in Patients with Diabetic Retinopathy at Angiogenesis, Exudation, and Degeneration 2020 Meeting, Newstex Blogs, Benzinga (Feb. 8, 2020).
Regeneron Pharmaceuticals (REGN) Earnings Report: Q1 2016 Conference Call Transcript, TheStreet.com (May 6, 2016).
Regeneron Pharmaceuticals (REGN) Earnings Report: Q4 2015 Conference Call Transcript, TheStreet.com (Feb. 9, 2016).
Regeneron Pharmaceuticals Inc Annual Shareholders Meeting—Final, FD (Fair Disclosure) Wire (Jun. 14, 2019).
Regeneron Pharmaceuticals Inc at Barclays Biopharmaceuticals CEO/CFO Conference Call Series—Final, FD (Fair Disclosure) Wire (May 17, 2019).
Regeneron Pharmaceuticals, Inc.—EYLEA Injection Improves Diabetic Retinopathy and Reduces Vision-Threatening Complications in Phase 3 Trial, ENP Newswire (Oct. 26, 2018).
Regeneron Pharmaceuticals, Inc.—FDA Approves EYLEA Injection for Diabetic Retinopathy, ENP Newswire (May 14, 2019).
Regeneron Reports First Quarter 2020 Financial and Operating Results, PE Newswire (May 5, 2020).
Regeneron Reports Fourth Quarter and Full Year 2017 Financial and Operating Results, Plus Company Updates (PCU) (Feb. 13, 2018).
Regeneron Reports Third Quarter 2018 Financial and Operating Results, PR Newswire (Nov. 6, 2018).
Regeneron's Eylea Soars, But Praluent Is Slow Out of the Gate, The Pink Sheet Daily (Feb. 9, 2016).
Event Brief of Q4 2018 Regeneron Pharmaceuticals Inc Earnings Call—Final, FD (Fair Disclosure) Wire (Feb. 6, 2019).
EYLEA® (aflibercept) Injection Improves Diabetic Retinopathy and Reduces Vision-Threatening Complications in Phase 3 Trial, Global English (Middle East and North Africa Financial Network) (Oct. 25, 2018).
FDA to Review EYLEA (aflibercept) Injection for the Treatment of Diabetic Retinopathy, PR Newswire (Sep. 13, 2018).
One-Year Results from Positive Phase 3 EYLEA Trial in Diabetic Retinopathy Presented at Angiogenesis Symposium, Pharma & Healthcare Monitor Worldwide (Feb. 11, 2019).
One-Year Results from Positive Phase 3 EYLEA Trial in Diabetic Retinopathy Presented at Angiogenesis Symposium, Global English (Middle East and North Africa Financial Network) (Feb. 9, 2019).
Q1 2018 Regeneron Pharmaceuticals Inc Earnings Call—Final, FD (Fair Disclosure) Wire (May 3, 2018).
Q2 2017 Regeneron Pharmaceuticals Inc Earnings Call—Final, FD (Fair Disclosure) Wire (Aug. 3, 2017).
Q2 2018 Regeneron Pharmaceuticals Inc Earnings Call—Final, FD (Fair Disclosure) Wire (Aug. 2, 2018).
Q3 2017 Regeneron Pharmaceuticals Inc Earnings Call—Final, FD (Fair Disclosure) Wire (Nov. 8, 2017).
Q3 2018 Regeneron Pharmaceuticals Inc Earnings Call—Final, FD (Fair Disclosure) Wire (Nov. 6, 2018).
Q4 2018 Regeneron Pharmaceuticals Inc Earnings Call—Final, FD (Fair Disclosure) Wire (Feb. 6, 2019).
Regeneron (REGN) to Report Q3 Earnings: Is a Beat in Store?, Zacks Investment Research (Nov. 1, 2018).
Regeneron announces phase 3 PANORAMA trial evaluating Eylea in moderately severe to severe NPDR met its 24-week primary . . . , PharmaBiz (Mar. 20, 2018).

(56) References Cited

OTHER PUBLICATIONS

Regeneron Pharmaceuticals Inc at Bank of America Merrill Lynch Health Care Conference—Final, FD (Fair Disclosure) Wire (Sep. 13, 2017).
Regeneron Pharmaceuticals Inc at J.P. Morgan 2019 Spring Biotech Conference Call—Final, FD(Fair Disclosure) Wire (Mar. 15, 2019).
Regeneron Pharmaceuticals Inc at JPMorgan Global Healthcare Conference—Final, FD (Fair Disclosure) Wire (Jan. 7, 2019).
Regeneron Reports First Quarter 2018 Financial and Operating Results, PR Newswire (May 3, 2018).
Regeneron Reports Fourth Quarter and Full Year 2017 Financial and Operating Results, PR Newswire (Feb. 8, 2018).
Regeneron Reports Fourth Quarter and Full Year 2018 Financial and Operating Results, PR Newswire (Feb. 6, 2019).
Regeneron Reports Positive Results From Phase 3 PANORAMA Trial With EYLEA, CE Noticias Financieras English (Mar. 19, 2018).
Regeneron Reports Second Quarter 2018 Financial and Operating Results, PR Newswire (Aug. 2, 2018).
Regeneron Reports Third Quarter 2017 Financial and Operating Results, PR Newswire (Nov. 8, 2017).
United States: EYLEA (aflibercept) Injection Demonstrates Positive Topline Results in Phase 3 Non-Proliferative Diabetic Retinopathy Trial, Thai News Service (Apr. 13, 2018).
Will Regeneron Pharma (REGN) Disappoint in Q3 Earnings?, Zacks Investment Research (Nov. 3, 2017).
Regeneron Reports Third Quarter 2017 Financial and Operating Results (Nov. 8, 2017).
Intravitreal Aflibercept for Moderately Severe to Severe Non-Proliferative Diabetic Retinopathy (NPDR) the Phase 3 PANORAMA Study, slide deck presented by Charles Wycoff, American Society of Retinal Specialists, 2018 Annual Meeting (Jun. 24, 2018).
Intravitreal Aflibercept for Moderately Severe to Severe Non-Proliferative Diabetic Retinopathy (NPDR) The Phase 3 PANORAMA Study, slide deck presented by Charles Wycoff, Angiogenesis, Exudation, and Degeneration meeting (Feb. 9, 2019) & Association for Research in Vision and Ophthalmology (ARVO) Annual Meeting (Apr. 29, 2019).
A Phase 3, Double Masked, Randomized Study of the Efficacy and Safety of Aflibercept in Patients With Moderately Severe to Severe NPDR—Week 100 Results, slide deck presented by Charles Wycoff, Angiogenesis, Exudation, and Degeneration meeting (Feb. 8, 2020).
clinicaltrials.gov PANORAMA posting NCT02718326 (Mar. 23, 2016).
clinicaltrials.gov PANORAMA posting NCT02718326 (May 2, 2016).
clinicaltrials.gov PANORAMA posting NCT02718326 (Oct. 21, 2016).
clinicaltrials.gov PANORAMA posting NCT02718326 (Nov. 29, 2016).
clinicaltrials.gov PANORAMA posting NCT02718326 (May 10, 2017).
clinicaltrials.gov PANORAMA posting NCT02718326 (Jul. 6, 2017).
clinicaltrials.gov PANORAMA posting NCT02718326 (Aug. 24, 2017).
clinicaltrials.gov PANORAMA posting NCT02718326 (May 18, 2018).
clinicaltrials.gov PANORAMA posting NCT02718326 (Nov. 19, 2019).
Regeneron 10-K (Feb. 9, 2017).
Regeneron Form 10-K (Dec. 31, 2016).
Regeneron Form 10-K (Dec. 31, 2017).
Regeneron Form 10-K (Dec. 31, 2018).
Regeneron Form 10-Q (Jun. 30, 2018).
Regeneron Form 10-Q (Jun. 30, 2016).
Regeneron Form 10-Q (Jun. 30, 2017).
Regeneron Form 10-Q (Mar. 31, 2017).
Regeneron Form 10-Q (Mar. 31, 2018).
Regeneron Form 10-Q (Sep. 30, 2016).
Regeneron Form 10-Q (Sep. 30, 2017).
Regeneron Form 10-Q (Sep. 30, 2018).
Regeneron Reports First Quarter 2020 Financial and Operating Results, PR Newswire (May 5, 2020).
Regeneron 2017 Annual Report.
Regeneron 2018 Annual Report.
Regeneron 2019 Annual Report.
Regeneron 2016 Annual Report.
Regeneron 2015 Annual Report.
Eylea Prescribing Information (May 2016).
Eylea Prescribing Information (May 2017).
Eylea Prescribing Information (Nov. 2011).
Anonymous, "Highlights of Prescribing Information" (Dec. 1, 2016) Retrieved from the Internet: URL: https://web.archive.org/web.20161206164049if_/https://www.regeneron.com/sites/default/files/EYLEA_FPI.pdf [retrieved on Mar. 7, 2019] the whole document, p. 1 right column, paragraph 1 2.5; p. 2 left hand column.
Anonymous, "Archive History for NCT02718326", (Aug. 24, 2017) Retrieved from the Internet: URL: https://clinicaltrials.gov.ct2/history/NCT02718326?V_7=View#StudyPageTop [retrieved on Mar. 7, 2019] the whole document.
Stewart Michael W., "Aflibercept (VEGF-TRAP): The Next Anti-VEGF Drug", Inflammation & Allergy Drug Tar, Bentham Science Publishers, NL. vol. 10, No. 6, (Dec. 1, 2011_ pp. 497-508.
Brown et al., Poster: Intravitreal Aflibercept Injection (IAI) for Moderately Severe to Severe Nonproliferative Diabetic Retinopathy (NPDR): The Phase 3 PANORAMA Study, Assoc. or Res. in Vision and Ophthalmology (ARVO), 2018 Annual Meeting, Honolulu, HI (Apr. 29, 2018-May 3, 2018).
Brown, Abstract: Intravitreal Aflibercept Injection (IAI) for Moderately Severe to Severe Nonproliferative Diabetic Retinopathy (NPDR) (No. 30055820), American Acad. of Opthamol.(AAO), 2018 Annual Meeting, Chicago (Oct. 27-30, 2018).
Wykoff, Abstract: Intravitreal Aflibercept Injection (IAI) for Moderately Severe to Severe Nonproliferative Diabetic Retinopathy (NPDR): The Phase 3 PANORAMA Study, American Society of Retina Specialists (ASRS), 2018 Annual Meeting, Vancouver, BC (Jul. 20-24, 2018).
Heier et al, Abstract: Intravitreal Aflibercept Injection for Moderately Severe to Severe Nonproliferative Diabetic Retinopathy: The Phase 3 PANORAMA Study, The Retina Society, 2018 Annual Meeting, San Francisco, CA (Sep. 12-15, 2018).
Brown, Poster: Intravitreal Aflibercept Injection for Moderately Severe to Severe Nonproliferative Diabetic Retinopathy, American Acad. Of Opthamol.(AAO), 2018 Annual Meeting, Chicago (Oct. 27-30, 2018).
Higgins, Abstract: The Phase 3 PANORAMA Study of Intravitreal Aflibercept for Moderately Severe to Severe Non-Proliferative Diabetic Retinopathy, American Acad. of Opthamol.(AAO), 2018 Annual Meeting, Chicago (Oct. 27-30, 2018).
Lim, Abstract: Intravitreal Aflibercept Injection for Nonproliferative Diabetic Retinopathy: Year 2 Results from the PANORAMA Study, Assoc. for Res. un Vision and Ophthalmology (ARVO), 2018 Annual Meeting, Honolulu, HI (Apr. 29, 2018-May 3, 2018).
Brown, Abstract: Intravitreal Aflibercept Injection (IAI) for Moderately Severe to Severe Nonproliferative Diabetic Retinopathy (NPDR): The Phase 3 PANORAMA Study, Assoc. for Res. in Vision and Ophthalmology (ARVO), 2018 Annual Meeting, Honolulu, HI (Apr. 29, 2018-May 3, 2018).
Heier, Presentation: Intravitreal Aflibercept Injection for Moderately Severe to Severe Nonproliferative Diabetic Retinopathy: The Phase 3 PANORAMA Study, Retina Society Annual Meeting (2018).
Higgins, Presentation: The Phase 3 PANORAMA Study of Intravitreal Aflibercept for Moderately Severe to Severe Non-Proliferative Diabetic Retinopathy, American Acad. of Opthamol.(AAO), 2018.
Wykoff, Presentation: Intravitreal Aflibercept for Moderately Severe to Severe Non-Proliferative Diabetic Retinopathy (NPDR) The Phase 3 PANORAMA Study, The American Society of Retina Specialists, Jul. 24, 2018.
Clark, Abstract: Treatment of Moderately Severe to Severe Nonproliferative Diabetic Retinopathy with Intravitreal Aflibercept Injection, American Acad. of Opthamol.(AAO), 2018.

(56) References Cited

OTHER PUBLICATIONS

Brown, Abstract: Treatment of Moderately Severe to Severe Nonproliferative Diabetic Retinopathy with Intravitreal Aflibercept Injection: Results from the Phase 3 PANORAMA Study, 2019 Macula Society Meeting; Bonita Springs, FL (2018).

* cited by examiner

PANORAMA Dosing Schedule

| Week: | BL | 4 | 8 | 12 | 16 | 20 | 24 | 28 | 32 | 36 | 40 | 44 | 48 | 52 | 56 | ...100 |
|---|---|---|---|---|---|---|---|---|---|---|---|---|---|---|---|---|
| SHAM* | O | O | O | O | O | O | O | O | O | O | O | O | O | O | O | ... |
| Group 1* | X | X | X | O | X | O | O | O | X | O | O | X | X | X | O | ... |
| Group 2* | X | X | X | X | X | X | X | X | X | X | X | X | X | + | + | ... |

Only 1 dose difference between Group 1 and Group 2 through week 24

+Group 2 (Q8) group continues PRN through Week 100 based on DRSS level

*Patients progressing to PDR/ASNV or CI-DME were eligible for rescue treatment (IAI or laser) at the discretion of the investigator. Data for patients receiving rescue treatment was censored from the time of rescue.

X=active injection, O=sham injection

FIG. 4

Disposition and Baseline Demographics

| | Sham | Group 1 | Group 2 | All IAI | Total |
|---|---|---|---|---|---|
| Number of Patients who Completed at Week 24 | 119 (89.5%) | 129 (95.6%) | 132 (98.5%) | 261 (97.0%) | 380 (94.5%) |
| N (FAS/SAF) | 133 | 135 | 134 | 269 | 402 |
| Age (years (SD)) | 55.8 (10.31) | 55.4 (11.13) | 55.8 (10.19) | 55.6 (10.66) | 55.7 (10.53) |
| Women # (%) | 64 (48.1%) | 60 (44.4%) | 53 (39.6%) | 113 (42.0%) | 177 (44.0%) |
| Race # (%) | | | | | |
| White | 107 (80.5%) | 99 (73.3%) | 104 (77.6%) | 203 (75.5%) | 310 (77.1%) |
| Black or African American | 13 (9.8%) | 16 (11.9%) | 12 (9.0%) | 28 (10.4%) | 41 (10.2%) |
| Asian | 4 (3.0%) | 12 (8.9%) | 7 (5.2%) | 19 (7.1%) | 23 (5.7%) |
| Other | 9 (6.8%) | 8 (5.9%) | 11 (8.2%) | 19 (7.1%) | 28 (7.0%) |
| Hemoglobin A1C (%) | 8.5 (1.54) | 8.6 (1.69) | 8.4 (1.64) | 8.5 (1.66) | 8.5 (1.62) |
| Duration of Diabetes (years (SD)) | 15.5 (9.34) | 13.7 (8.61) | 14.0 (9.69) | 13.8 (9.15) | 14.4 (9.24) |
| Diabetes Type 2 | 123 (92.5%) | 121 (89.6%) | 124 (92.5%) | 245 (91.1%) | 368 (91.5%) |

Group 1: 3 monthly doses followed by 1 q8 intervals, Group 2: 5 monthly doses

FIG. 5

Baseline Disease Characteristics

| | Sham | Group 1 | Group 2 | All IAI | Total |
|---|---|---|---|---|---|
| N (FAS/SAF) | 133 | 135 | 134 | 269 | 402 |
| ETDRS BCVA (letters) Mean (SD) Snellen Equivalent | 82.7 (6.03) 20/25 | 82.2 (6.63) 20/25 | 82.3 (5.15) 20/25 | 82.3 (5.93) 20/25 | 82.4 (5.96) 20/25 |
| CRT (microns) Mean (SD) | 249.4 (38.41) | 246.0 (34.34) | 246.8 (31.59) | 246.4 (32.94) | 247.4 (34.82) |
| Diabetic Retinopathy Severity Score (DRSS) | | | | | |
| Level 47 | 99 (74.4%) | 102 (75.6%) | 101 (75.4%) | 203 (75.5%) | 302 (75.1%) |
| Level 53 | 34 (25.6%) | 33 (24.4%) | 33 (24.6%) | 66 (24.5%) | 100 (24.9%) |

Group 1: 3 monthly doses followed by 1 q8 intervals, Group 2: 5 monthly doses

FIG. 6

Ocular TEAEs in Study Eye through Week 24 (≥3%)

| | — Sham | - - - All IAI |
|---|---|---|
| N (FAS/SAF) | 133 | 269 |
| Number of Patients ≥ 1 AE, n (%) | 44 (33.1%) | 77 (28.6%) |
| Eye disorders | 42 (31.6%) | 76 (28.3%) |
| Conjunctival haemorrhage | 4 (3.0%) | 32 (11.9%) |
| Vitreous floaters | 1 (0.8%) | 14 (5.2%) |
| Diabetic retinal oedema | 18 (13.5%) | 11 (4.1%) |
| Eye pain | 2 (1.5%) | 11 (4.1%) |
| Diabetic retinopathy | 4 (3.0%) | 1 (0.4%) |

FIG. 13

Ocular Serious TEAEs in Study Eye through Week 24

| | — Sham | --- All IAI |
|---|---|---|
| N (FAS/SAF) | 133 | 269 |
| Number of Patients with ≥ 1 AE, n (%) | 1 (0.8%) | 0 |
| Iris neovascularisation | 1 (0.8%) | 0 |

FIG. 14

Ocular Inflammation in Study Eye through Week 24

| | — Sham | --- All IAI |
|---|---|---|
| N (FAS/SAF) | 133 | 269 |
| # of injection | 0 | 1182 |
| Vitreal cells | 0 | 1 (0.4%) (0.08% per injection) |

FIG. 15

APTC Events through Week 24

| | — Sham | --- All IAI |
|---|---|---|
| N (FAS/SAF) | 133 | 269 |
| Number of Patients with ≥ 1 AE, n (%) | 2 (1.5%) | 1 (0.4%) |
| Non Fatal Stroke | 0 | 1 (0.4%) |
| Cerebrovascular accident | 0 | 1 (0.4%) |
| Vascular Death | 2 (1.5%) | 0 |
| Cardiac arrest | 1 (0.8%) | 0 |
| Myocardial infarction | 1 (0.8%) | 0 |

FIG. 16

Deaths through Week 24

| Treatment Group | Patient Age /Sex /Race | Days from First Treatment to Death | Days from Last Treatment to Death | AE Preferred Term with Fatal Outcome | Rescue/ FE Treatment |
|---|---|---|---|---|---|
| Sham | 43/F/W | 52 | 23 | Acute respiratory failure Pulmonary hypertension | No rescue/ No FE treatment |
| Sham | 65/M/W | 73 | 13 | Cardiac arrest | No rescue/ No FE treatment |
| Sham | 73/M/W | 86 | 4 | Myocardial infarction | No rescue/ 2 FE treatments |

FIG. 17

International Clinical Diabetic Retinopathy Disease
Severity Scale Detailed Table

| LEVEL | SEVERITY | |
|---|---|---|
| 10 | DR absent | DRSS grading scale was derived from the ETDRS and is used to grade severity of DR and describe the change in severity over time. |
| 20 | Microaneurysms only | |
| 35 | Mild NPDR | |
| 43 | Moderate NPDR | |
| 47 | Moderately severe NPDR | |
| 53 | Severe NPDR | |
| 61 | Mild PDR | |
| 65 | Moderate PDR | |
| 71 | High Risk PDR | |
| 75 | High Risk PDR | |
| 81 | Advanced PDR, fundus partially obscured, center of macula attached | |
| 85 | Advanced PDR, posterior fundus obscured or center of macula detached | |
| 90 | Cannot grade, even sufficiently for level 81 or 85 | |

ETDRS Group, #12 1991

FIG. 18

Ocular TEAEs in Study Eye through Week 52 (≥3%)

| | — Sham | ---- 2q16 | — 2q8 |
|---|---|---|---|
| N (FAS/SAF) | 133 | 135 | 134 |
| Number of Patients ≥ 1 AE, n (%) | 67 (50.4%) | 58 (43.0%) | 60 (44.8%) |
| Eye disorders | 64 (48.1%) | 57 (42.2%) | 59 (44.0%) |
| Conjunctival haemorrhage | 7 (5.3%) | 16 (11.9%) | 23 (17.2%) |
| Diabetic retinal oedema | 32 (24.1%) | 8 (5.9%) | 12 (9.0%) |
| Vitreous floaters | 3 (2.3%) | 6 (4.4%) | 12 (9.0%) |
| Eye pain | 4 (3.0%) | 10 (7.4%) | 5 (3.7%) |
| Retinal exudates | 5 (3.8%) | 5 (3.7%) | 7 (5.2%) |
| Blepharitis | 1 (0.8%) | 2 (1.5%) | 6 (4.5%) |
| Vitreous detachment | 1 (0.8%) | 4 (3.0%) | 4 (3.0%) |
| Cataract | 1 (0.8%) | 3 (2.2%) | 4 (3.0%) |
| Dry eye | 4 (3.0%) | 3 (2.2%) | 4 (3.0%) |
| Diabetic retinopathy | 13 (9.8%) | 2 (1.5%) | 3 (2.2%) |
| Visual impairment | 0 | 1 (0.7%) | 4 (3.0%) |

FIG. 28

Ocular Serious TEAEs in Study Eye through Week 52

| | Sham | 2q16 | 2q8 |
|---|---|---|---|
| N (FAS/SAF) | 133 | 135 | 134 |
| # of Patients with ≥ 1 AE, n (%) | 1 (0.8%) | 0 | 1 (0.7%) |
| Visual acuity reduced | 0 | 0 | 1 (0.7%) |
| Vitreous haemorrhage | 0 | 0 | 1 (0.7%) |
| Iris neovascularisation | 1 (0.8%) | 0 | 0 |

FIG. 29

Ocular Inflammation in Study Eye through Week 52

| | — Sham | ---- 2q16 | — 2q8 |
|---|---|---|---|
| N (FAS/SAF) | 133 | 135 | 134 |
| # of injections | 0 | 749 | 1158 |
| # of Patients with ≥ 1 AE, n (%) | 0 | 1 (0.7%) (0.13% per injection) | 1 (0.7%) (0.09% per injection) |
| Anterior chamber flare | 0 | 0 | 1 (0.7%) |
| Iritis | 0 | 1 (0.7%) | 0 |

1 additional event of vitreal cells was included in the IOI table, but it was determined not to be an IOI event

FIG. 30

APTC Events through Week 52

| | —— Sham | ---- 2q16 | —— 2q8 |
|---|---|---|---|
| N (FAS/SAF) | 133 | 135 | 134 |
| Number of Patients with at Least One Such AE, n (%) | 5 (3.8%) | 4 (3.0%) | 2 (1.5%) |
| Non Fatal Stroke | 2 (1.5%) | 3 (2.2%) | 1 (0.7%) |
| Non Fatal MI | 0 | 1 (0.7%) | 0 |
| Vascular Death | 3 (2.3%) | 0 | 1 (0.7%) |

FIG. 31

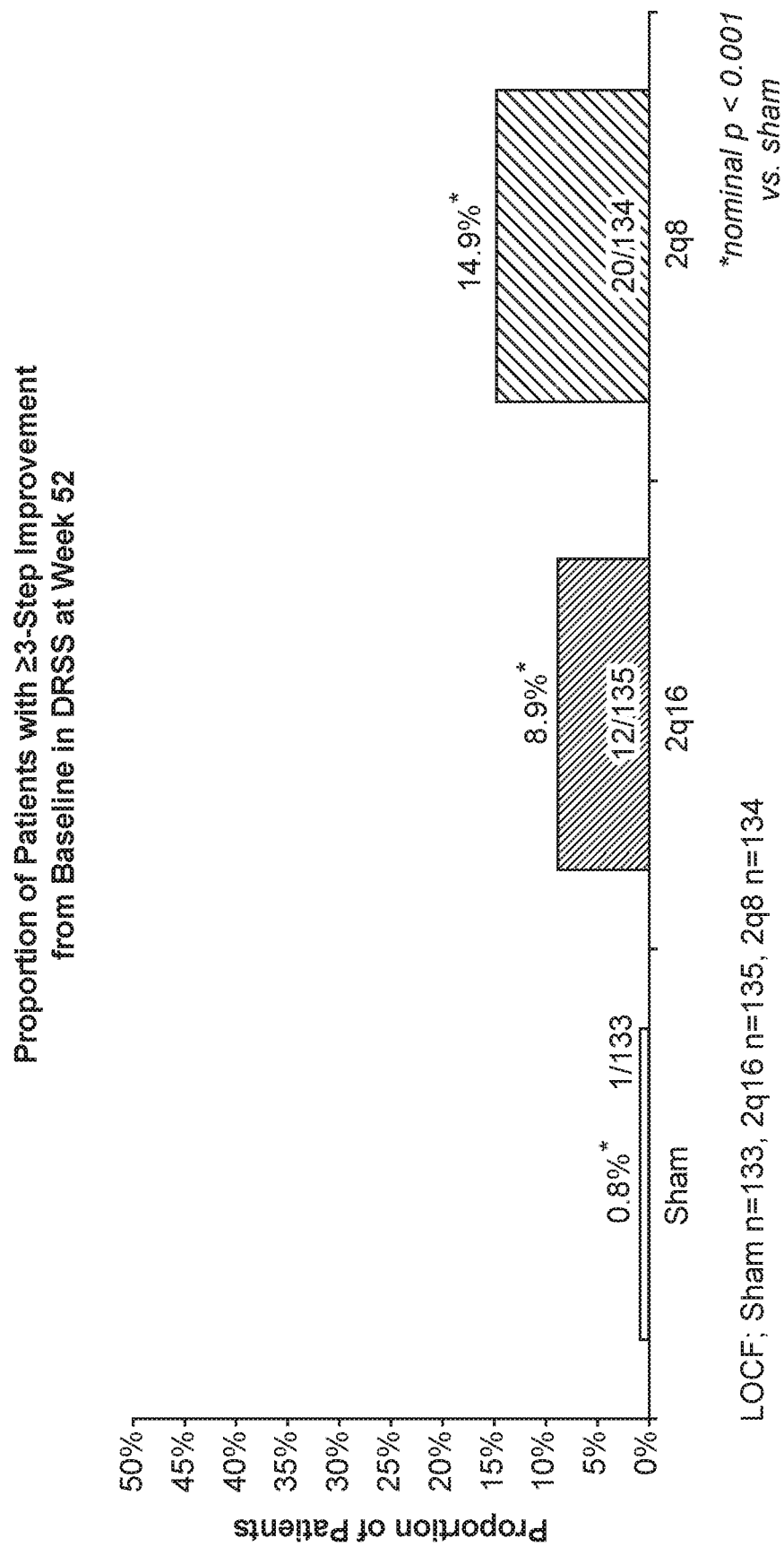

USE OF A VEGF ANTAGONIST TO TREAT ANGIOGENIC EYE DISORDERS

This application claims the benefit of U.S. provisional patent application Nos. 62/593,033, filed Nov. 30, 2017; 62/644,425, filed Mar. 17, 2018; and 62/748,782, filed Oct. 22, 2018; each of which is herein incorporated by reference in its entirety.

FIELD OF THE INVENTION

The present invention relates to the field of therapeutic treatments of eye disorders. More specifically, the invention relates to the administration of VEGF antagonists to treat eye disorders caused by or associated with angiogenesis.

BACKGROUND

Several eye disorders are associated with pathological angiogenesis. For example, the development of age-related macular degeneration (AMD) is associated with a process called choroidal neovascularization (CNV). Leakage from the CNV causes macular edema and collection of fluid beneath the macula resulting in vision loss. Diabetic macular edema (DME) is another eye disorder with an angiogenic component. DME is the most prevalent cause of moderate vision loss in patients with diabetes and is a common complication of diabetic retinopathy, a disease affecting the blood vessels of the retina. Clinically significant DME occurs when fluid leaks into the center of the macula, the light-sensitive part of the retina responsible for sharp, direct vision. Fluid in the macula can cause severe vision loss or blindness. Yet another eye disorder associated with abnormal angiogenesis is central retinal vein occlusion (CRVO). CRVO is caused by obstruction of the central retinal vein that leads to a back-up of blood and fluid in the retina. The retina can also become ischemic, resulting in the growth of new, inappropriate blood vessels that can cause further vision loss and more serious complications. Release of vascular endothelial growth factor (VEGF) contributes to increased vascular permeability in the eye and inappropriate new vessel growth. Thus, inhibiting the angiogenic-promoting properties of VEGF appears to be an effective strategy for treating angiogenic eye disorders.

FDA-approved treatments of angiogenic eye disorders such as AMD and CRVO include the administration of an anti-VEGF antibody called ranibizumab (Lucentis®, Genentech, Inc.) on a monthly basis by intravitreal injection.

Methods for treating eye disorders using VEGF antagonists are mentioned in, e.g., U.S. Pat. Nos. 7,303,746; 7,306,799; 7,300,563; 7,303,748; and US 2007/0190058. Nonetheless, there remains a need in the art for new administration regimens for angiogenic eye disorders, especially those which allow for less frequent dosing while maintaining a high level of efficacy.

BRIEF SUMMARY OF THE INVENTION

The present invention provides methods for treating angiogenic eye disorders (e.g., diabetic retinopathy, e.g., nonproliferative diabetic retinopathy). The methods of the invention comprise sequentially administering multiple doses of a VEGF antagonist to a patient over time. In particular, the methods of the invention comprise sequentially administering to the patient a single initial dose of a VEGF antagonist, followed by one or more secondary doses of the VEGF antagonist, followed by one or more tertiary doses of the VEGF antagonists. The present inventors have surprisingly discovered that beneficial therapeutic effects can be achieved in patients suffering from angiogenic eye disorders by administering a VEGF antagonist to a patient at a frequency of once every 8 or more weeks, especially when such doses are preceded by about three doses administered to the patient at a frequency of about 2 to 4 weeks. Thus, according to the methods of the present invention, each secondary dose of VEGF antagonist is administered 2 to 4 weeks after the immediately preceding dose, and each tertiary dose is administered at least 8 weeks after the immediately preceding dose. An example of a dosing regimen of the present invention is shown in FIG. 1. One advantage of such a dosing regimen is that, for most of the course of treatment (i.e., the tertiary doses), it allows for less frequent dosing (e.g., once every 8 weeks) compared to prior administration regimens for angiogenic eye disorders which require monthly administrations throughout the entire course of treatment. (See, e.g., prescribing information for Lucentis® [ranibizumab], Genentech, Inc.).

The methods of the present invention can be used to treat any angiogenic eye disorder, including, e.g., age related macular degeneration, diabetic retinopathy, diabetic macular edema, central retinal vein occlusion, corneal neovascularization, etc.

The methods of the present invention comprise administering any VEGF antagonist to the patient (e.g., by intravitreal injection). In one embodiment, the VEGF antagonist comprises one or more VEGF receptor-based chimeric molecule(s), (also referred to herein as a "VEGF-Trap" or "VEGFT"). An exemplary VEGF antagonist that can be used in the context of the present invention is a multimeric VEGF-binding protein comprising two or more VEGF receptor-based chimeric molecules referred to herein as "VEGFR1R2-FcΔC1(a)" or "aflibercept."

Various administration routes are contemplated for use in the methods of the present invention, including, e.g., topical administration or intraocular administration (e.g., intravitreal administration).

Aflibercept (EYLEA™, Regeneron Pharmaceuticals, Inc) was approved by the FDA in November 2011, for the treatment of patients with neovascular (wet) age-related macular degeneration, with a recommended dose of 2 mg administered by intravitreal injection every 4 weeks for the first three months, followed by 2 mg administered by intravitreal injection once every 8 weeks.

The present invention provides a method for treating diabetic retinopathy of any severity level, for example, nonproliferative diabetic retinopathy (NPDR) (e.g., moderately severe to severe NPDR, for example, characterized by a Diabetic Retinopathy Severity Scale level of about 47-53, e.g., 47 or 53) in a patient (e.g., a human, for example, 18 years of age or older, e.g., having type 1 or 2 diabetes) in need of such treatment, said method comprising administering (e.g., by intravitreal injection), to an eye of the patient, (i) 3 monthly doses followed by one or more secondary doses every 16 weeks, wherein the first secondary dose initiates 8 weeks after the third monthly dose (week 16) and continues thereafter every 16 weeks (e.g., wherein a dose is given at week 32, 48, 64, etc.) (see e.g., FIG. 2), or (ii) 3 or 4 or 5 monthly doses followed by one or more secondary doses every 8 weeks, wherein the secondary doses initiate 8 weeks after the final of the 3 or 4 or 5 monthly doses and continues with a dose given every 8 weeks thereafter;

of about 2 mg of VEGF antagonist which is, for example, a VEGF receptor-based chimeric molecule, for example, that comprises (1) a VEGFR1 component comprising amino acids 27 to 129 of SEQ ID NO:2; (2) a VEGFR2 component comprising amino acids 130-231 of SEQ ID NO:2; and (3) a multimerization component comprising amino acids 232-457 of SEQ ID NO:2. For example, in an embodiment of the invention, the VEGF antagonist is Aflibercept. In an embodiment of the invention, the VEGF antagonist comprises VEGFR1R2-FcΔC1(a) encoded by the nucleic acid sequence of SEQ ID NO:1. In an embodiment of the invention, the patient is characterized as not suffering from diabetic macular edema; having a baseline best-corrected visual acuity (BCVA) ETDRS letter score of 69 or greater; having vision characterized by a Snellen visual acuity of 20/40 or better; does not suffer from retinal neovascularization; does not suffer from anterior segment neovascularization (ASNV); does not suffer from vitreous hemorrhage; and/or does not suffer from tractional retinal detachment. In an embodiment of the invention, "treating" NPDR in a patient, as discussed herein, refers to bringing about at least a 2-step improvement in DRSS (Diabetic Retinopathy Severity Scale) from baseline (before the first VEGF antagonist administration), for example, by week 24 or 48 or 52 (relative to commencement of first VEGF antagonist administration).

The present invention provides a method for treating or preventing proliferative diabetic retinopathy (PDR) in a patient (e.g., a human) in need of such treatment or prevention; or for preventing progression of non-proliferative diabetic retinopathy (NPDR) to proliferative diabetic retinopathy, anterior segment neovascularization (ASNV), diabetic macular edema (DME) or center involved diabetic macular edema (CI-DME), wherein the patient is initially treated for non-proliferative diabetic retinopathy (e.g., wherein the patient has type 1 or 2 diabetes; has a hemoglobin A1c of about 8.5; has an ETDRA BCVA score of about 82; has a central retinal thickness of about 247 μm; has a diabetic retinopathy severity score of 47 or 53; and/or is about 56 years of age), said method comprising administering, to an eye of the patient (e.g., by intravitreal injection), (i) 3 monthly doses followed by one or more secondary doses every 16 weeks, wherein the first secondary dose initiates 8 weeks after the third monthly dose (week 16), or
(ii) 3 or 4 or 5 monthly doses followed by one or more secondary doses every 8 weeks;

of about 2 mg of VEGF antagonist, e.g., that comprises (1) a VEGFR1 component comprising amino acids 27 to 129 of SEQ ID NO:2; (2) a VEGFR2 component comprising amino acids 130-231 of SEQ ID NO:2; and (3) a multimerization component comprising amino acids 232-457 of SEQ ID NO:2 (e.g., aflibercept). For example, in an embodiment of the invention, the patient is treated for at least about 24 weeks, 52 weeks or 100 weeks, e.g., wherein the patient receives about 3 to about 5 injections over the 24 week period. In an embodiment of the invention, the patient is treated, e.g., for about 24 or more weeks, and achieves one or more of the following benefits:

(i) at least a 2 step improvement from baseline in diabetic retinopathy severity scale (DRSS) score;
(ii) at least a 3 step improvement from baseline in diabetic retinopathy severity scale (DRSS) score;
(iii) an improvement in best corrected visual acuity of at least about 1.9 letters;
(iv) does not experience a reduction in best corrected visual acuity of any more than 4 letters;
(v) does not develop diabetic macular edema;
(vi) does not develop center involved diabetic macular edema;
(vii) does not experience a vision threatening complication;
(viii) does not develop proliferative diabetic retinopathy;
(ix) does not develop anterior segment neovascularization; and/or (x) experiences a reduction in central retinal thickness of about 19 μm. Thus, the present invention also provides methods for causing a patient with non-proliferative diabetic retinopathy to achieve one or more of the following benefits (i) at least a 2 step improvement from baseline in diabetic retinopathy severity scale (DRSS) score;
(ii) at least a 3 step improvement from baseline in diabetic retinopathy severity scale (DRSS) score;
(iii) an improvement in best corrected visual acuity of at least about 1.9 letters;
(iv) does not experience a reduction in best corrected visual acuity of any more than 4 letters;
(v) does not develop diabetic macular edema;
(vi) does not develop center involved diabetic macular edema;
(vii) does not experience a vision threatening complication;
(viii) does not develop proliferative diabetic retinopathy;
(ix) does not develop anterior segment neovascularization; and/or
(x) experiences a reduction in central retinal thickness of about 19 μm; by administering a VEGF antagonist according to the dosing regimen set forth above.

For example, the present invention provides a method for causing a reduction or preventing an increase in the Diabetic Retinopathy Severity Scale (DRSS) level (see e.g., FIG. 18) (e.g., by at least 2 or 3 levels) of nonproliferative diabetic retinopathy in a patient comprising administering, to an eye of the patient (e.g., by intravitreal injection), (i) 3 monthly doses followed by one or more secondary doses every 16 weeks, wherein the first secondary dose initiates 8 weeks after the third monthly dose (week 16), or
(ii) 3 or 4 or 5 monthly doses followed by one or more secondary doses every 8 weeks;

of about 2 mg of VEGF antagonist, e.g., that comprises (1) a VEGFR1 component comprising amino acids 27 to 129 of SEQ ID NO:2; (2) a VEGFR2 component comprising amino acids 130-231 of SEQ ID NO:2; and (3) a multimerization component comprising amino acids 232-457 of SEQ ID NO:2 (e.g., aflibercept).

The present invention also provides a method for treating or preventing the occurrence or re-occurrence of a vision threating complication or blindness in the eye of a subject (e.g., a human) whose eye has nonproliferative diabetic retinopathy comprising administering (e.g., by intravitreal injection), to an eye of the subject (e.g., by intravitreal injection), (i) 3 monthly doses followed by one or more secondary doses every 16 weeks, wherein the first secondary dose initiates 8 weeks after the third monthly dose (week 16), or (ii) 3 or 4 or 5 monthly doses followed by one or more secondary doses every 8 weeks; of about 2 mg of VEGF antagonist that is a VEGF receptor-based chimeric molecule. Optionally, the other eye of the subject is also administered the VEGF antagonist even if not so afflicted, afflicted with DRSS of a lower level or afflicted with another angiogenic eye disorder. For example, in an embodiment of the invention, the VEGF antagonist is a VEGF receptor-based chimeric molecule which (i) comprises (1) a VEGFR1 component comprising amino acids 27 to 129 of SEQ ID NO:2; (2) a VEGFR2 component comprising amino acids 130-231 of SEQ ID NO:2; and (3) a multimerization component comprising amino acids 232-457 of SEQ ID NO:2; (ii) comprises (1) an immunoglobin-like (Ig) domain 2 of a first VEGF receptor and (2) Ig domain 3 of a second VEGF receptor, and (3) a multimerizing component; (iii) is aflibercept; or (iv) is conbercept.

One aspect of the invention is a package, comprising:
a drug container; and
instructions for using the drug for treating or preventing diabetic retinopathy in a patient in need of such treatment, the instructions indicating a use of the drug by administering the drug to an eye of the patient,
(i) 3 monthly doses followed by one or more secondary doses every 16 weeks, wherein the first secondary dose initiates 8 weeks after the third monthly dose (week 16), or
(ii) 3 or 5 monthly doses followed by one or more secondary doses every 8 weeks; of about 2 mg of VEGF antagonist that is a VEGF receptor-based chimeric molecule.

Another aspect of the invention is a package wherein the VEGF antagonist
(i) comprises (1) a VEGFR1 component comprising amino acids 27 to 129 of SEQ ID NO:2; (2) a VEGFR2 component comprising amino acids 130-231 of SEQ ID NO:2; and (3) a multimerization component comprising amino acids 232-457 of SEQ ID NO:2;
(ii) comprises (1) an immunoglobin-like (Ig) domain 2 of a first VEGF receptor and (2) Ig domain 3 of a second VEGF receptor, and (3) a multimerizing component;
  (iii) is aflibercept; or
  (iv) is conbercept.

Another aspect of the invention is a package wherein the instructions indicate the drug is administered by intravitreal injection.

Another aspect of the invention is a package wherein the instructions indicate the drug is administered 3 or 5 monthly doses followed by one or more doses every 8 weeks.

Another aspect of the invention is a package wherein the instructions indicate the drug is administered 3 monthly doses followed by one or more secondary doses every 16 weeks, wherein the first secondary dose initiates 8 weeks after the third monthly dose (week 16).

Another aspect of the invention is a package wherein the instructions indicate the drug is administered one dose every 8 weeks.

An aspect of the invention is a package, comprising:
a drug container; and
instructions for using the drug for treating or preventing proliferative diabetic retinopathy in a patient in need of such treatment, the instructions indicating a use of the drug by administering the drug to an eye of the patient,
(i) 3 monthly doses followed by one or more secondary doses every 16 weeks, wherein the first secondary dose initiates 8 weeks after the third monthly dose (week 16), or
(ii) 3 or 5 monthly doses followed by one or more secondary doses every 8 weeks; of about 2 mg of VEGF antagonist that is a VEGF receptor-based chimeric molecule.

Another aspect of the invention is a package wherein the VEGF antagonist
(i) comprises (1) a VEGFR1 component comprising amino acids 27 to 129 of SEQ ID NO:2; (2) a VEGFR2 component comprising amino acids 130-231 of SEQ ID NO:2; and (3) a multimerization component comprising amino acids 232-457 of SEQ ID NO:2;
(ii) comprises (1) an immunoglobin-like (Ig) domain 2 of a first VEGF receptor and (2) Ig domain 3 of a second VEGF receptor, and (3) a multimerizing component;
  (iii) is aflibercept; or
  (iv) is conbercept.

Other embodiments of the present invention will become apparent from a review of the ensuing detailed description.

BRIEF DESCRIPTION OF THE FIGURES

FIG. 4 summarizes the PANORAMA dosing schedule of the sham, Group 1 and Group 2 groups. X=Active injections; O=sham injections.

FIG. 5 describes the baseline disposition and demographics of the PANORAMA study population in each dosing group including: sham, Group 1, Group 2 and the combination of Group 1 and Group 2 (All IAI). IAI=Intravitreal aflibercept injection.

FIG. 6 describes the baseline disease characteristics of the PANORAMA study population in each dosing group including: sham, Group 1, Group 2 and the combination of Group 1 and Group 2 (All IAI).

FIG. 13 summarizes the study eye ocular treatment emergent adverse events (TEAEs) in the sham and All IAI (combined Group 1 and Group 2) PANORAMA groups through week 24. FAS/SAF=full analysis set/safety analysis set.

FIG. 14 summarizes the study eye ocular serious treatment emergent adverse events (TEAEs) in the sham and All IAI (combined Group 1 and Group 2) PANORAMA groups through week 24. FAS/SAF=full analysis set/safety analysis set.

FIG. 15 summarizes the study eye intra-ocular inflammation experienced by the sham and All IAI (combined Group 1 and Group 2) PANORAMA groups through week 24.

FIG. 16 summarizes the anti-platelet trialists' collaboration (APTC) events experienced by sham and All IAI (combined Group 1 and Group 2) PANORAMA groups through week 24.

FIG. 17 summarizes the deaths of PANORAMA subjects through week 24.

FIG. 18 is an International Clinical Diabetic Retinopathy Disease Severity Scale (DRSS) Detailed Table.

FIG. 28 summarizes the incidence of ocular treatment-emergent adverse events (TEAEs) experienced by subjects, in the treatment eye, in each treatment group (sham, 2q16 and 2q8) after 52 weeks.

FIG. 29 summarizes the incidence of serious ocular treatment-emergent adverse events (TEAEs) experienced by subjects, in the treatment eye, in each treatment group (sham, 2q16 and 2q8) after 52 weeks.

FIG. 30 summarizes the incidence of ocular inflammation experienced by subjects, in the treatment eye, in each treatment group (sham, 2q16 and 2q8) after 52 weeks.

FIG. 31 summarizes the incidence of anti-platelet trialists' collaboration (APTC) events experienced by subjects, in the treatment eye, in each treatment group (sham, 2q16 and 2q8) after 52 weeks.

FIG. 32 summarizes the proportion of patents with a three step improvement or more in each treatment group (sham, 2q16 and 2q8) after 52 weeks.

DETAILED DESCRIPTION

Figure 1:
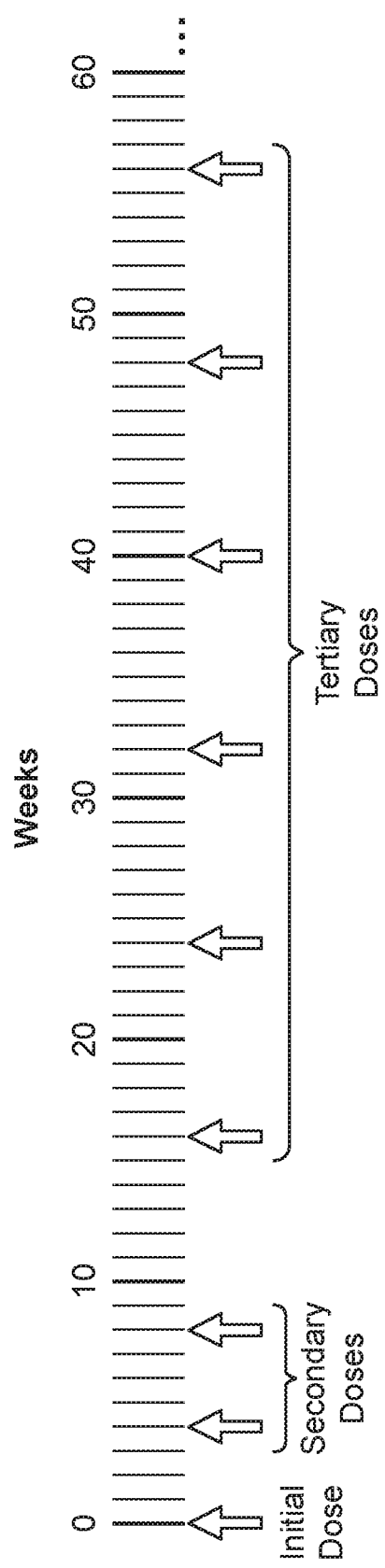
FIG. 1 shows an exemplary dosing regimen of the present invention. In this regimen, a single "initial dose" of VEGF antagonist ("VEGFT") is administered at the beginning of the treatment regimen (i.e. at "week 0"), two "secondary doses" are administered at weeks 4 and 8, respectively, and at least six "tertiary doses" are administered once every 8 weeks thereafter, i.e., at weeks 16, 24, 32, 40, 48, 56, etc.). This VEGF antagonist dosage regimen forms part of the present invention.

The present invention includes an exceptionally effective method for preventing the progression of non-proliferative diabetic retinopathy without diabetic macular edema in a patient to more advanced and vision threatening disorders such as proliferative diabetic retinopathy, diabetic macular edema and/or anterior segment neovascularization of the eye. Indeed, moderately severe to severe non-proliferative diabetic retinopathy patients on the aflibercept dosing regimens of the present invention experienced a reversal of disease progression achieving a two or more step improvement in DRSS level. The eyes of subjects on the dosing regimens of the present invention also experienced a reduction in the occurrence of vision threatening complications relative to untreated eyes. This prevention can be achieved by administration of a VEGF antagonist, such as aflibercept, to the eye of a patient using the dosing regimens set forth herein.

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice or testing of the present invention, the preferred methods and materials are now described.

A subject or a patient can be a mammal, for example a human (e.g., a human 50, 55, 60, 65 or 70 years of age or older), rabbit, mouse, non-human primate, monkey or rat. In an embodiment of the invention, the subject or patient previously received a different treatment for DR, e.g., PDR (e.g., panretinal photocoagulation (laser) therapy). In an embodiment of the invention, the previous treatment failed to sufficiently treat the DR. In an embodiment of the invention, the patient or subject does not suffer from DME and/or CI-DME. In an embodiment of the invention, the subject or patient has diabetes (e.g., type 1 or type 2).

Dosing Regimens

The present invention provides methods for treating angiogenic eye disorders such as diabetic retinopathy of any severity level, for example, proliferative or nonproliferative diabetic retinopathy (NPDR), e.g., moderately severe NPDR or severe NPDR. The methods of the invention comprise sequentially administering to the eye of a subject or patient (e.g., a human such as a human 18 years of age or older) multiple doses of a VEGF antagonist (e.g., aflibercept). In an embodiment of the invention, the patient has diabetes (e.g., type 1 or type 2). As used herein, "sequentially administering" means that each dose of VEGF antagonist is administered to the eye of a patient at a different point in time, e.g., on different days separated by a predetermined interval (e.g., hours, days, weeks or months). The present invention includes methods which comprise sequentially administering to the eye of a patient a single initial dose of a VEGF antagonist, followed by one or more secondary doses of the VEGF antagonist, followed by one or more tertiary doses of the VEGF antagonist.

The present invention provides methods for treating or preventing an angiogenic eye disorder (e.g., NPDR); preventing progression of DR (e.g., NPDR) to a more severe form or complication thereof, e.g., to PDR, ASNV, DME and/or CI-DME; causing a reduction in DRSS of NPDR; treating or preventing the occurrence or re-occurrence of a VTC or blindness, in a subject, comprising administering, to the eye of the subject, three or four or five initial monthly doses of VEGF antagonist (e.g., aflibercept) followed by one or more secondary doses every eight weeks. In an embodiment of the invention, the eye suffering from the disorder is administered the antagonist and, optionally, the other eye is also treated with the same or a different dosing regimen even if the disorder has not manifested in that eye or if a less severe form of the disorder has manifested or if another angiogenic eye disorder afflicts the other eye. The present invention, thus, provides methods including administering a 0.5 or 2 mg dose of VEGF antagonist (e.g., by intravitreal injection) to an eye of a subject (e.g., a human) as 3 or 4 or 5 monthly doses followed by a dose every 8 weeks counted from the last of the initial 3 or 4 or 5 monthly doses. In an embodiment of the invention, the eye suffering from the disorder is administered the antagonist and, optionally, the other eye is also treated with the same or a different dosing regimen even if the disorder has not manifested in that eye or if a less severe form of the disorder has manifested or if another angiogenic eye disorder afflicts the other eye. In one exemplary embodiment of the present invention, a single initial dose of a VEGF antagonist (e.g., 2 mg) is administered to a patient's eye (e.g., by intravitreal injection) on the first day of the treatment regimen (i.e., at week 0), followed by two secondary doses, each administered four weeks after the immediately preceding dose (i.e., at week 4 and at week 8), followed by at least 5 tertiary doses, each administered eight weeks after the immediately preceding dose (i.e., at weeks 16, 24, 32, 40 and 48). The tertiary doses may continue (at intervals of 8 or more weeks) indefinitely during the course of the treatment regimen. This exemplary administration regimen is depicted graphically in FIG. 1.

Figure 2:
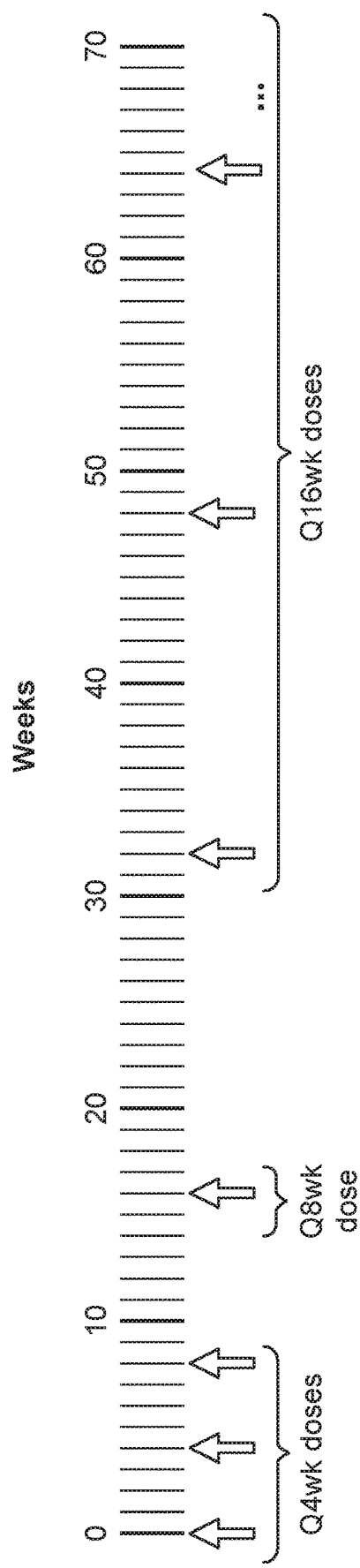
FIG. 2 shows a second exemplary dosing regimen of the present invention. In this regimen, three monthly doses ("Q4wk doses") of a VEGF antagonist are administered at the beginning of the treatment regimen (i.e., at weeks 0, 4 and 8), a single dose is then administered 8 weeks after the last Q4wk dose ("Q8wk dose") (i.e., at week 16), followed by three or more additional doses administered 16 weeks after the Q8wk dose and once every 16 weeks thereafter ("Q16wk doses") (i.e., at weeks 32, 48, 64, etc.). This VEGF antagonist dosage regimen forms part of the present invention.

The present invention also includes methods for treating or preventing an angiogenic eye disorder (e.g., NPDR); preventing progression of DR (e.g., NPDR) to a more severe form or complication thereof, e.g., to PDR, ASNV, DME and/or CI-DME; causing a reduction in DRSS of NPDR; treating or preventing the occurrence or re-occurrence of a VTC or blindness, in a subject, the methods comprising administering (e.g., by intravitreal injection) to an eye of the subject:

(A) three initial monthly doses (e.g., once every 4 weeks or "Q4wk") of a VEGF antagonist (e.g., 2 mgs); followed by
(B) administering to the eye of the subject a single dose (e.g., 2 mg) of the VEGF antagonist 8 weeks after the immediately preceding dose ("Q8wk"); followed by
(C) administering to the eye of the subject one or more further (maintenance) doses (e.g., 2 mg) of the VEGF antagonist (e.g., aflibercept) 16 weeks after the immediately preceding dose and once every 16 weeks ("Q16wk") thereafter (at weeks 32, 48 and 64, etc., counted from the first of the initial monthly doses). See, for example, FIG. 2. A method of the present invention comprises administering a VEGF antagonist as (i) 3 monthly doses followed by one or more secondary doses every 16 weeks, wherein the first secondary dose initiates 8 weeks after the third monthly dose (week 16). In an embodiment of the invention, the eye suffering from the disorder is administered the antagonist and, optionally, the other eye is also treated with the same or a different dosing regimen even if the disorder has not manifested in that eye or if a less severe form of the disorder has manifested or if another angiogenic eye disorder afflicts the other eye.

In one exemplary embodiment of the present invention, following an initial primary dose, each secondary dose is administered 2 to 4 (e.g., 2, 2½, 3, 3½, or 4) weeks after the immediately preceding dose, and each tertiary dose is administered at least 8 (e.g., 8, 8½, 9, 9½, 10, 10½, 11, 11½, 12, 12½, 13, 13½, 14, 14½, or more) weeks after the immediately preceding dose. Alternatively, following the secondary doses, the VEGF antagonist is administered on an as needed/pro re nata (PRN) basis, based on visual and/or anatomical outcomes as assessed by a physician or other qualified medical professional.

The present invention also includes methods for treating or preventing an angiogenic eye disorder (e.g., NPDR); preventing progression of DR (e.g., NPDR) to a more severe form or complication thereof, e.g., to PDR, ASNV, DME and/or CI-DME; causing a reduction in DRSS of NPDR; treating or preventing the occurrence or re-occurrence of a VTC or blindness, in a subject, the methods comprising administering (e.g., by intravitreal injection) to an eye of the subject:

(A) three initial monthly doses (e.g., once every 4 weeks or "Q4wk") of a VEGF antagonist (e.g., aflibercept or conbercept, e.g., 0.5 mg or 2.0 mg); followed by
(B)
administering the VEGF antagonist to the eye of the subject one or more doses of the VEGF antagonist 3 months after the immediately preceding dose (or every 12 weeks or quarterly); or
administering the VEGF antagonist to the eye of the subject on an as needed/pro re nata (PRN) basis, based on visual and/or anatomical outcomes as assessed by a physician or other qualified medical professional.

The terms "initial dose," "secondary doses," and "tertiary doses," refer to the temporal sequence of administration of the VEGF antagonist. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of VEGF antagonist, but will generally differ from one another in terms of frequency of administration. In certain embodiments, however, the amount of VEGF antagonist contained in the initial, secondary and/or tertiary doses will vary from one another (e.g., adjusted up or down as appropriate) during the course of treatment.

The phrase "the immediately preceding dose," as used herein, means, in a sequence of multiple administrations, the dose of VEGF antagonist which is administered to the eye of a patient prior to the administration of the very next dose in the sequence with no intervening doses.

In an embodiment of the invention, the VEGF antagonist dosing regimen is conducted over the course of 24, 48, 52, 96 or 100 weeks (or more).

In an embodiment of the invention, patients (e.g., suffering from NPDR) receiving such a dosing regimen exhibit at least a 2-step improvement in DRSS (Diabetic Retinopathy Severity Scale) from baseline (before treatment commences) at week 24 or 48 or 52 in the eye. In an embodiment of the invention, a 3-step improvement is experienced in the eye.

The methods of the invention may comprise administering to the eye of a patient any number of secondary and/or tertiary doses of a VEGF antagonist. For example, in certain embodiments, only a single secondary dose is administered to the patient's eye. In other embodiments, two or more (e.g., 2, 3, 4, 5, 6, 7, 8, or more) secondary doses are administered to the patient's eye. Likewise, in certain embodiments, only a single tertiary dose is administered to the patient's eye. In other embodiments, two or more (e.g., 2, 3, 4, 5, 6, 7, 8, or more) tertiary doses are administered to the patient's eye.

In embodiments involving multiple secondary doses, each secondary dose may be administered at the same frequency as the other secondary doses. For example, each secondary dose may be administered to the patient's eye 4 weeks after the immediately preceding dose. Similarly, in embodiments involving multiple tertiary doses, each tertiary dose may be administered at the same frequency as the other tertiary doses. For example, each tertiary dose may be administered to the patient's eye 8 weeks after the immediately preceding dose. Alternatively, the frequency at which the secondary and/or tertiary doses are administered to a patient's eye can vary over the course of the treatment regimen. For example, the present invention includes methods which comprise administering to the patient's eye a single initial dose of a VEGF antagonist, followed by one or more secondary doses of the VEGF antagonist, followed by at least 5 tertiary doses of the VEGF antagonist, wherein the first four tertiary doses are administered 8 weeks after the immediately preceding dose, and wherein each subsequent tertiary dose is administered from 8 to 12 (e.g., 8, 8½, 9, 9½, 10, 10½, 11, 11½, 12) weeks after the immediately preceding dose. The frequency of administration may also be adjusted during the course of treatment by a physician depending on the needs of the individual patient following clinical examination.

In an embodiment of the invention, a VEGF antagonist is administered to a subject according to a dosing regimen of the present invention in association with a further therapeutic agent (e.g., a vitamin or dietary supplement) or therapeutic procedure (e.g. laser therapy or surgery). For example, in an embodiment or the invention, the subject receives laser therapy, such as pan-retinal photocoagulation (laser) therapy, in association with the VEGF antagonist. In an embodiment of the invention, the subject received the laser therapy previously, for example to treat DR (e.g., PDR), but switched to a VEGF antagonist dosing regimen according to the present invention.

The term "in association with" indicates that the components, a VEGF antagonist along with a further therapeutic agent can be formulated into a single composition, e.g., for simultaneous delivery, or formulated separately into two or more compositions (e.g., a kit). Each component can be administered to a subject at a different time than when the other component is administered; for example, each administration may be given non-simultaneously (e.g., separately or sequentially) at intervals over a given period of time. Moreover, the separate components may be administered to a subject by the same or by a different route.

VEGF Antagonists

The methods of the present invention comprise administering to a patient's eye a VEGF antagonist according to specified dosing regimens set forth herein. As used herein, the expression "VEGF antagonist" means any molecule that blocks, reduces or interferes with the normal biological activity of VEGF.

VEGF antagonists include molecules which interfere with the interaction between VEGF and a natural VEGF receptor, e.g., molecules which bind to VEGF or a VEGF receptor and prevent or otherwise hinder the interaction between VEGF and a VEGF receptor. Specific exemplary VEGF antagonists include anti-VEGF antibodies and antigen-binding fragments thereof (e.g., Fab or F(ab)$_2$), anti-VEGF receptor antibodies and antigen-binding fragments thereof, anti-VEGF and anti-VEGF receptor single chain antibodies, anti-VEGF and anti-VEGF receptor bispecific antibodies and antigen-binding fragments thereof, anti-VEGF and anti-VEGF receptor DARPins (designed ankyrin repeat proteins) and VEGF receptor-based chimeric molecules (also referred to herein as "VEGF-Traps").

VEGF receptor-based chimeric molecules include chimeric polypeptides which comprise two or more immunoglobulin (Ig)-like domains of a VEGF receptor such as VEGFR1 (also referred to as Flt1) and/or VEGFR2 (also referred to as Flk1 or KDR), and may also contain a multimerizing domain (e.g., an Fc domain which facilitates the multimerization [e.g., dimerization] of two or more chimeric polypeptides). An exemplary VEGF receptor-based chimeric molecule is a molecule referred to as VEGFR1R2-FcΔC1(a) which is encoded by the nucleic acid sequence of SEQ ID NO:1. VEGFR1R2-FcΔC1(a) comprises three components: (1) a VEGFR1 component comprising amino acids 27 to 129 of SEQ ID NO:2; (2) a VEGFR2 component comprising amino acids 130 to 231 of SEQ ID NO:2; and (3) a multimerization component ("FcΔC1(a)") comprising amino acids 232 to 457 of SEQ ID NO:2 (the C-terminal amino acid of SEQ ID NO:2 [i.e., K458] which may or may not be included in the VEGF antagonist used in the methods of the invention; see e.g., U.S. Pat. No. 7,396,664). Amino acids 1-26 of SEQ ID NO: 2 are the signal sequence.

The VEGF antagonist used in the Examples set forth herein below is a molecule comprising the VEGFR1R2-FcΔC1(a) molecule (e.g., a homodimer thereof) and is referred to herein as "VEGFT." Additional VEGF receptor-based chimeric molecules which can be used in the context of the present invention are disclosed in U.S. Pat. Nos. 7,396,664, 7,303,746 and WO 00/75319.

In an embodiment of the invention, the VEGF antagonist is a VEGF receptor based chimeric molecule that is a polypeptide (or a homodimer thereof) that comprises:
(1) an immunoglobin-like (Ig) domain 2 of a first VEGF receptor (e.g., VEGFR1);
(2) Ig domain 3 of a second VEGF receptor (e.g., VEGFR2); and (3) a multimerizing component (e.g., an Fc or variant thereof).

In an embodiment of the invention, the VEGF antagonist is a VEGF receptor based chimeric molecule that is a polypeptide (or homodimer thereof) that comprises:
(1) an immunoglobin-like (Ig) domain 2 of a first VEGF receptor (e.g., VEGFR1);
(2) Ig domain 3 of a second VEGF receptor (e.g., VEGFR2);
(3) an immunoglobulin-like (Ig) domain 4 of the second VEGF receptor (e.g., VEGFR2); and
(4) a multimerizing component (e.g., an Fc or variant thereof).

Exemplary VEGF antagonists that can be used in the context of the present invention include, e.g., VEGF mini-Trap (see e.g., U.S. Pat. No. 7,087,411), aflibercept, an anti-VEGF DARPin such as the Abicipar Pegol DARPin), a single chain (e.g., VL-VH) anti-VEGF antibody such as brolucizumab (RTH258), a monospecific, multispecific or bispecific anti-VEGF antibody or antigen-binding fragment thereof, e.g., which also binds to ANG2, such as RG7716, ranibizumab (LUCENTIS), or bevacizumab (AVASTIN), and conbercept.

Angiogenic Eye Disorders

The methods of the present invention can be used to treat or prevent any angiogenic eye disorder by administering to the eye of the subject, a therapeutically effective amount of VEGF antagonist (e.g., 2 mg aflibercept) according to a dosing regimen which is set forth herein. The expression "angiogenic eye disorder," as used herein, means any disease of the eye which is caused by or associated with the growth or proliferation of blood vessels or by blood vessel leakage. Non-limiting examples of angiogenic eye disorders that are treatable using the methods of the present invention include age-related macular degeneration (e.g., wet AMD, exudative AMD, etc.), retinal vein occlusion (RVO), central retinal vein occlusion (CRVO; e.g., macular edema following CRVO), branch retinal vein occlusion (BRVO), diabetic macular edema (DME), choroidal neovascularization (CNV; e.g., myopic CNV), iris neovascularization, neovascular glaucoma, post-surgical fibrosis in glaucoma, proliferative vitreoretinopathy (PVR), optic disc neovascularization, corneal neovascularization, retinal neovascularization, vitreal neovascularization, pannus, pterygium, vascular retinopathy and diabetic retinopathies such as nonproliferative diabetic retinopathy and proliferative diabetic retinopathy.

Diabetic retinopathy is a progressive condition that can occur in people who have diabetes. Typically, it causes progressive damage to the retina, the light-sensitive lining at the back of the eye. Diabetic retinopathy is a serious sight-threatening complication of diabetes. Over time, diabetes damages the blood vessels in the retina and diabetic retinopathy occurs when these tiny blood vessels leak blood and other fluids. The condition typically affects both eyes. The longer a person has diabetes, the more likely they will develop diabetic retinopathy. If left untreated, diabetic retinopathy can cause blindness.

Symptoms of diabetic retinopathy may include:
Seeing spots or floaters
Blurred vision
Having a dark or empty spot in the center of your vision
Difficulty seeing well at night Thus, in order to preserve vision, it is critical to halt or impede progression of diabetic retinopathy to its more sight-threatening later stages, e.g., proliferative diabetic retinopathy, diabetic macular edema and/or anterior segment neovascularization (ASNV). Klein et al., Changes in Retinal Vessel Diameter and Incidence and Progression of Diabetic Retinopathy, Arch. Opthamol. 130(6): 749-755 (2012).

Anterior segment neovascularization is neovascularization of the iris, and/or definitive neovascularization of the iridocorneal angle.

As diabetic retinopathy progresses, it reaches more advanced stages including:
1. Mild nonproliferative retinopathy. This stage is characterized by small areas of balloon-like swelling in the retina's tiny blood vessels, called microaneurysms. These microaneurysms may leak fluid into the retina; then
2. Moderate nonproliferative retinopathy. As the disease progresses, blood vessels that nourish the retina may swell and distort. They may also lose their ability to transport blood. Both conditions cause characteristic changes to the appearance of the retina and may contribute to diabetic macular edema; then
3. Severe nonproliferative retinopathy. In this stage, many more blood vessels are blocked, depriving blood supply to areas of the retina. These areas secrete growth factors that signal the retina to grow new blood vessels; and then
4. Proliferative diabetic retinopathy (PDR). See below.

Nonproliferative diabetic retinopathy (NPDR) is an early retinopathy in diabetic patients which is not characterized by neovascularization and whose stage may also be graded according to the Diabetic Retinopathy Severity Scale (DRSS). Grades of NPDR include, for example, early, moderate, moderately severe and severe. In an embodiment of the invention, moderately severe to severe NPDR is accorded a severity level of 47 to 53 (e.g., 47 or 53). In an embodiment of the invention, a moderately severe to severe NPDR patient (e.g., a human, for example 18 years of age or older with type 1 or type 2 diabetes) is characterized with one or more of the following:
without macular edema (e.g., threatening the center of the macula);
can safely defer panretinal photocoagulation for at least 6 months;
has a baseline best-corrected visual acuity (BCVA) ETDRS letter score of 69 or greater (e.g., Snellen visual acuity of 20/40 or better);
without retinal neovascularization;
without anterior segment neovascularization (ASNV);
without vitreous hemorrhage; and/or
without tractional retinal detachment.

Proliferative diabetic retinopathy (PDR) is the more advanced form of diabetic retinopathy. At this stage, new fragile blood vessels can begin to grow in the retina and into the vitreous, the gel-like fluid that fills the back of the eye. The new blood vessel may leak blood into the vitreous, clouding vision.

Thus, the present invention includes methods for treating or preventing diabetic retinopathy in a subject's eye, whether the subject's eye has moderately severe NPDR (nonproliferative diabetic retinopathy) or severe NPDR (e.g., moderately severe to severe NPDR) or PDR (proliferative diabetic retinopathy), e.g., where the DRSS for the subjects diabetic retinopathy is 47 or 53, by administering a VEGF antagonist (e.g., 2 mg of aflibercept) to the subject's eye under a dosing regimen set forth herein. In an embodiment of the invention, the subject does not suffer from diabetic macular edema (DME) and/or center-involved diabetic macular edema (CI-DME). In a patient with a nonproliferative diabetic retinopathy, the dosing regimens set forth herein may be used to prevent the progression of the patient to a more severe form of NPDR or to a proliferative diabetic retinopathy, ASNV, DME and/or CI-DME. Indeed, the dosing regimens of the present invention may be used to reverse an increase in (or prevent an increase in) DRSS in a patient suffering from NPDR (e.g., who does not suffer from DME and/or CI-DME) by as much as, for example, 2 levels or more, e.g., 3 levels.

The International Clinical Diabetic Retinopathy Disease Severity Scale (DRSS), including levels thereof, is detailed in a table set forth in FIG. 18.

Subjects suffering from NPDR are at risk of suffering from various vision threatening complications or events (VTCs) and blindness (e.g., blindness secondary to such a VTC). Vision threatening complications are defined as composite outcome of PDR (inclusive of patients who have vitreous hemorrhage or tractional retinal detachment believed to be due to PDR) and ASNV. ASNV is defined as neovascularization of the iris (at least 2 cumulative clock hours), and/or definitive neovascularization of the iridocorneal angle. The dosing regimens reduce incidence of such VTCs and/or blindness in subjects suffering from NPDR. Thus, the present invention provides methods for preventing the occurrence or re-occurrence (following one or more initial occurrences) of a VTC and/or blindness in a subject who, for example, suffers from NPDR or PDR by administering, to the subject's eye, a VEGF antagonist (aflibercept, e.g., 2.0 mg) under a dosing regimen set forth herein. Such methods may include not only the step of treating one eye suffering a VTC, but also treating the other eye even if no VTC and/or blindness has occurred in the other eye so as to prevent a VTC and/or blindness.

Pharmaceutical Formulations

The present invention includes methods in which the VEGF antagonist that is administered to the patient's eye is contained within a pharmaceutical formulation. The pharmaceutical formulation may comprise the VEGF antagonist along with at least one inactive ingredient such as, e.g., a pharmaceutically acceptable carrier. Other agents may be incorporated into the pharmaceutical composition to provide improved transfer, delivery, tolerance, and the like. The term "pharmaceutically acceptable" means approved by a regulatory agency of the Federal or a state government or listed in the U.S. Pharmacopeia or other generally recognized pharmacopeia for use in animals, and more particularly, in humans. The term "carrier" refers to a diluent, adjuvant, excipient, or vehicle with which the antibody is administered. A multitude of appropriate formulations can be found in the formulary known to all pharmaceutical chemists: Remington's Pharmaceutical Sciences (15$^{th}$ ed, Mack Publishing Company, Easton, Pa., 1975), particularly Chapter 87 by Blaug, Seymour, therein. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in the context of the methods of the present invention, provided that the VEGF antagonist is not inactivated by the formulation and the formulation is physiologically compatible and tolerable with the route of administration. See also Powell et al. PDA (1998) J Pharm Sci Technol. 52:238-311 and the citations therein for additional information related to excipients and carriers well known to pharmaceutical chemists.

Pharmaceutical formulations useful for administration by injection in the context of the present invention may be prepared by dissolving, suspending or emulsifying a VEGF antagonist in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there may be employed, e.g., sesame oil, soybean oil, etc., which may be used in combination with a solubilizing agent such as benzyl benzoate, benzyl alcohol, etc. The injection thus prepared can be filled in an appropriate ampoule if desired.

In an embodiment of the invention, the pharmaceutical formulation administered to a subject comprises aflibercept, e.g., about 40 mg/mL aflibercept, in 10 mM sodium phosphate, 40 mM sodium chloride, 0.03% polysorbate 20, and 5% sucrose, pH 6.2.

In an embodiment of the invention, the pharmaceutical formulation administered to a subject comprises a VEGF antagonist (e.g., aflibercept or conbercept, for example, 40 mg/ml thereof) and:

(a) pyrophosphate (e.g., 5 mM-250 mM). In an embodiment of the invention, the formulation further includes NaCl, sodium citrate, citric acid, mannitol and polysorbate 80, e.g., pH 5.2;

(b) a buffer such as a histidine salt such as histidine-HCl or histidine-acetate (e.g., at 10 mM to 50 mM), e.g., pH 5.7 to 6.2; a sugar such as sucrose, trehalose, mannitol, or glucose (e.g., more than 6%, but not more than 10%, for example, 2.5% to 10%); and a surfactant such as polysorbate 20 and polysorbate 80 (e.g., 0% or 0.01% to 0.03%);

(c) a histidine containing buffer such as L-histidine/histidine hydrochloride; a non-ionic surfactant such as polysorbate 20 (e.g., 0.03%), an inorganic salt such as NaCl (e.g., 40 mM), and a carbohydrate such as sucrose (e.g., 5%), e.g. pH 6.0-6.5 (e.g., 6.2 or 6.5);

(d) a buffer consisting of a histidine salt (e.g., wherein the histidine salt is histidine-HCl or histidine-acetate, for example, 10 mM to 50 mM) and having pH ranging from 5.7 to 6.2; a sugar selected from the group consisting of sucrose, trehalose, mannitol, and glucose (e.g., more than 6%, but not more than 10%); a surfactant selected from the group consisting of polysorbate 20 and polysorbate 80 (e.g., 0% to 0.1%);

(e) citric acid (e.g., 5 mM, 10 mM, 15 mM, 20 mM, 25 mM or 30 mM), sucrose (e.g., 1%, 2%, 3%, 4%, 5%, 6%, 7%, 8%, 9% or 10%), arginine (e.g., 5 mM, 10 mM, 15 mM, 20 mM, 25 mM, 30 mM, 35 mM, 40 mM, 45 mM or 50 mM or 100 mM), and polysorbate 20 (e.g., 0.01%, 0.02%, 0.03%, 0.04%, 0.05%, 0.06%, 0.07%, 0.08%, 0.09% or 0.10%);

(f) a buffer such as phosphate, histidine, acetate, succinate, citrate, glutamate, and/or lactate (e.g., at 5-20 or 5-50 mM); a non-ionic surfactant such as a polysorbate (e.g., PS20 or PS80), a polyethylene glycol dodecyl ether, a poloxamer, 4-(1,1,3,3-Tetramethylbutyl)phenyl-polyethylene glycol, an alkylsaccharide or an alkylglycoside, a tonicifying agent such as a polyol or an amino acid, for example, sucrose, trehalose, sorbitol, mannitol, glycerol, proline, arginine, methionine, glycine, or lysine, wherein the formulation has a final osmolality of about 300 mOsm/kg, and wherein the concentration of chloride anion is less than about 10 mM; pH 5.0-6.5;

(g) sodium acetate (e.g., 10-15 mM); sucrose (e.g., 7%) or trehalose (e.g., 8%); and polysorbate 20 (e.g., 0.03%), pH 5.5; or (h) any of: 10 mM sodium phosphate, 40 mM sodium chloride, 5% (w/v) sucrose, 0.03% (w/v) polysorbate 20, pH6.2; 10 mM sodium phosphate, 9% (w/v) sucrose, 0.03% (w/v) polysorbate 20, pH 6.2; 10 mM sodium phosphate, 40 mM sodium chloride, 2% (w/v) proline, 0.03% (w/v) polysorbate 20, pH6.2; 10 mM sodium phosphate, 3% (w/v) proline, 0.03% (w/v) polysorbate 20, pH 6.2; 10 mM sodium phosphate, 9% (w/v) Trehalose, 0.03% (w/v) polysorbate 20, pH 6.2; 10 mM histidine, 3% (w/v) proline, 0.03% (w/v) polysorbate 20, pH 6.2; 10 mM histidine, 9% (w/v) sucrose, 0.03% (w/v) polysorbate 20, pH 6.2; or 10 mM acetate, 9% (w/v) sucrose, 0.03% (w/v) polysorbate 20, pH 5.2.

Modes of Administration

The VEGF antagonist (or pharmaceutical formulation comprising the VEGF antagonist) may be administered to the patient by any known delivery system and/or administration method. In certain embodiments, the VEGF antagonist is administered to the patient by ocular, intraocular, intravitreal or subconjunctival injection. In other embodiments, the VEGF antagonist can be administered to the patient by topical administration, e.g., via eye drops or other liquid, gel, ointment or fluid which contains the VEGF antagonist and can be applied directly to the eye. Administration to a patient's or subject's eye refers to any acceptable method for delivering a VEGF antagonist (e.g., aflibercept) to the tissues of the eye of the patient or subject (e.g., intravitreal injection). In an embodiment of the invention, administration to the subject's or patient's eye refers to delivering a VEGF antagonist to an eye suffering an angiogenic eye disorder (e.g., as discussed herein), such as NPDR, and, optionally, to delivery to the other eye even if not so afflicted. In an embodiment of the invention, the administration is intravitreal injection using a syringe with a 30-gauge, ½-inch injection needle. For example, in an embodiment of the invention, about 50 μl is intravitreally injected to deliver about 2 mg of VEGF antagonist (e.g., aflibercept; for example, in a pharmaceutical formulation including aflibercept, e.g., about 40 mg/mL aflibercept, in 10 mM sodium phosphate, 40 mM sodium chloride, 0.03% polysorbate 20, and 5% sucrose, pH 6.2). In an embodiment of the invention, 0.5 or 2.0 mg of conbercept in a pharmaceutical formulation comprising conbercept, citric acid, sucrose, arginine and polysorbate 20 is injected into the eye.

Other possible routes of administration include, e.g., intradermal, intramuscular, intraperitoneal, intravenous, subcutaneous, intranasal, epidural, and oral. If such a route of administration is used, delivery is not to the eye, but to another tissue such as the skin, muscular tissue, peritoneum, vein, subcutis, nasal passage, dura or mouth.

Amount of VEGF Antagonist Administered

Each dose of VEGF antagonist (e.g., 0.5 mg or 2 mg, for example of aflibercept) administered to the patient's eye over the course of the treatment regimen may contain the same, or substantially the same, amount of VEGF antagonist. Alternatively, the quantity of VEGF antagonist contained within the individual doses may vary over the course of the treatment regimen. For example, in certain embodiments, a first quantity of VEGF antagonist is administered in the initial dose, a second quantity of VEGF antagonist is administered in the secondary doses, and a third quantity of VEGF antagonist is administered in the tertiary doses. The present invention contemplates dosing schemes in which the quantity of VEGF antagonist contained within the individual doses increases over time (e.g., each subsequent dose contains more VEGF antagonist than the last), decreases over time (e.g., each subsequent dose contains less VEGF antagonist than the last), initially increases then decreases, initially decreases then increases, or remains the same throughout the course of the administration regimen.

The amount of VEGF antagonist administered to the patient's eye in each dose (e.g., 0.5 mg or 2 mg, for example of aflibercept or conbercept) is, in most cases, a therapeutically effective amount. As used herein, the phrase "therapeutically effective amount" means a dose of VEGF antagonist that results in a detectable improvement in one or more symptoms or indicia of an angiogenic eye disorder, or a dose of VEGF antagonist that inhibits, prevents, lessens, or delays the progression of an angiogenic eye disorder. In the case of an anti-VEGF antibody or a VEGF receptor-based chimeric molecule such as VEGFR1R2-FcΔC1(a), a therapeutically effective amount can be from about 0.05 mg to about 5 mg, e.g., about 0.05 mg, about 0.1 mg, about 0.15 mg, about 0.2 mg, about 0.25 mg, about 0.3 mg, about 0.35 mg, about 0.4 mg, about 0.45 mg, about 0.5 mg, about 0.55 mg, about 0.6 mg, about 0.65 mg, about 0.7 mg, about 0.75 mg, about 0.8 mg, about 0.85 mg, about 0.9 mg, about 1.0 mg, about 1.05 mg, about 1.1 mg, about 1.15 mg, about 1.2 mg, about 1.25 mg, about 1.3 mg, about 1.35 mg, about 1.4 mg, about 1.45 mg, about 1.5 mg, about 1.55 mg, about 1.6 mg, about 1.65 mg, about 1.7 mg, about 1.75 mg, about 1.8 mg, about 1.85 mg, about 1.9 mg, about 2.0 mg, about 2.05 mg, about 2.1 mg, about 2.15 mg, about 2.2 mg, about 2.25 mg, about 2.3 mg, about 2.35 mg, about 2.4 mg, about 2.45 mg, about 2.5 mg, about 2.55 mg, about 2.6 mg, about 2.65 mg, about 2.7 mg, about 2.75 mg, about 2.8 mg, about 2.85 mg, about 2.9 mg, about 3.0 mg, about 3.5 mg, about 4.0 mg, about 4.5 mg, or about 5.0 mg of the antibody or receptor-based chimeric molecule.

The amount of VEGF antagonist contained within the individual doses may be expressed in terms of milligrams of antibody per kilogram of patient body weight (i.e., mg/kg). For example, the VEGF antagonist may be administered to a patient at a dose of about 0.0001 to about 10 mg/kg of patient body weight.

Treatment Population and Efficacy

The methods of the present invention are useful for treating angiogenic eye disorders in patients that have been diagnosed with or are at risk of being afflicted with an angiogenic eye disorder. Generally, the methods of the present invention demonstrate efficacy within 104 weeks of the initiation of the treatment regimen (with the initial dose administered at "week 0"), e.g., by the end of week 16, by the end of week 24, by the end of week 32, by the end of week 40, by the end of week 48, by the end of week 52, by the end of week 56, etc.

In an embodiment of the invention, in the context of methods for treating angiogenic eye disorders such as DR, PDR, NPDR, AMD, CRVO, and DME, "efficacy" means that, from the initiation of treatment, the patient exhibits:

a loss of 15 or fewer (e.g., 14, 13, 12, 11, 10, 9, 8, 7, 6, 5, 4, 3, 2 or 1) letters on the Early Treatment Diabetic Retinopathy Study (ETDRS) visual acuity chart;

a gain of one or more (e.g., 1, 2, 3, 4, 5, 6, 7, 8, 9, 10, 11 or more) letters on the ETDRS chart;

maintenance of or an improvement in DRSS score, e.g., reduction in DRSS by 2 or 3 steps;

a reduction in the incidence or the prevention of vision threatening complications (VTC) and/or blindness and/or center involved diabetic macular edema; and/or a reduction in or maintenance of central retinal thickness;

19 for example, wherein one or more of such goals are achieved within about 24 or 52 weeks of treatment initiation.

Packages

One aspect of the invention is a package, comprising:
a drug container; and
instructions for using the drug for treating or preventing diabetic retinopathy in a patient in need of such treatment, the instructions indicating a use of the drug by administering the drug to an eye of the patient,
(i) 3 monthly doses followed by one or more secondary doses every 16 weeks, wherein the first secondary dose initiates 8 weeks after the third monthly dose (week 16), or
(ii) 3 or 5 monthly doses followed by one or more secondary doses every 8 weeks; of about 2 mg of VEGF antagonist that is a VEGF receptor-based chimeric molecule.

Another aspect of the invention is a package wherein the VEGF antagonist
(i) comprises (1) a VEGFR1 component comprising amino acids 27 to 129 of SEQ ID NO:2; (2) a VEGFR2 component comprising amino acids 130-231 of SEQ ID NO:2; and (3) a multimerization component comprising amino acids 232-457 of SEQ ID NO:2;
(ii) comprises (1) an immunoglobin-like (Ig) domain 2 of a first VEGF receptor and (2) Ig domain 3 of a second VEGF receptor, and (3) a multimerizing component;
(iii) is aflibercept; or
(iv) is conbercept.

Another aspect of the invention is a package wherein the instructions indicate the drug is administered by intravitreal injection.

Another aspect of the invention is a package wherein the instructions indicate the drug is administered 3 or 5 monthly doses followed by one or more doses every 8 weeks.

Another aspect of the invention is a package wherein the instructions indicate the drug is administered 3 monthly doses followed by one or more secondary doses every 16 weeks, wherein the first secondary dose initiates 8 weeks after the third monthly dose (week 16).

Another aspect of the invention is a package wherein the instructions indicate the drug is administered one dose every 8 weeks.

An aspect of the invention is a package, comprising:
a drug container; and
instructions for using the drug for treating or preventing proliferative diabetic retinopathy in a patient in need of such treatment, the instructions indicating a use of the drug by administering the drug to an eye of the patient,
(i) 3 monthly doses followed by one or more secondary doses every 16 weeks, wherein the first secondary dose initiates 8 weeks after the third monthly dose (week 16), or
(ii) 3 or 5 monthly doses followed by one or more secondary doses every 8 weeks;
of about 2 mg of VEGF antagonist that is a VEGF receptor-based chimeric molecule.

Another aspect of the invention is a package wherein the VEGF antagonist
(i) comprises (1) a VEGFR1 component comprising amino acids 27 to 129 of SEQ ID NO:2; (2) a VEGFR2 component comprising amino acids 130-231 of SEQ ID NO:2; and (3) a multimerization component comprising amino acids 232-457 of SEQ ID NO:2;
(ii) comprises (1) an immunoglobin-like (Ig) domain 2 of a first VEGF receptor and (2) Ig domain 3 of a second VEGF receptor, and (3) a multimerizing component;
(iii) is aflibercept; or
(iv) is conbercept.

20

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

The exemplary VEGF antagonist used in all Examples set forth below is (unless otherwise indicated) a dimeric molecule having two functional VEGF binding units. Each functional binding unit is comprised of Ig domain 2 from VEGFR1 fused to Ig domain 3 from VEGFR2, which in turn is fused to the hinge region of a human IgG1 Fc domain (VEGFR1R2-FcΔC1(a); encoded by SEQ ID NO:1). This VEGF antagonist is referred to in the examples below as "VEGFT". For purposes of the following Examples, "monthly" dosing is equivalent to dosing once every four weeks.

Example 1: Phase I Clinical Trial of Intravitreally Administered VEGF Receptor-Based Chimeric Molecule (VEGFT) in Subjects with Neovascular AMD In this Phase I study, 21 subjects with neovascular AMD received a single intravitreal (IVT) dose of VEGFT. Five groups of three subjects each received either 0.05, 0.15, 0.5, 2 or 4 mg of VEGFT, and a sixth group of six subjects received 1 mg. No serious adverse events related to the study drug, and no identifiable intraocular inflammation was reported. Preliminary results showed that, following injection of VEGFT, a rapid decrease in foveal thickness and macular volume was observed that was maintained through 6 weeks. At Day 43 across all dose groups, mean excess retinal thickness [excess retinal thickness=(retinal thickness−179μ)] on optical coherence tomography (OCT) was reduced from 119μ to 27μ as assessed by Fast Macular Scan and from 194μ to 60μ as assessed using a single Posterior Pole scan. The mean increase in best corrected visual acuity (BCVA) was 4.75 letters, and BCVA was stable or improved in 95% of subjects. In the 2 highest dose groups (2 and 4 mg), the mean increase in BCVA was 13.5 letters, with 3 of 6 subjects demonstrating improvement of 3 lines.

Example 2: Phase II Clinical Trial of Repeated Doses of Intravitreally Administered VEGF Receptor-Based Chimeric Molecule (VEGFT) in Subjects with Neovascular AMD This study was a double-masked, randomized study of 3 doses (0.5, 2, and 4 mg) of VEGFT tested at 4-week and/or 12-week dosing intervals. There were 5 treatment arms in this study, as follows: 1) 0.5 mg every 4 weeks, 2) 0.5 mg every 12 weeks, 3) 2 mg every 4 weeks, 4) 2 mg every 12 weeks and 5) 4 mg every 12 weeks. Subjects were dosed at a fixed interval for the first 12 weeks, after which they were evaluated every 4 weeks for 9 months, during which additional doses were administered based on pre-specified criteria. All subjects were then followed for one year after their last dose of VEGFT. Preliminary data from a pre-planned interim analysis indicated that VEGFT met its primary endpoint of a statistically significant reduction in retinal thickness after 12 weeks compared with baseline (all groups combined, decrease of 135μ, p<0.0001). Mean change from baseline in visual acuity, a key secondary endpoint of the study, also demonstrated statistically significant improvement (all groups combined, increase of 5.9 letters, p<0.0001). Moreover, patients in the dose groups that received only a single dose, on average, demonstrated a decrease in excess retinal thickness (p<0.0001) and an increase in visual acuity (p=0.012) at 12 weeks. There were no drug-related serious adverse events, and treatment with the VEGF antagonists was generally well-tolerated. The most common adverse events were those typically associated with intravitreal injections.

Example 3: Phase I Clinical Trial of Systemically Administered VEGF Receptor-Based Chimeric Molecule (VEGFT) in Subjects with Neovascular AMD This study was a placebo-controlled, sequential-group, dose-escalating safety, tolerability and bioeffect study of VEGFT by IV infusion in subjects with neovascular AMD. Groups of 8 subjects meeting eligibility criteria for subfoveal choroidal neovascularization (CNV) related to AMD were assigned to receive 4 IV injections of VEGFT or placebo at dose levels of 0.3, 1, or 3 mg/kg over an 8-week period.

Most adverse events that were attributed to VEGFT were mild to moderate in severity, but 2 of 5 subjects treated with 3 mg/kg experienced dose-limiting toxicity (DLT) (one with Grade 4 hypertension and one with Grade 2 proteinuria); therefore, all subjects in the 3 mg/kg dose group did not enter the study. The mean percent changes in excess retinal thickness were: −12%, −10%, −66%, and −60% for the placebo, 0.3, 1, and 3 mg/kg dose groups at day 15 (ANOVA p<0.02), and −5.6%, +47.1%, and −63.3% for the placebo, 0.3, and 1 mg/kg dose groups at day 71 (ANOVA p<0.02). There was a numerical improvement in BCVA in the subjects treated with VEGFT. As would be expected in such a small study, the results were not statistically significant.

Example 4: Phase III Clinical Trials of the Efficacy, Safety, and Tolerability of Repeated Doses of Intravitreal VEGFT in Subjects with Neovascular Age-Related Macular Degeneration A. Objectives, Hypotheses and Endpoints Two parallel Phase III clinical trials were carried out to investigate the use of VEGFT to treat patients with the neovascular form of age-related macular degeneration (Study 1 and Study 2). The primary objective of these studies was to assess the efficacy of IVT administered VEGFT compared to ranibizumab (Lucentis®, Genentech, Inc.), in a non-inferiority paradigm, in preventing moderate vision loss in subjects with all subtypes of neovascular AMD.

The secondary objectives were (a) to assess the safety and tolerability of repeated IVT administration of VEGFT in subjects with all sub-types of neovascular AMD for periods up to 2 years; and (b) to assess the effect of repeated IVT administration of VEGFT on Vision-Related Quality of Life (QOL) in subjects with all sub-types of neovascular AMD.

The primary hypothesis of these studies was that the proportion of subjects treated with VEGFT with stable or improved BCVA (<15 letters lost) is similar to the proportion treated with ranibizumab who have stable or improved BCVA, thereby demonstrating non-inferiority.

The primary endpoint for these studies was the prevention of vision loss of greater than or equal to 15 letters on the ETDRS chart, compared to baseline, at 52 weeks. Secondary endpoints were as follows: (a) change from baseline to Week 52 in letter score on the ETDRS chart; (b) gain from baseline to Week 52 of 15 letters or more on the ETDRS chart; (c) change from baseline to Week 52 in total NEI VFQ-25 score; and (d) change from baseline to Week 52 in CNV area.

B. Study Design

For each study, subjects were randomly assigned in a 1:1:1:1 ratio to 1 of 4 dosing regimens: (1) 2 mg VEGFT administered every 4 weeks (2Q4); (2) 0.5 mg VEGFT administered every 4 weeks (0.5Q4); (3) 2 mg VEGFT administered every 4 weeks to week 8 and then every 8 weeks (with sham injection at the interim 4-week visits when study drug was not administered (2Q8); and (4) 0.5 mg ranibizumab administered every 4 weeks (RQ4). Subjects assigned to (2Q8) received the 2 mg injection every 4 weeks to week 8 and then a sham injection at interim 4-week visits (when study drug is not to be administered) during the first 52 weeks of the studies. (No sham injection were given at Week 52).

The study duration for each subject was scheduled to be 96 weeks plus the recruitment period. For the first 52 weeks (Year 1), subjects received an IVT or sham injection in the study eye every 4 weeks. (No sham injections were given at Week 52). During the second year of the study, subjects will be evaluated every 4 weeks and will receive IVT injection of study drug at intervals determined by specific dosing criteria, but at least every 12 weeks. (During the second year of the study, sham injections will not be given.) During this period, injections may be given as frequently as every 4 weeks, but no less frequently than every 12 weeks, according to the following criteria: (i) increase in central retinal thickness of ≥100 μm compared to the lowest previous value as measured by optical coherence tomography (OCT); or (ii) a loss from the best previous letter score of at least 5 ETDRS letters in conjunction with recurrent fluid as indicated by OCT; or (iii) new or persistent fluid as indicated by OCT; or (iv) new onset classic neovascularization, or new or persistent leak on fluorescein angiography (FA); or (v) new macular hemorrhage; or (vi) 12 weeks have elapsed since the previous injection. According to the present protocol, subjects must receive an injection at least every 12 weeks.

Subjects were evaluated at 4 weeks intervals for safety and best corrected visual acuity (BCVA) using the 4 meter ETDRS protocol. Quality of Life (QOL) was evaluated using the NEI VFQ-25 questionnaire. OCT and FA examinations were conducted periodically.

Approximately 1200 subjects were enrolled, with a target enrollment of 300 subjects per treatment arm.

To be eligible for this study, subjects were required to have subfoveal choroidal neovascularization (CNV) secondary to AMD. "Subfoveal" CNV was defined as the presence of subfoveal neovascularization, documented by FA, or presence of a lesion that is juxtafoveal in location angiographically but affects the fovea. Subject eligibility was confirmed based on angiographic criteria prior to randomization.

Only one eye was designated as the study eye. For subjects who met eligibility criteria in both eyes, the eye with the worse VA was selected as the study eye. If both eyes had equal VA, the eye with the clearest lens and ocular media and least amount of subfoveal scar or geographic atrophy was selected. If there was no objective basis for selecting the study eye, factors such as ocular dominance, other ocular pathology and subject preference were considered in making the selection.

Inclusion criteria for both studies were as follows: (i) signed Informed consent; (ii) at least 50 years of age; (iii) active primary subfoveal CNV lesions secondary to AMD, including juxtafoveal lesions that affect the fovea as evidenced by FA in the study eye; (iv) CNV at least 50% of total lesion size; (v) early treatment diabetic retinopathy study (ETDRS) best-corrected visual acuity of: 20/40 to 20/320 (letter score of 73 to 25) in the study eye; (vi) willing, committed, and able to return for all clinic visits and complete all study-related procedures; and (vii) able to read, understand and willing to sign the informed consent form (or, if unable to read due to visual impairment, be read to verbatim by the person administering the informed consent or a family member).

Exclusion criteria for both studies were as follows: 1. Any prior ocular (in the study eye) or systemic treatment or surgery for neovascular AMD except dietary supplements or vitamins. 2. Any prior or concomitant therapy with another investigational agent to treat neovascular AMD in the study eye, except dietary supplements or vitamins. 3. Prior treatment with anti-VEGF agents as follows: (a) Prior treatment with anti-VEGF therapy in the study eye was not allowed; (b) Prior treatment with anti-VEGF therapy in the fellow eye with an investigational agent (not FDA approved, e.g. bevacizumab) was allowed up to 3 months prior to first dose in the study, and such treatments were not allowed during the study. Prior treatment with an approved anti-VEGF therapy in the fellow eye was allowed; (c) Prior systemic anti-VEGF therapy, investigational or FDA/Health Canada approved, was only allowed up to 3 months prior to first dose, and was not allowed during the study. 4. Total lesion size >12 disc areas (30.5 mm2, including blood, scars and neovascularization) as assessed by FA in the study eye. 5. Subretinal hemorrhage that is either 50% or more of the total lesion area, or if the blood is under the fovea and is 1 or more disc areas in size in the study eye. (If the blood is under the fovea, then the fovea must be surrounded 270 degrees by visible CNV.) 6. Scar or fibrosis, making up >50% of total lesion in the study eye. 7. Scar, fibrosis, or atrophy involving the center of the fovea. 8. Presence of retinal pigment epithelial tears or rips involving the macula in the study eye. 9. History of any vitreous hemorrhage within 4 weeks prior to Visit 1 in the study eye. 10. Presence of other causes of CNV, including pathologic myopia (spherical equivalent of −8 diopters or more negative, or axial length of 25 mm or more), ocular histoplasmosis syndrome, angioid streaks, choroidal rupture, or multifocal choroiditis in the study eye. 11. History or clinical evidence of diabetic retinopathy, diabetic macular edema or any other vascular disease affecting the retina, other than AMD, in either eye. 12. Prior vitrectomy in the study eye. 13. History of retinal detachment or treatment or surgery for retinal detachment in the study eye. 14. Any history of macular hole of stage 2 and above in the study eye. 15. Any intraocular or periocular surgery within 3 months of Day 1 on the study eye, except lid surgery, which may not have taken place within 1 month of day 1, as long as it was unlikely to interfere with the injection. 16. Prior trabeculectomy or other filtration surgery in the study eye. 17. Uncontrolled glaucoma (defined as intraocular pressure greater than or equal to 25 mm Hg despite treatment with anti-glaucoma medication) in the study eye. 18. Active intraocular inflammation in either eye. 19. Active ocular or periocular infection in either eye. 20. Any ocular or periocular infection within the last 2 weeks prior to Screening in either eye. 21. Any history of uveitis in either eye. 22. Active scleritis or episcleritis in either eye. 23. Presence or history of scleromalacia in either eye. 24. Aphakia or pseudophakia with absence of posterior capsule (unless it occurred as a result of a yttrium aluminum garnet [YAG] posterior capsulotomy) in the study eye. 25. Previous therapeutic radiation in the region of the study eye. 26. History of corneal transplant or corneal dystrophy in the study eye. 27. Significant media opacities, including cataract, in the study eye which might interfere with visual acuity, assessment of safety, or fundus photography. 28. Any concurrent intraocular condition in the study eye (e.g. cataract) that, in the opinion of the investigator, could require either medical or surgical intervention during the 96 week study period. 29. Any concurrent ocular condition in the study eye which, in the opinion of the investigator, could either increase the risk to the subject beyond what is to be expected from standard procedures of intraocular injection, or which otherwise may interfere with the injection procedure or with evaluation of efficacy or safety. 30. History of other disease, metabolic dysfunction, physical examination finding, or clinical laboratory finding giving reasonable suspicion of a disease or condition that contraindicates the use of an investigational drug or that might affect interpretation of the results of the study or render the subject at high risk for treatment complications. 31. Participation as a subject in any clinical study within the 12 weeks prior to Day 1. 32. Any systemic or ocular treatment with an investigational agent in the past 3 months prior to Day 1. 33. The use of long acting steroids, either systemically or intraocularly, in the 6 months prior to day 1. 34. Any history of allergy to povidone iodine. 35. Known serious allergy to the fluorescein sodium for injection in angiography. 36. Presence of any contraindications indicated in the FDA Approved label for ranibizumab (Lucentis®). 37. Females who were pregnant, breastfeeding, or of childbearing potential, unwilling to practice adequate contraception throughout the study. Adequate contraceptive measures include oral contraceptives (stable use for 2 or more cycles prior to screening); IUD; Depo-Provera®; Norplant® System implants; bilateral tubal ligation; vasectomy; condom or diaphragm plus either contraceptive sponge, foam or jelly.

Subjects were not allowed to receive any standard or investigational agents for treatment of their AMD in the study eye other than their assigned study treatment with VEGFT or ranibizumab as specified in the protocol until they completed the Completion/Early Termination visit assessments. This includes medications administered locally (e.g., IVT, topical, juxtascleral or periorbital routes), as well as those administered systemically with the intent of treating the study and/or fellow eye.

The study procedures are summarized as follows:

Best Corrected Visual Acuity: Visual function of the study eye and the fellow eye were assessed using the ETDRS protocol (The Early Treatment Diabetic Retinopathy Study Group) at 4 meters. Visual Acuity examiners were certified to ensure consistent measurement of BCVA. The VA examiners were required to remain masked to treatment assignment.

Optical Coherence Tomography: Retinal and lesion characteristics were evaluated using OCT on the study eye. At the Screen Visit (Visit 1) images were captured and transmitted for both eyes. All OCT images were captured using the Zeiss Stratus OCT™ with software Version 3 or greater.

OCT images were sent to an independent reading center where images were read by masked readers at visits where OCTs were required. All OCTs were electronically archived at the site as part of the source documentation. A subset of OCT images were read. OCT technicians were required to be certified by the reading center to ensure consistency and quality in image acquisition. Adequate efforts were made to ensure that OCT technicians at the site remained masked to treatment assignment.

Fundus Photography and Fluorescein Angiography (FA): The anatomical state of the retinal vasculature of the study eye was evaluated by funduscopic examination, fundus photography and FA. At the Screen Visit (Visit 1) funduscopic examination, fundus photography and FA were captured and transmitted for both eyes. Fundus and angiographic images were sent to an independent reading center where images were read by masked readers. The reading center confirmed subject eligibility based on angiographic criteria prior to randomization. All FAs and fundus photographs were archived at the site as part of the source documentation. Photographers were required to be certified by the reading center to ensure consistency and quality in image acquisition. Adequate efforts were made to ensure that all photographers at the site remain masked to treatment assignment.

Vision-Related Quality of Life: Vision-related QOL was assessed using the National Eye Institute 25-Item Visual Function Questionnaire (NEI VFQ-25) in the interviewer-administered format. NEI VFQ-25 was administered by certified personnel at a contracted call center. At the screening visit, the sites assisted the subject and initiated the first call to the call center to collect all of the subject's contact information and to complete the first NEI VFQ-25 on the phone prior to randomization and IVT injection. For all subsequent visits, the call center called the subject on the phone, prior to IVT injection, to complete the questionnaire.

Intraocular Pressure: Intraocular pressure (IOP) of the study eye was measured using applanation tonometry or Tonopen. The same method of IOP measurement was used in each subject throughout the study.

C. Results Summary (52 Week Data)

The primary endpoint (prevention of moderate or severe vision loss as defined above) was met for all three VEGFT groups (2Q4, 0.5Q4 and 2Q8) in this study. The results from both studies are summarized in Table 1.

In Study 1, patients receiving VEGFT 2 mg monthly (2Q4) achieved a statistically significant greater mean improvement in visual acuity at week 52 versus baseline (secondary endpoint), compared to ranibizumab 0.5 mg monthly (RQ4); patients receiving VEGFT 2 mg monthly on average gained 10.9 letters, compared to a mean 8.1 letter gain with ranibizumab 0.5 mg dosed every month ($p<0.01$). All other dose groups of VEGFT in Study 1 and all dose groups in Study 2 were not statistically different from ranibizumab in this secondary endpoint.

A generally favorable safety profile was observed for both VEGFT and ranibizumab. The incidence of ocular treatment emergent adverse events was balanced across all four treatment groups in both studies, with the most frequent events associated with the injection procedure, the underlying disease, and/or the aging process. The most frequent ocular adverse events were conjunctival hemorrhage, macular degeneration, eye pain, retinal hemorrhage, and vitreous floaters. The most frequent serious non-ocular adverse events were typical of those reported in this elderly population who receive intravitreal treatment for wet AMD; the most frequently reported events were falls, pneumonia, myocardial infarction, atrial fibrillation, breast cancer, and acute coronary syndrome. There were no notable differences among the study arms.

Example 5: Phase II Clinical Trial of VEGFT in Subjects with Diabetic Macular Edema (DME)

In this study, 221 patients with clinically significant DME with central macular involvement were randomized, and 219 patients were treated with balanced distribution over five groups. The control group received macular laser therapy at baseline, and patients were eligible for repeat laser treatments, but no more frequently than at 16 week intervals. The remaining four groups received VEGFT by intravitreal injection as follows: Two groups received 0.5 or 2 mg of VEGFT once every four weeks throughout the 12-month dosing period (0.5Q4 and 2Q4, respectively). Two groups received three initial doses of 2 mg VEGFT once every four weeks (i.e., at baseline, and weeks 4 and 8), followed through week 52 by either once every 8 weeks dosing (2Q8) or as needed dosing with very strict repeat dosing criteria (PRN). Mean gains in visual acuity versus baseline were as shown in Table 2:

TABLE 1

| | Ranibizumab 0.5 mg monthly (RQ4) | VEGFT 0.5 mg monthly (0.5Q4) | VEGFT 2 mg monthly (2Q4) | VEGFT 2 mg every 8 weeks[a] (2Q8) |
|---|---|---|---|---|
| Maintenance of vision* (% patients losing <15 letters) at week 52 versus baseline | | | | |
| Study 1 | 94.4% | 95.9%** | 95.1%** | 95.1%** |
| Study 2 | 94.4% | 96.3%** | 95.6%** | 95.6%** |
| Mean improvement in vision* (letters) at 52 weeks versus baseline (p-value vs RQ4)*** | | | | |
| Study 1 | 8.1 | 6.9 (NS) | 10.9 ($p<0.01$) | 7.9 (NS) |
| Study 2 | 9.4 | 9.7 (NS) | 7.6 (NS) | 8.9 (NS |

[a]Following three initial monthly doses
*Visual acuity was measured as the total number of letters read correctly on the Early Treatment Diabetic Retinopathy Study (ETDRS) eye chart.
**Statistically non-inferior based on a non-inferiority margin of 10%, using confidence interval approach (95.1% and 95% for Study 1 and Study 2, respectively)
***Test for superiority
NS = non-significant

TABLE 2

| | n | Mean change in visual acuity at week 24 versus baseline (letters) | Mean change in visual acuity at week 52 versus baseline (letters) |
|---|---|---|---|
| Laser | 44 | 2.5 | −1.3 |
| VEGFT 0.5 mg monthly (0.5Q4) | 44 | 8.6** | 11.0** |
| VEGFT 2 mg monthly (2Q4) | 44 | 11.4** | 13.1** |
| VEGFT 2 mg every 8 weeks[a] (2Q8) | 42 | 8.5** | 9.7** |
| VEGFT 2 mg as needed[a] (PRN) | 45 | 10.3** | 12.0** |

[a]Following three initial monthly doses
**$p<0.01$ versus laser

In this study, the visual acuity gains achieved with VEGFT administration at week 24 were maintained or numerically improved up to completion of the study at week 52 in all VEGFT study groups, including 2 mg dosed every other month.

As demonstrated in the foregoing Examples, the administration of VEGFT to patients suffering from angiogenic eye disorders (e.g., AMD and DME) at a frequency of once every 8 weeks, following a single initial dose and two secondary doses administered four weeks apart, resulted in significant prevention of moderate or severe vision loss or improvements in visual acuity.

Example 6: A Randomized, Multicenter, Double-Masked Trial in Treatment Naïve Patients with Macular Edema Secondary to CRVO In this randomized, double-masked, Phase 3 study, patients received 6 monthly injections of either 2 mg intravitreal VEGFT (114 patients) or sham injections (73 patients). From Week 24 to Week 52, all patients received 2 mg VEGFT as-needed (PRN) according to retreatment criteria. Thus, "sham-treated patients" means patients who received sham injections once every four weeks from Week 0 through Week 20, followed by intravitreal VEGFT as needed from Week 24 through Week 52. "VEGFT-treated patients" means patients who received VEGFT intravitreal injections once every four weeks from Week 0 through Week 20, followed by intravitreal VEGFT as needed from Week 24 through Week 52. The primary endpoint was the proportion of patients who gained ≥15 ETDRS letters from baseline at Week 24. Secondary visual, anatomic, and Quality of Life NEI VFQ-25 outcomes at Weeks 24 and 52 were also evaluated.

At Week 24, 56.1% of VEGFT-treated patients gained ETDRS letters from baseline vs 12.3% of sham-treated patients (P<0.0001). Similarly, at Week 52, 55.3% of VEGFT-treated patients gained letters vs 30.1% of sham-treated patients (P<0.01). At Week 52, VEGFT-treated patients gained a mean of 16.2 letters vs 3.8 letters for sham-treated patients (P<0.001). Mean number of injections was 2.7 for VEGFT-treated patients vs 3.9 for sham-treated patients. Mean change in central retinal thickness was −413.0 µm for VEGFT-treated patients vs −381.8 µm for sham-treated patients. The proportion of patients with ocular neovascularization at Week 24 were 0% for VEGFT-treated patients and 6.8% for sham-treated patients, respectively; at Week 52 after receiving VEGFT PRN, proportions were 0% and 6.8% for VEGFT-treated and sham-treated. At Week 24, the mean change from baseline in the VFQ-25 total score was 7.2 vs 0.7 for the VEGFT-treated and sham-treated groups; at Week 52, the scores were 7.5 vs 5.1 for the VEGFT-treated and sham-treated groups.

This Example confirms that dosing monthly with 2 mg intravitreal VEGFT injection resulted in a statistically significant improvement in visual acuity at Week 24 that was maintained through Week 52 with PRN dosing compared with sham PRN treatment. VEGFT was generally well tolerated and had a generally favorable safety profile.

Example 7: Dosing Regimens

Specific, non-limiting examples of dosing regimens within the scope of the present invention are as follows:

VEGFT 2 mg (0.05 mL) administered by intravitreal injection once every 4 weeks (monthly).

VEGFT 2 mg (0.5 mL) administered by intravitreal injection once every 4 weeks for the first 8 weeks, followed by 2 mg (0.05 mL) via intravitreal injection once every 8 weeks.

VEGFT 2 mg (0.5 mL) administered by intravitreal injection once every 4 weeks for the first 8 weeks, followed by 2 mg (0.05 mL) via intravitreal injection on a less frequent basis based on visual and/or anatomical outcomes (as assessed by a physician or other qualified medical professional).

VEGFT 2 mg (0.5 mL) administered by intravitreal injection once every 4 weeks for the first 8 weeks, followed by 2 mg (0.05 mL) via intravitreal injection administered pro re nata (PRN) based on visual and/or anatomical outcomes (as assessed by a physician or other qualified medical professional).

VEGFT 2 mg (0.5 mL) administered by intravitreal injection once every 4 weeks for the first 12 weeks, followed by 2 mg (0.05 mL) via intravitreal injection once every 8 weeks.

VEGFT 2 mg (0.5 mL) administered by intravitreal injection once every 4 weeks for the first 12 weeks, followed by 2 mg (0.05 mL) via intravitreal injection on a less frequent basis based on visual and/or anatomical outcomes (as assessed by a physician or other qualified medical professional).

VEGFT 2 mg (0.5 mL) administered by intravitreal injection once every 4 weeks for the first 12 weeks, followed by 2 mg (0.05 mL) via intravitreal injection administered pro re nata (PRN) based on visual and/or anatomical outcomes (as assessed by a physician or other qualified medical professional).

VEGFT 2 mg (0.5 mL) administered by intravitreal injection once every 4 weeks for the first 16 weeks, followed by 2 mg (0.05 mL) via intravitreal injection once every 8 weeks.

VEGFT 2 mg (0.5 mL) administered by intravitreal injection once every 4 weeks for the first 16 weeks, followed by 2 mg (0.05 mL) via intravitreal injection on a less frequent basis based on visual and/or anatomical outcomes (as assessed by a physician or other qualified medical professional).

VEGFT 2 mg (0.5 mL) administered by intravitreal injection once every 4 weeks for the first 16 weeks, followed by 2 mg (0.05 mL) via intravitreal injection administered pro re nata (PRN) based on visual and/or anatomical outcomes (as assessed by a physician or other qualified medical professional).

VEGFT 2 mg (0.5 mL) administered by intravitreal injection once every 4 weeks for the first 20 weeks, followed by 2 mg (0.05 mL) via intravitreal injection once every 8 weeks.

VEGFT 2 mg (0.5 mL) administered by intravitreal injection once every 4 weeks for the first 20 weeks, followed by 2 mg (0.05 mL) via intravitreal injection on a less frequent basis based on visual and/or anatomical outcomes (as assessed by a physician or other qualified medical professional).

VEGFT 2 mg (0.5 mL) administered by intravitreal injection once every 4 weeks for the first 20 weeks, followed by 2 mg (0.05 mL) via intravitreal injection administered pro re nata (PRN) based on visual and/or anatomical outcomes (as assessed by a physician or other qualified medical professional).

VEGFT 2 mg (0.5 mL) administered by intravitreal injection once every 4 weeks for the first 24 weeks, followed by 2 mg (0.05 mL) via intravitreal injection once every 8 weeks.

VEGFT 2 mg (0.5 mL) administered by intravitreal injection once every 4 weeks for the first 24 weeks, followed by 2 mg (0.05 mL) via intravitreal injection on a less frequent basis based on visual and/or anatomical outcomes (as assessed by a physician or other qualified medical professional).

VEGFT 2 mg (0.5 mL) administered by intravitreal injection once every 4 weeks for the first 24 weeks, followed by 2 mg (0.05 mL) via intravitreal injection administered pro re nata (PRN) based on visual and/or anatomical outcomes (as assessed by a physician or other qualified medical professional).

VEGFT 2 mg (0.5 mL) administered by intravitreal injection once every 4 weeks for the first 28 weeks, followed by 2 mg (0.05 mL) via intravitreal injection once every 8 weeks.

VEGFT 2 mg (0.5 mL) administered by intravitreal injection once every 4 weeks for the first 28 weeks, followed by 2 mg (0.05 mL) via intravitreal injection on a less frequent basis based on visual and/or anatomical outcomes (as assessed by a physician or other qualified medical professional).

VEGFT 2 mg (0.5 mL) administered by intravitreal injection once every 4 weeks for the first 28 weeks, followed by 2 mg (0.05 mL) via intravitreal injection administered pro re nata (PRN) based on visual and/or anatomical outcomes (as assessed by a physician or other qualified medical professional).

VEGFT 2 mg (0.05 mL) administered by intravitreal injection as a single initial dose, followed by additional doses administered pro re nata (PRN) based on visual and/or anatomical outcomes (as assessed by a physician or other qualified medical professional).

Variations on the above-described dosing regimens would be appreciated by persons of ordinary skill in the art and are also within the scope of the present invention. For example, the amount of VEGFT and/or volume of formulation administered to a patient may be varied based on patient characteristics, severity of disease, and other diagnostic assessments by a physician or other qualified medical professional.

Any of the foregoing administration regimens may be used for the treatment of, e.g., age-related macular degeneration (e.g., wet AMD, exudative AMD, etc.), retinal vein occlusion (RVO), central retinal vein occlusion (CRVO; e.g., macular edema following CRVO), branch retinal vein occlusion (BRVO), diabetic macular edema (DME), choroidal neovascularization (CNV; e.g., myopic CNV), iris neovascularization, neovascular glaucoma, post-surgical fibrosis in glaucoma, proliferative vitreoretinopathy (PVR), optic disc neovascularization, corneal neovascularization, retinal neovascularization, vitreal neovascularization, pannus, pterygium, vascular retinopathy, etc.

Example 8: Phase 3, Double-Masked, Randomized Study of the Efficacy and Safety of Intravitreal IAI in Patients with Moderately Severe to Severe NPDR (PANORAMA)-Week 24 and 52 Results This was a phase 3, double-masked, randomized study of the efficacy and safety of IVT (intravitreal injection) aflibercept (IAI) for the improvement of moderately severe to severe non-proliferative diabetic retinopathy (NPDR). These data relate to results achieved after 24 weeks and 52 weeks.

Eligible patients were enrolled into 1 of 3 treatment groups in a 1:1:1 randomization scheme, and are stratified based on their Diabetic Retinopathy Severity Scale (DRSS) score (level 47 vs. level 53) (see FIG. 5 and FIG. 6). Only 1 eye was selected as the study eye.

Study Design

The primary outcome measure of the study is the proportion of patients who improved by steps from baseline on the DRSS in the combined 2Q8 and 2Q16 groups at week 24, and in each group separately at week 52.

Patients are evaluated for efficacy (best corrected visual acuity [BCVA] using the 4-meter Early Treatment Diabetic Retinopathy Study [ETDRS] protocol, spectral domain optical coherence tomography [SD OCT], and fluorescein angiography [FA]/fundus photography [FP]) and for ocular and systemic safety (including ophthalmic exams, visual field testing, and laboratory assessments) through week 100.

The secondary outcome measures are also tested at week 52 and are as follows:
(1) Proportion of patients developing a vision threatening complication (VTC) due to diabetic retinopathy through week 52. Vision threatening complications are defined as composite outcome of PDR (inclusive of patients who have vitreous hemorrhage or tractional retinal detachment believed to be due to PDR) and ASNV. ASNV is defined as neovascularization of the iris (at least 2 cumulative clock hours), and/or definitive neovascularization of the iridocorneal angle
(2) Proportion of patients who develop CI DME through week 52
(3) Time to development of a vision threatening complication through week 52
(4) Time to development of CI DME (center-involved DME) through week 52
(5) Proportion of patients who receive PRP (panretinal photocoagulation) through week 52, inclusive of patients undergoing vitrectomy with endolaser
(6) Area under the curve (AUC) for change in BCVA from baseline at week 52.

Study Timeline
Day −21 to −1: Screening visit (visit 1)
Day 1: Baseline visit (visit 2)
Week 24: Primary Outcome Measure (2Q8 & 2Q16 combined) (visit 7)
Week 52: Primary Outcome Measure (2Q8 & 2Q16 separately) and all secondary outcome measures (visit 11)
Week 100: End of Study (visit 18)

Exclusion criteria: Patients who met any of the following criteria at either the screening visit or at day 1 were excluded from the study:
(1) Presence of DME threatening the center of the macula (within 1,000 microns of the foveal center) in the study eye;
(2) Evidence of retinal neovascularization on clinical examination or FA (fluorescein angiography);
(3) Any prior focal or grid laser photocoagulation (within 1,000 microns of the foveal center) or any prior PRP in the study eye;
(4) Any prior systemic anti-VEGF treatment or IVT anti-VEGF treatment in the study eye;
(5) Any prior intraocular steroid in the study eye; periocular steroid in the study eye within 120 days of day 1;
(6) History of vitreoretinal surgery in the study eye;
(7) Intraocular pressure (IOP) 25 mm Hg in the study eye;
(8) Evidence of active infectious blepharitis, keratitis, scleritis, or conjunctivitis in either eye;
(9) Any intraocular inflammation or infection in either eye within 3 months of the screening visit;
(10) Current ASNV, vitreous hemorrhage, or tractional retinal detachment visible at the screening assessments in the study eye;
(11) Ocular media of insufficient quality to obtain fundus and optical coherence tomography (OCT) images in the study eye; allergy to fluorescein precluding ability to perform fluorescein angiography;

(12) Hemoglobin A1c (HbA1c) >12%, or if HbA1c is ≤12')/0, diabetes mellitus is uncontrolled in the opinion of the investigator;

(13) Uncontrolled blood pressure (defined as systolic >160 mm Hg or diastolic >95 mm Hg while patient is sitting);

(14) History of cerebrovascular accident or myocardial infarction within 180 days of day 1;

(15) Renal failure, dialysis, or history of renal transplant;

(16) Women who are breastfeeding or who have a positive serum hCG/urine pregnancy test at the screening or baseline visit;

(17) Any concurrent ocular condition in the study eye which, in the opinion of the investigator, could either increase the risk to the patient beyond what is to be expected from standard procedures of IVT injections, or which otherwise may interfere with the injection procedure or with evaluation of efficacy or safety;

(18) History of other disease, metabolic dysfunction, physical examination finding, or clinical laboratory finding giving reasonable suspicion of a disease or condition that contraindicates the use of an investigational drug or that might affect interpretation of the results of the study or render the patient at high risk for treatment complications;

(19) Participation as a patient in any interventional clinical study within the 12 weeks prior to day 1 of the study;

(20) Sexually active men* or women of childbearing potential** who are unwilling to practice adequate contraception prior to the initial dose/start of the first treatment, during the study, and for at least 3 months after the last dose. Adequate contraceptive measures include stable use of oral contraceptives or other prescription pharmaceutical contraceptives for 2 or more menstrual cycles prior to screening; intrauterine device; bilateral tubal ligation; vasectomy; condom plus contraceptive sponge, foam, or jelly, or diaphragm plus contraceptive sponge, foam, or jelly.

*Contraception is not required for men with documented vasectomy.

**Postmenopausal women must be amenorrheic for at least 12 months in order not to be considered of childbearing potential. Pregnancy testing and contraception are not required for women with documented hysterectomy or tubal ligation.

(21) Patients who are on systemic anti-VEGF treatment (i.e., bevacizumab, ziv-aflibercept) for oncology treatment (if a patient requires systemic anti-VEGF treatment during the study, the patient will be withdrawn)

Treatment regimen: The 3 treatment groups have the following dosing regimens scheduled from day 1 to week 48:

2Q8: aflibercept 2 mg Q8 to week 48 (after 5 initial monthly doses), followed by a flexible treatment regimen with aflibercept 2 mg after week 52;

2Q16: aflibercept 2 mg Q16 to week 96 (after 3 initial monthly doses and 1 Q8 interval);

Sham: sham injections every 4 weeks (Q4) to week 16, followed by sham injections Q8 to week 96.

Data herein may refer to the 2Q16 dosing group as "Group 1"; the 2Q8 dosing group as "Group 2" and the sham group as "Sham".

Figure 3:
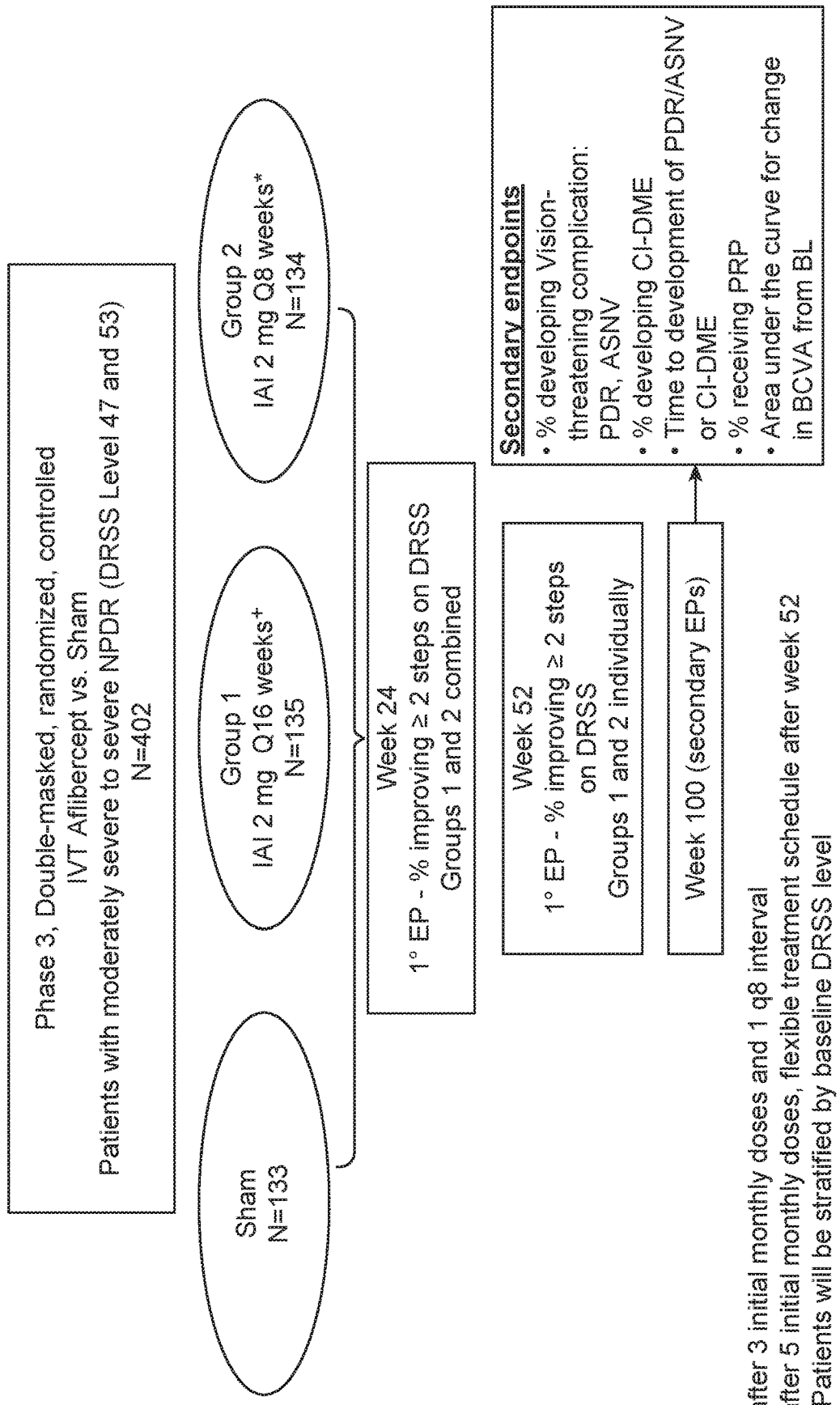
FIG. 3 summarizes the phase 3, double-masked, randomized, controlled PANORAMA study design. Patients with moderately severe to severe NPDR received (i) a sham injection ("sham"), (ii) 3 monthly doses followed by one or more secondary doses every 16 weeks, wherein the first secondary dose initiates 8 weeks after the third monthly dose (week 16) ("Group 1"), or (iii) 5 monthly doses followed by one or more secondary doses every 8 weeks ("Group 2").

See FIG. 3 and FIG. 4.

Figure 7:
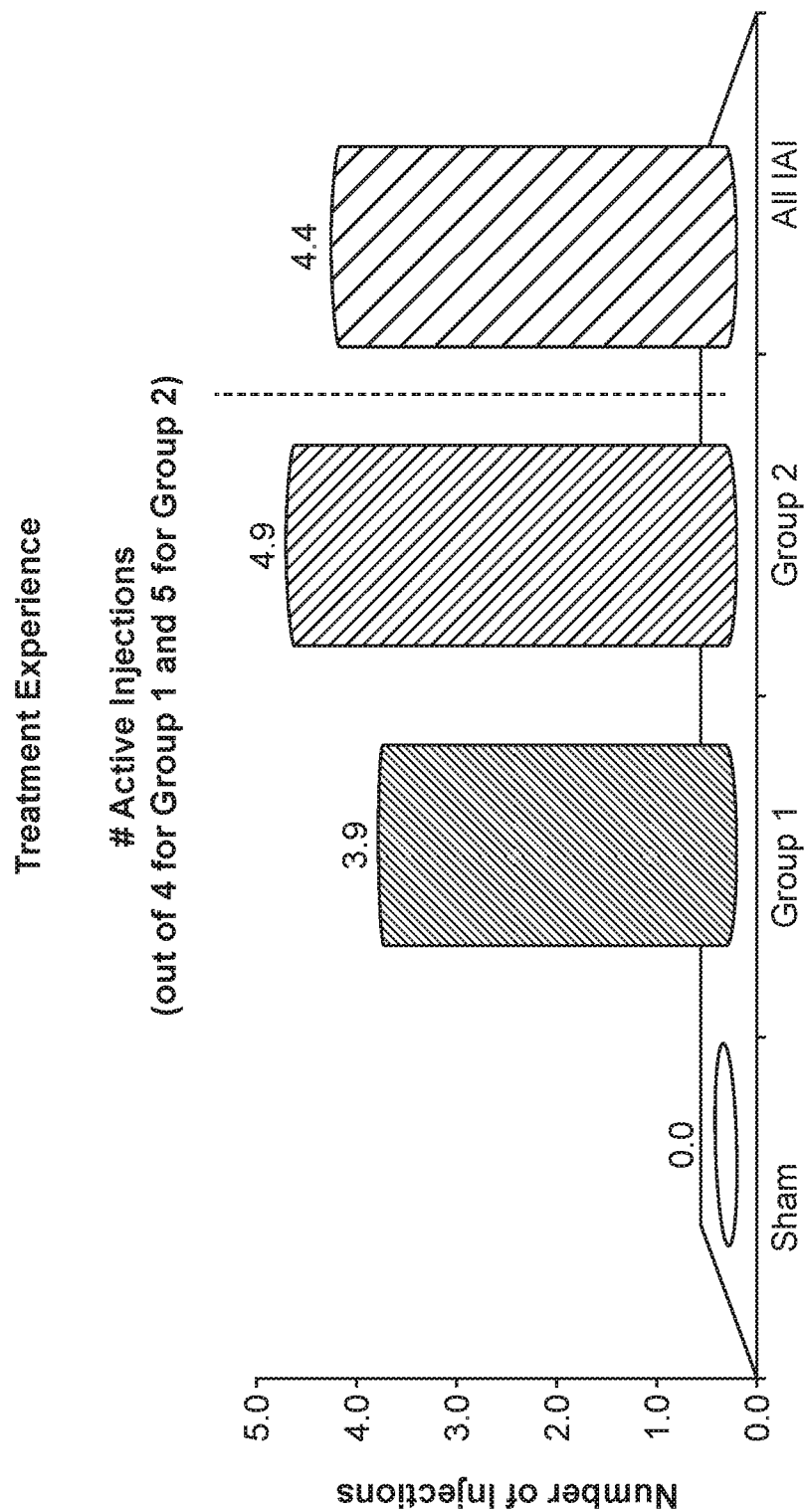
FIG. 7 sets forth the number of injections received by PANORAMA subjects in each dosing group (sham, Group 1, Group 2 and the combination of Group 1 and Group 2: "All IAI").
Figure 8:
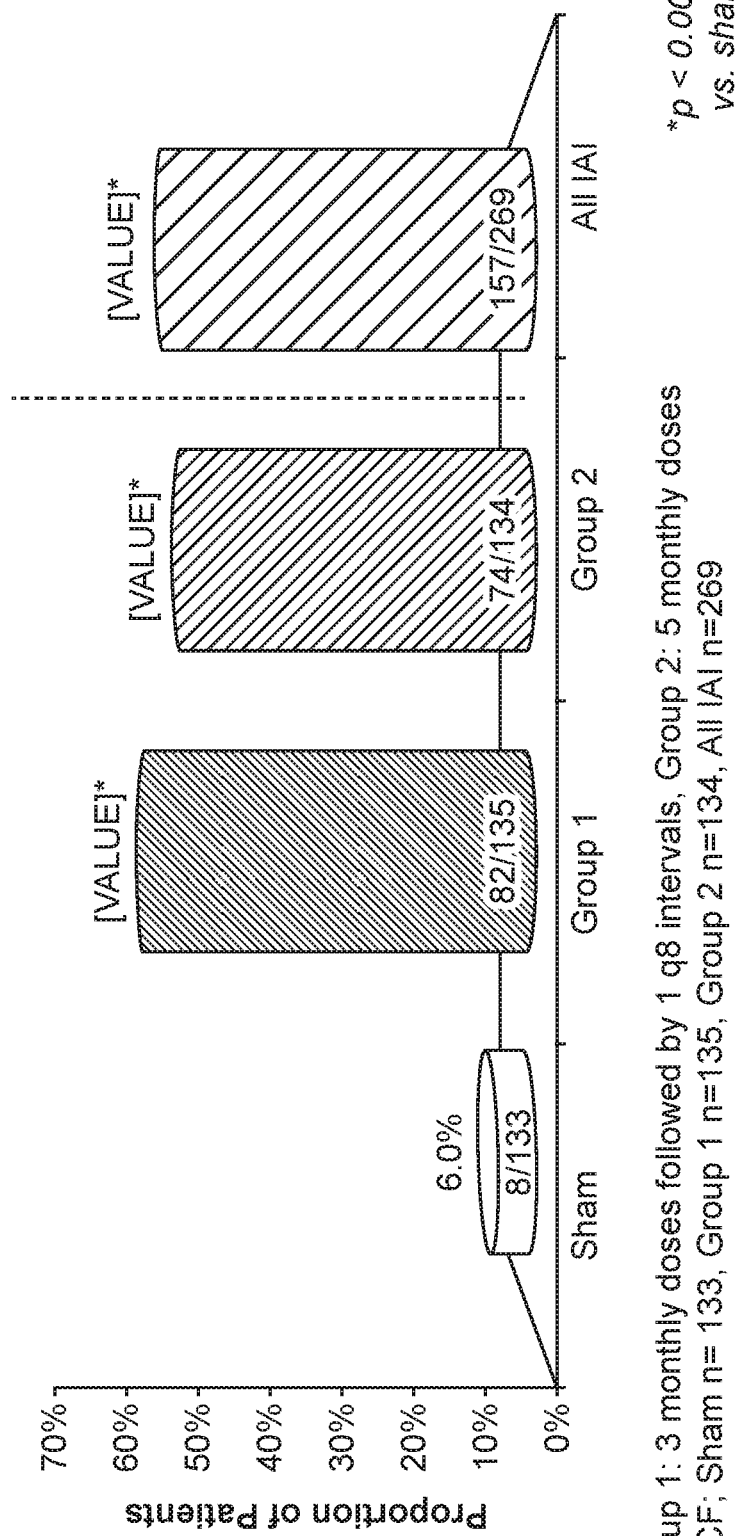
FIG. 8 shows the proportion (%) of PANORAMA patients in each dosing group (sham, Group 1, Group 2 and All IAI (combined Group 1 and Group 2)) achieving 2-step improvement from baseline on the diabetic retinopathy severity scale (DRSS).
Figure 20:
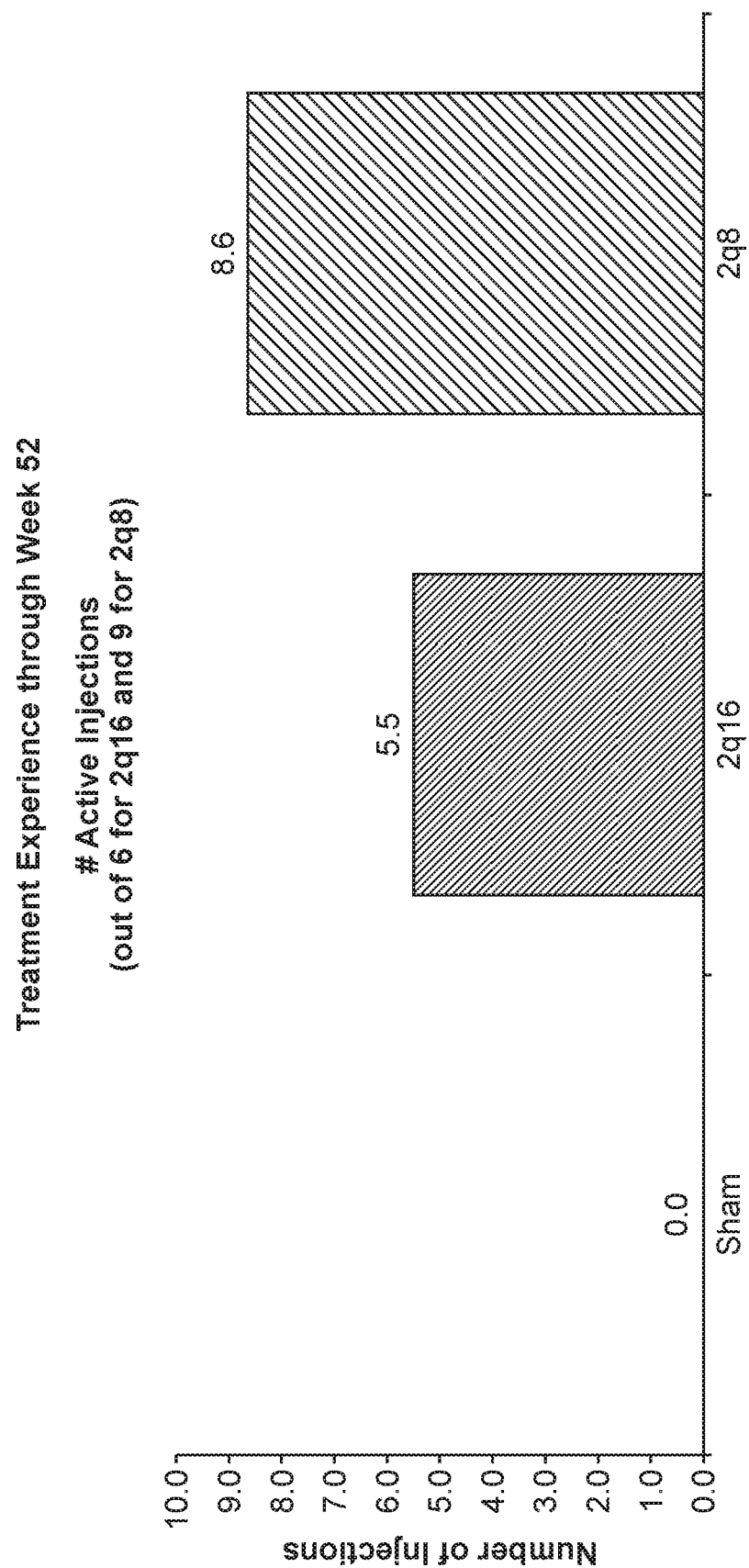
FIG. 20 summarizes the number of active injections given to subjects in treatment groups sham, 2q16 (out of 6) and 2q8 (out of 9) through week 52.
Figure 21:
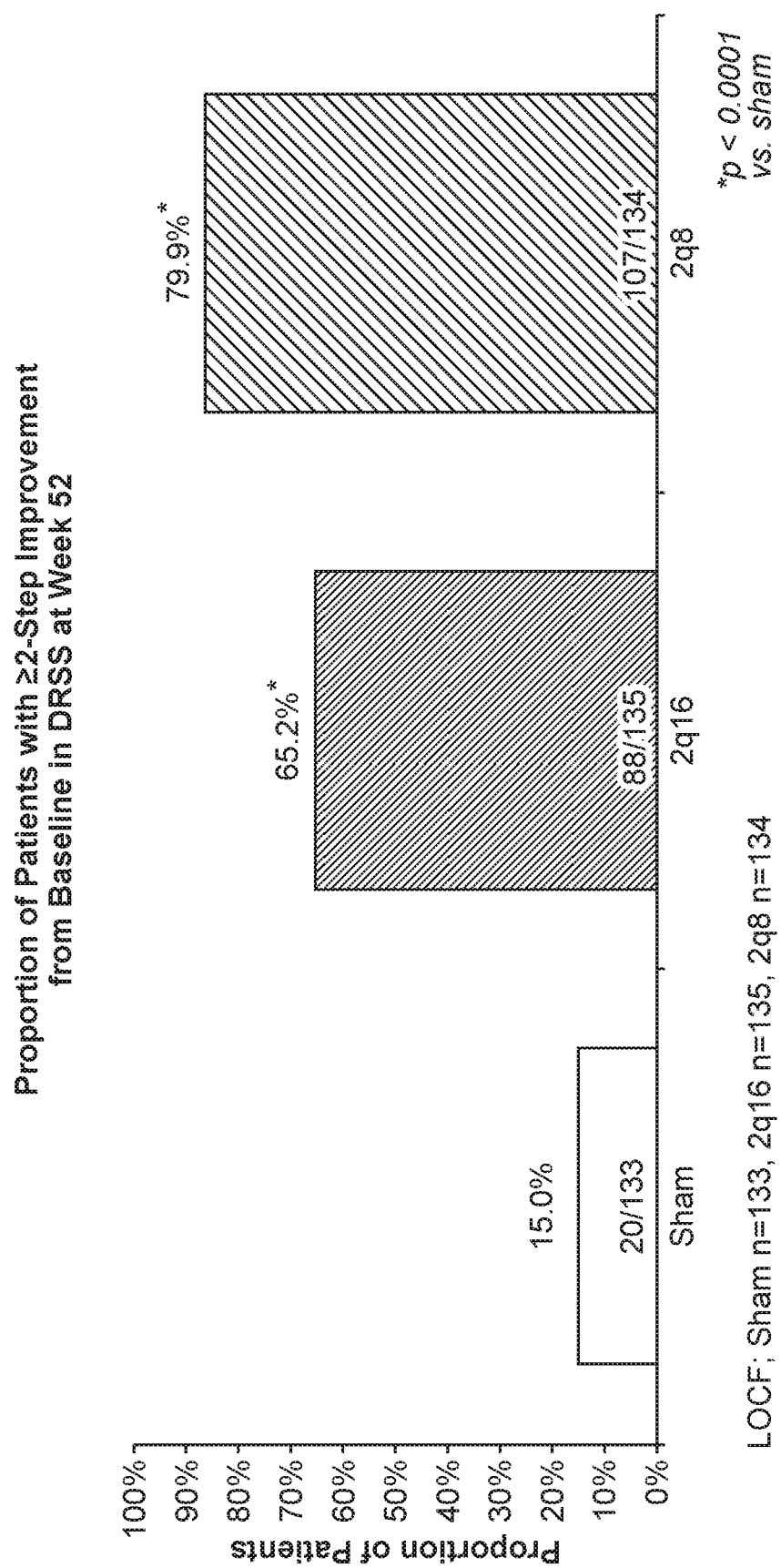
FIG. 21 summarizes the proportion of patients, in the sham, 2q16 and 2q8 groups, with at least a 2 step improvement, from baseline in DRSS at week 52. LOCF=last observation carried forward through week 52.
Figure 22:
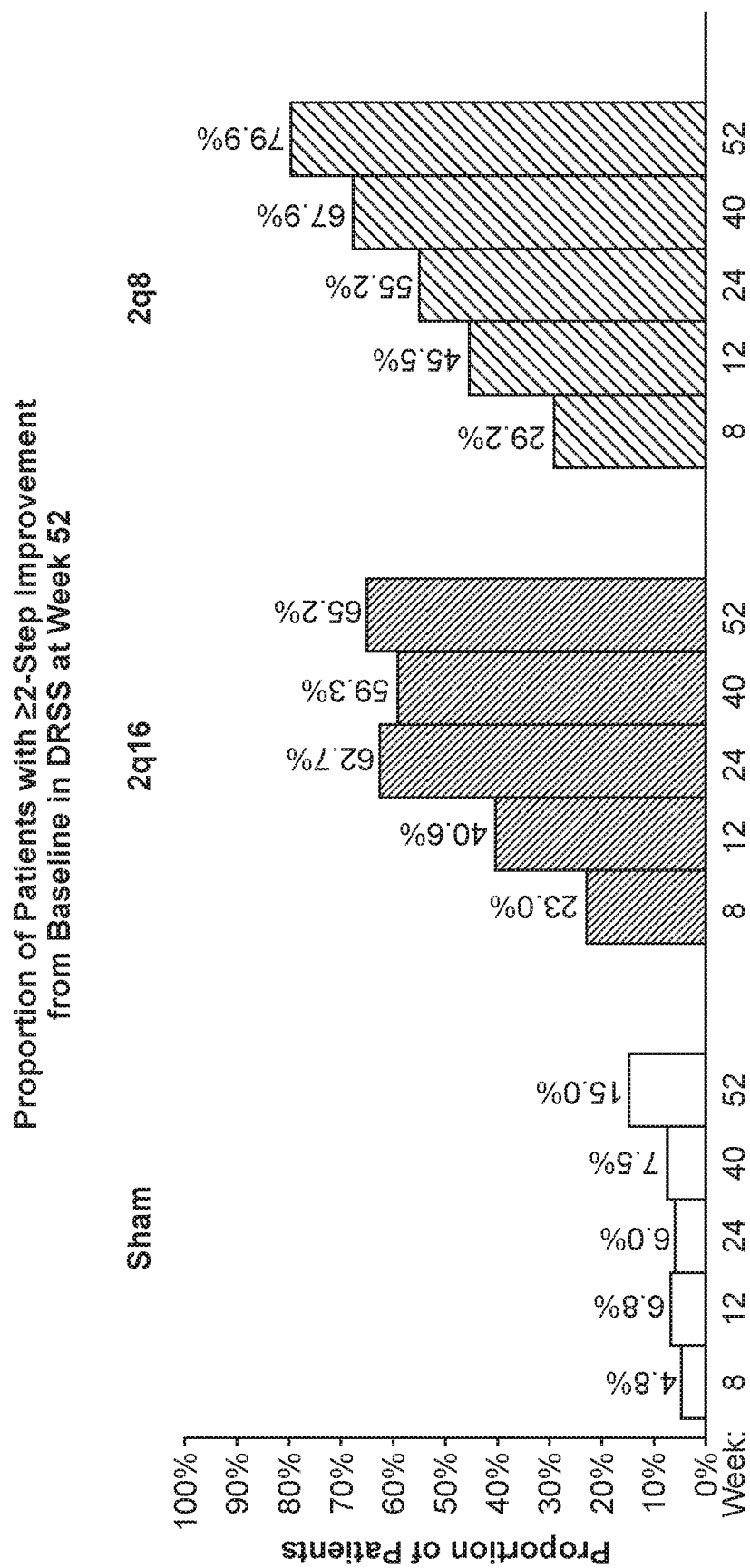
FIG. 22 summarizes the percentage of subjects in each treatment group (sham, 2q16 and 2q8) with at least a 2 step improvement, from baseline in DRSS at weeks 8, 12, 24, 40 and 52.

The number of injections received by each dose group after 24 weeks is shown in FIG. 7 and the number of injections after 52 weeks is shown in FIG. 20.

To preserve the masking, sham injections are performed for the 2Q8 and 2Q16 groups at treatment visits in which patients will not receive an active injection through week 96, and at all treatment visits for the sham group from baseline to week 96. Masking is maintained to the end of the study (week 100).

Rescue treatment in the study eye: Patients who develop PDR, ASNV, or center-involved DME (CI DME) in the study eye are treated, if deemed appropriate by the masked physician. For any of these complications, an FP (fundus photography) is performed before rescue treatment is given.

Patients who develop CI DME receive IVT aflibercept or laser photocoagulation, and no longer receive their randomized treatment. Rescue treatment is given by the masked or unmasked physician.

Patients who develop PDR and/or ASNV receive PRP or vitrectomy with endolaser, if necessary, but remain on their randomized treatment schedule. Panretinal photocoagulation or surgical intervention is performed by either the masked or unmasked physician. In addition, 1 injection of aflibercept is given, which must be administered by the unmasked physician.

If treatment for DME, ASNV, or PDR is given, patient data is censored from the time of treatment for the primary analysis.

Study Population 402 patients were enrolled. The patient population included men or women with type 1 or 2 diabetes mellitus who had moderately severe to severe NPDR (without DME threatening the center of the macula), in whom PRP can be safely deferred for at least 6 months. See FIG. 5 and FIG. 6. About 75% of patients had a DRSS of 47 and about 25% had a DRSS of 53.

For patients who meet eligibility criteria in both eyes, the eye with the most severe DRSS score is selected as the study eye. If both eyes have equivalent scores, factors such as ocular dominance and patient preference are considered in making the selection.

Ocular Procedures (Efficacy and Safety)

Best Corrected Visual Acuity (BCVA): Visual function of the study eye and the fellow eye is assessed using the ETDRS protocol (The Early Treatment Diabetic Retinopathy Study Group 1985) at 4 meters at each study visit. Visual acuity examiners are certified to ensure consistent measurement of BCVA. The VA examiner remains masked to treatment assignment. Best corrected visual acuity is done before any other ocular procedures are performed.

Intraocular Pressure (IOP): Intraocular pressure of the study eye is measured at every visit using Goldmann applanation tonometry or Tono Pen™. The same method of IOP measurement is used throughout the study for each individual patient. Intraocular pressure is measured pre-dose (bilateral) by the masked physician (or designee), and at approximately 30 minutes post-dose (study eye) by the unmasked physician (or designee).

Slit Lamp Examination: Patients' anterior eye structure and ocular adnexa is examined bilaterally pre-dose at each study visit using a slit lamp by the masked investigator.

Gonioscopy: Patients are evaluated for the development of neovascularization of the iridocorneal angle by gonioscopy in conjunction with slit lamp biomicroscopy. The examination is performed in the study eye only before the application of mydriatic agents or if frank rubeosis is present.

Indirect Ophthalmoscopy: Patients' posterior pole and peripheral retina are examined by indirect ophthalmoscopy at each study visit pre-dose (bilateral) by the masked investigator and post-dose (study eye) by the unmasked investigator. Post-dose evaluation is performed immediately after injection (active drug or sham).

Fundus Photography (FP)/Fluorescein Angiography (FA): The anatomical state of the retinal vasculature and the DRSS level is evaluated by FA and FP.

Spectral Domain Optical Coherence Tomography (SD-OCT): Retinal characteristics are evaluated at every visit using SD-OCT. Images are captured and transmitted for both eyes. Images are sent to an independent reading center where they are read by masked readers. All OCTs are electronically archived at the study sites as part of the source documentation. Optical coherence tomography technicians are certified by the reading center to ensure consistency and quality in image acquisition. Every effort is made to ensure that OCT technicians at the study site remain masked to treatment assignment.

Visual Field Testing: Visual field testing is assessed in the study eye using the Humphrey Visual Field Analyzer by sites who have access to this machine. Technicians are certified to ensure consistency and quality testing procedures. Every effort is made to ensure that visual field technicians at the study site remain masked to treatment assignment.

Adverse Events (AEs)

Overall safety was assessed by evaluation of treatment-emergent adverse events (TEAEs), physical examinations, electrocardiograms (ECGs), vital signs, and clinical safety laboratory tests (hematology, blood chemistry, hemoglobin A1c [HbA1c], and urinalysis) at various time points.

A TEAE is defined as an event (or an exacerbation of a preexisting event during the treatment period) that is observed or reported after the first administration of study drug, and no later than 30 days after last administration of study drug (active or sham injection).

The investigator (or designee) records all AEs that occur from the time the informed consent is signed until the end of study. All serious adverse events (SAEs), regardless of assessment of causal relationship to study drug must be reported within 24 hours.

Other events requiring reporting within 24 hours include symptomatic overdose of study drug (accidental or intentional overdose of at least 2 times the intended dose of study drug within the intended therapeutic window, if associated with an AE) and pregnancy.

The severity of AEs will be graded according to the following scale:

Mild: Does not interfere in a significant manner with the patient's normal functioning level. It may be an annoyance. Prescription drugs are not ordinarily needed for relief of symptoms, but may be given because of personality of the patient.

Moderate: Produces some impairment of functioning but is not hazardous to health. It is uncomfortable or an embarrassment. Treatment for symptom may be needed.

Severe: Produces significant impairment of functioning or incapacitation and is a definite hazard to the patient's health. Treatment for symptom may be given and/or patient hospitalized.

Results and Conclusions

Figure 9:
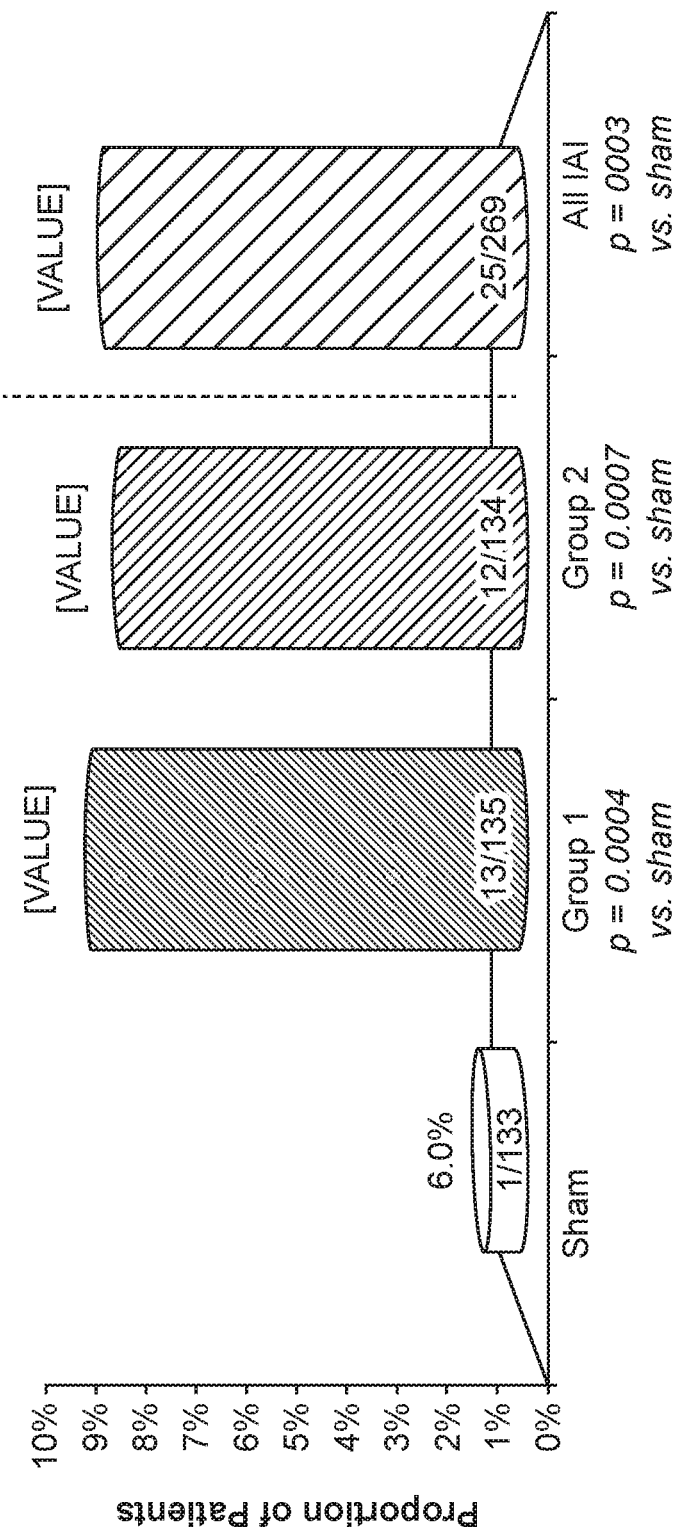
FIG. 9 shows the proportion (%) of PANORAMA patients in each dosing group (sham, Group 1, Group 2 and All IAI (combined Group 1 and Group 2)) achieving 3-step improvement from baseline on the diabetic retinopathy severity scale (DRSS).

The proportion of patients with 2-step improvement in the DRSS was significantly greater in the IAI groups vs sham. See FIGS. 8, 19, 21 and 22. Patients also achieved ≥3-step improvement in the IAI groups vs. Sham. See FIGS. 9 and 32.

Figure 10:
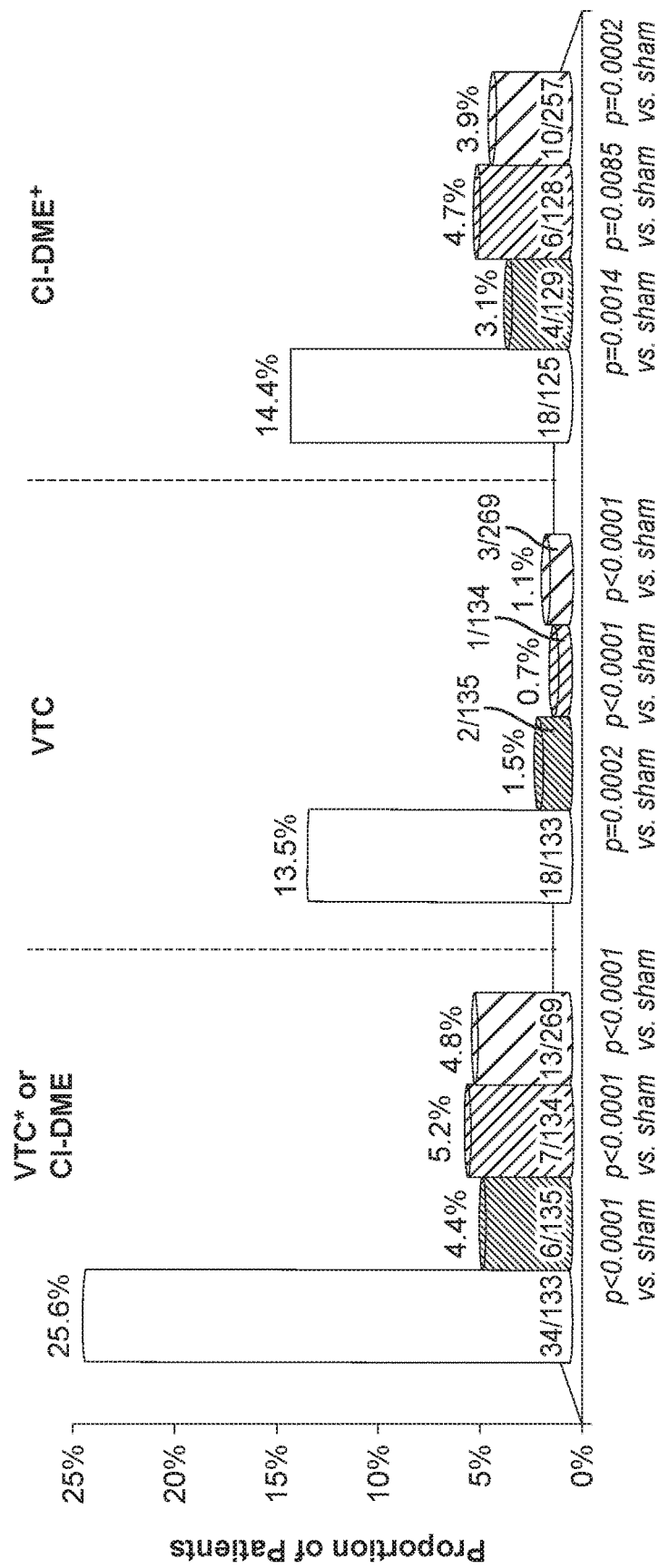
FIG. 10 shows the proportion (%) of PANORAMA patients in each dosing group (sham, Group 1, Group 2 and All IAI (combined Group 1 and Group 2)) experiencing vision threatening complications (VTC; proliferative diabetic retinopathy (PDR)/anterior segment neovascularization (ASNV))) and/or center involved diabetic macular edema (CI-DME) through week 24.
Figure 23:
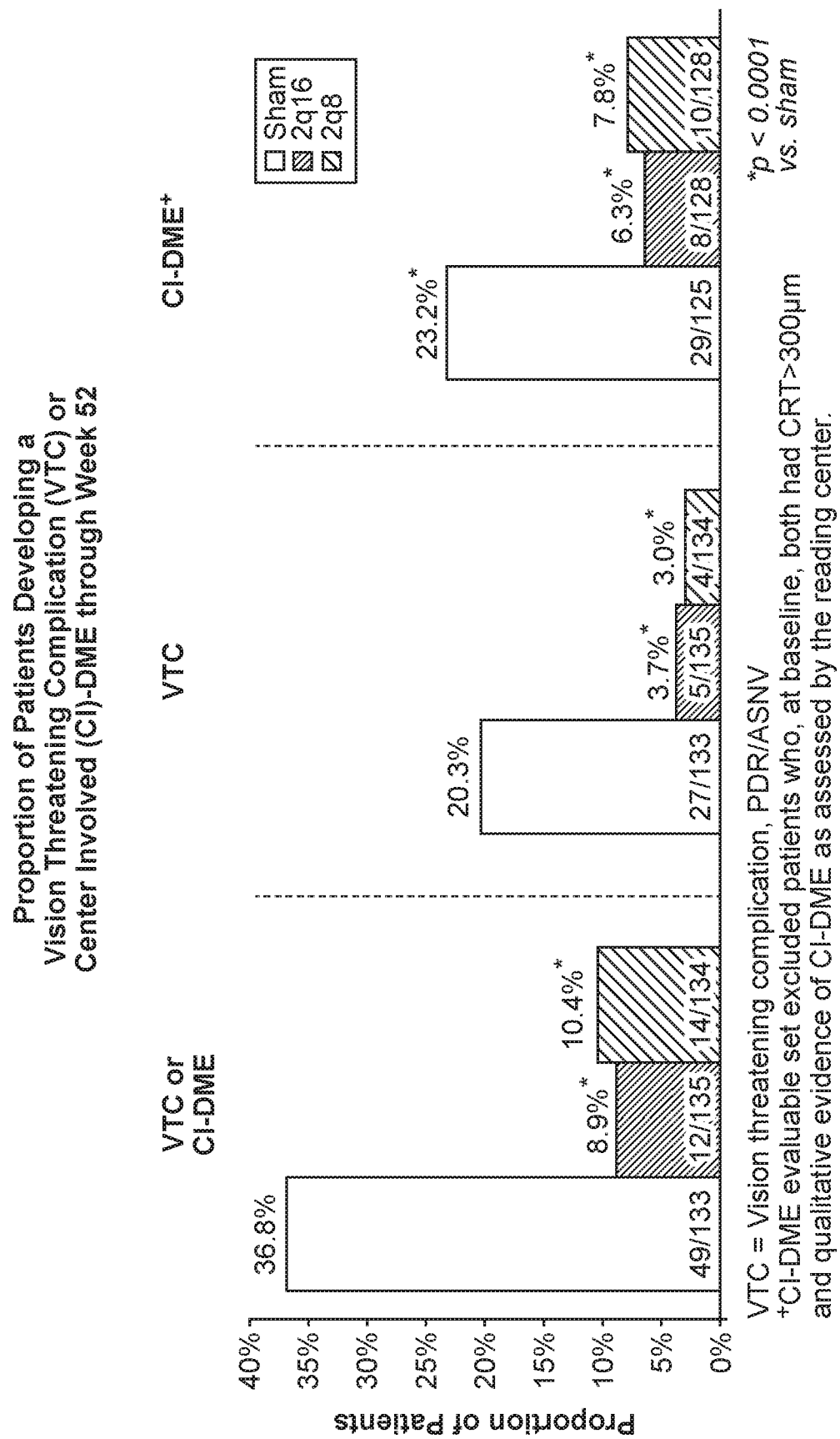
FIG. 23 summarizes the percentage of patients in each treatment group (sham, 2q16 and 2q8) developing a vision threatening complication (VTC) and/or center-involved diabetic macular edema (CI-DME) through week 52.
Figure 24:
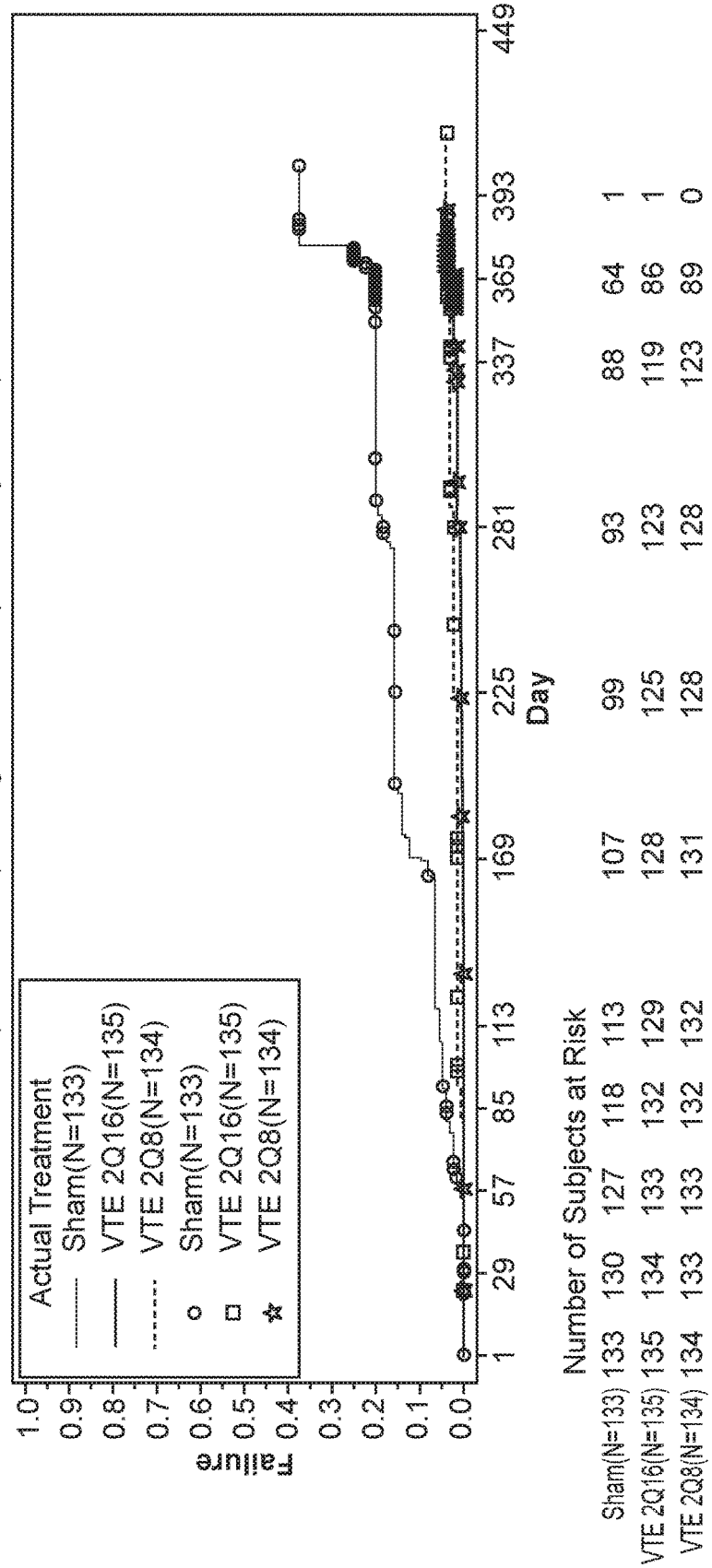
FIG. 24 is a Kaplan-Meier plot of the probability of developing a vision threatening complication over time for subjects in each treatment group (sham, 2q16 and 2q8). VTE=VEGF Trap eye. VTC=vision threatening complication.
Figure 25:
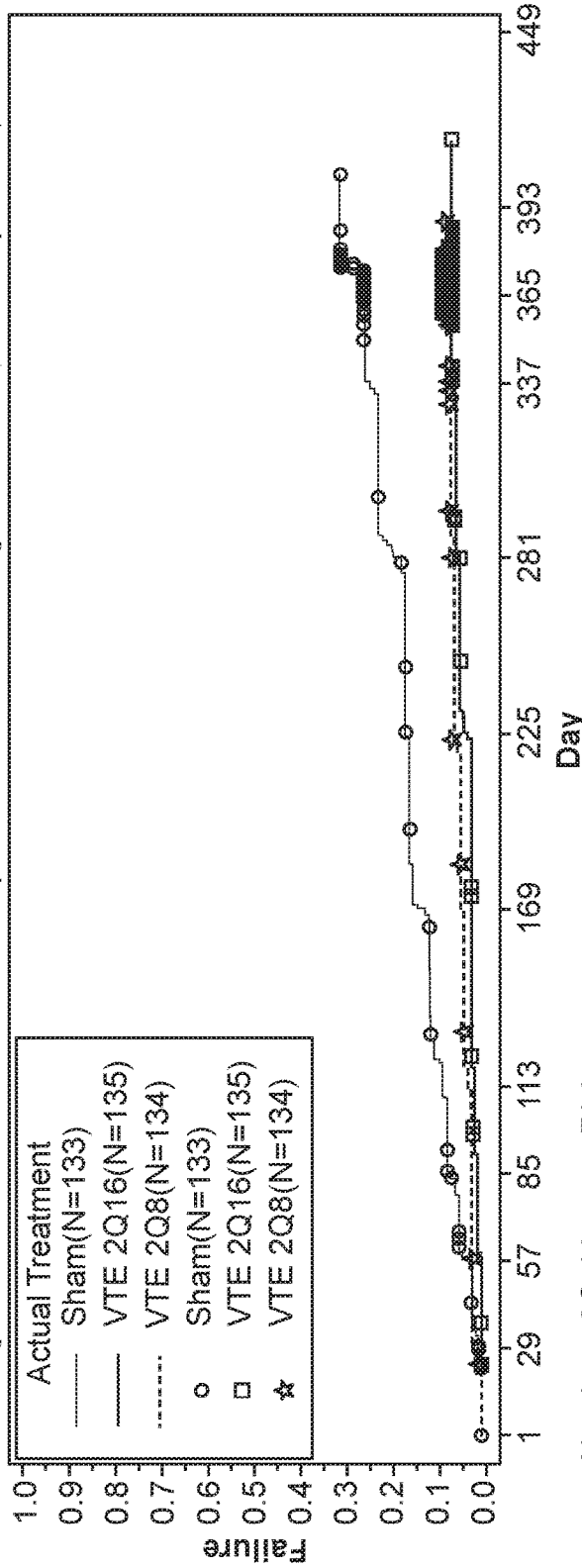
FIG. 25 summarizes the time for subjects in each treatment group (sham, 2q16 and 2q8) to develop CI-DME.

IAI reduced the number of patients who developed a VTC and CI-DME. At 24 and 52 weeks, the proportion of patients experiencing a VTC and/or DME is summarized in FIGS. 10 and 23. A Kaplan-Meier analysis of the probability of developing a VTC or CI-DME in patients in each treatment group over time is set forth in FIGS. 24 and 25. A vision threatening complication (VTC) is progression to proliferative diabetic retinopathy (PDR) and anterior segment neovascularization (ASNV).

Figure 11:
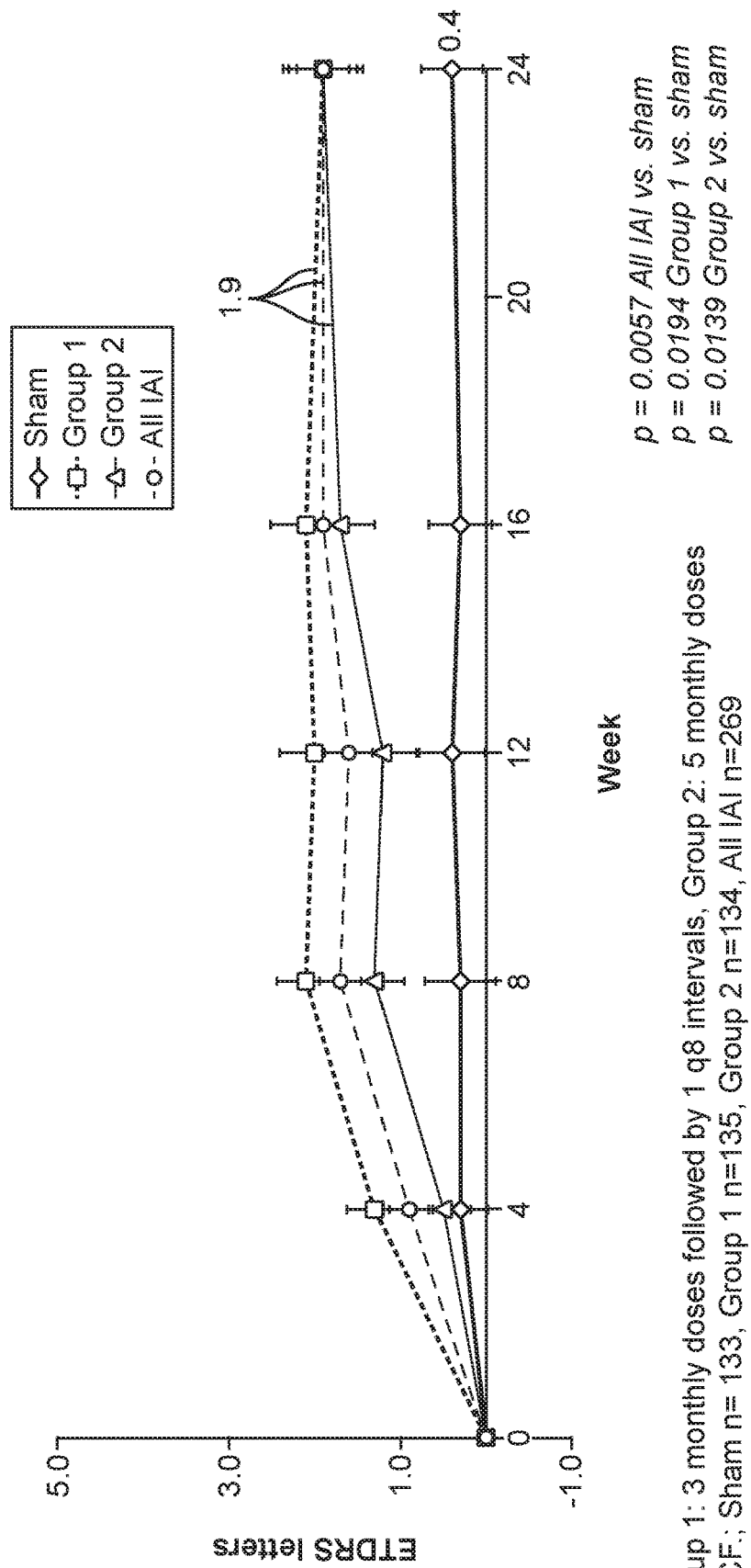
FIG. 11 summarizes the mean change in best corrected visual acuity (BCVA) score (early treatment diabetic retinopathy study (ETDRS) letters) of each PANORAMA dosing group (sham, Group 1, Group 2 and the combination of Group 1 and Group 2: "All IAI") up to 24 weeks.
Figure 12:
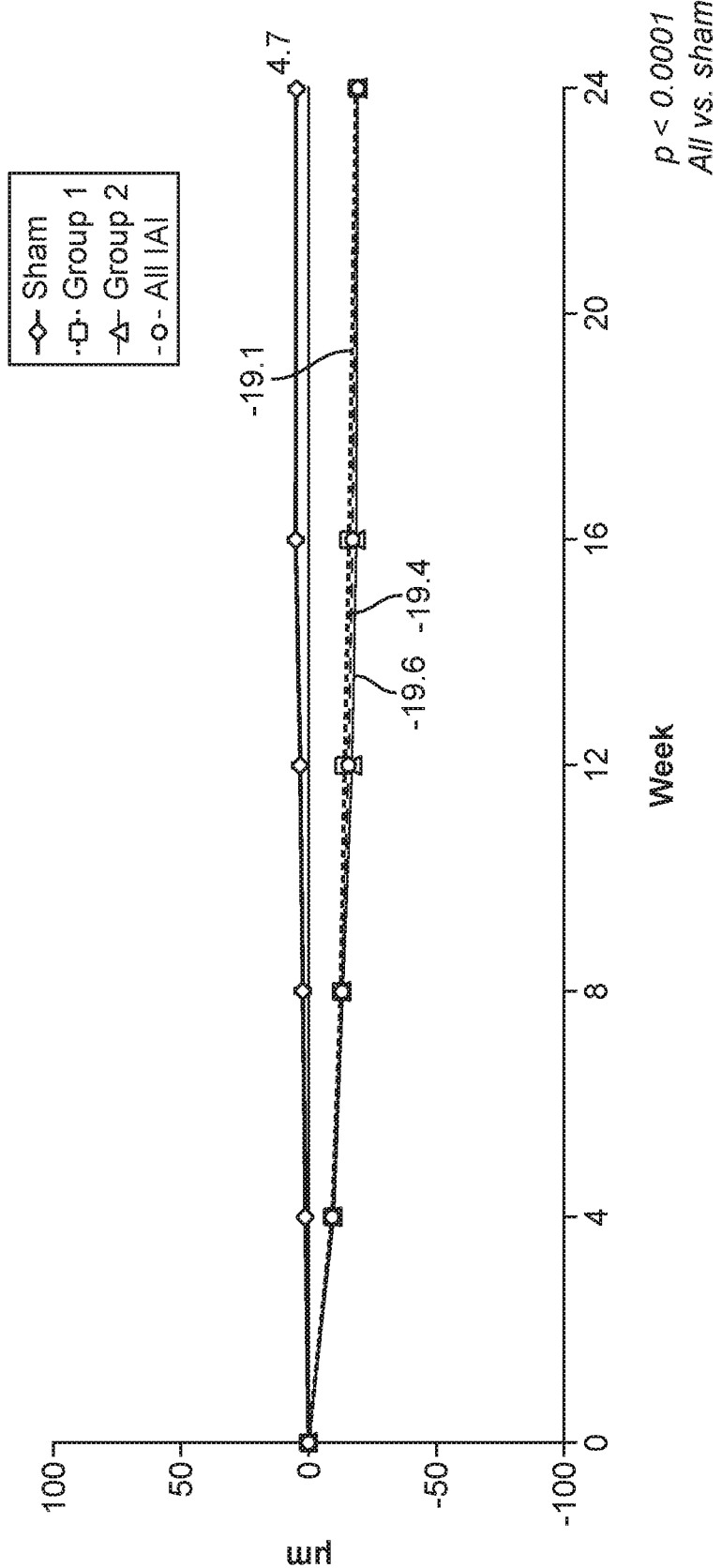
FIG. 12 summarizes the mean change in central retinal thickness (CRT, μm) of each PANORAMA dosing group (sham, Group 1, Group 2 and All IAI (combined Group 1 and Group 2)) through Week 24.
Figure 19:
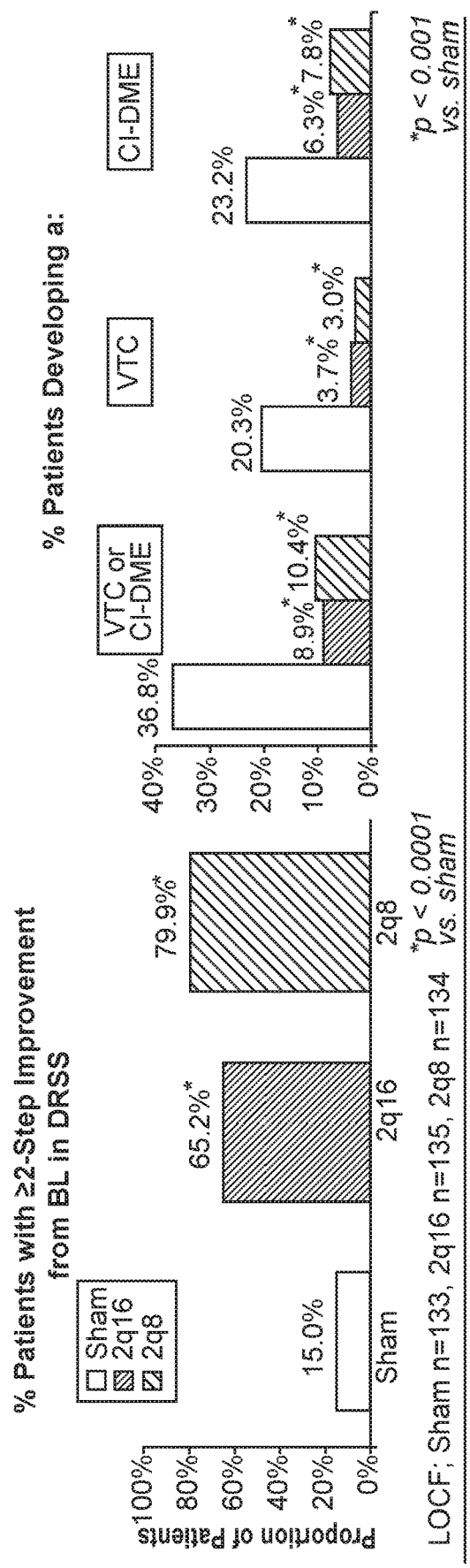
FIG. 19 is a summary of the results of the PANORAMA trial after 52 weeks-percentage of patients in each treatment group experiencing at least a 2 step improvement in DRSS and the percentage of subjects developing a vision threatening complication (VTC) and/or center-involved diabetic macular edema (CI-DME).
Figure 26:
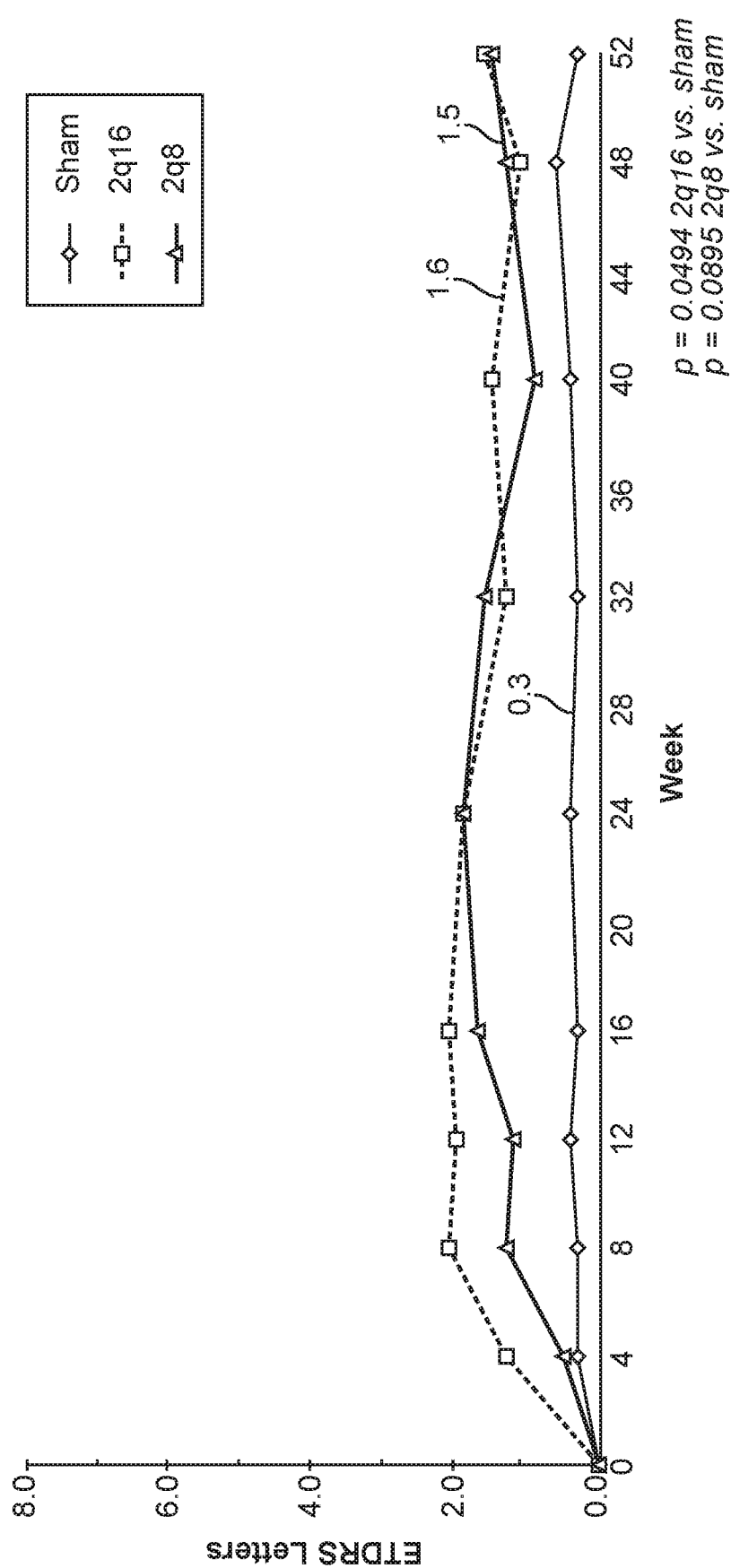
FIG. 26 summarizes the mean change in best corrected visual acuity (ETDRS letters) for subjects in each treatment group (sham, 2q16 and 2q8) over 52 weeks.
Figure 27:
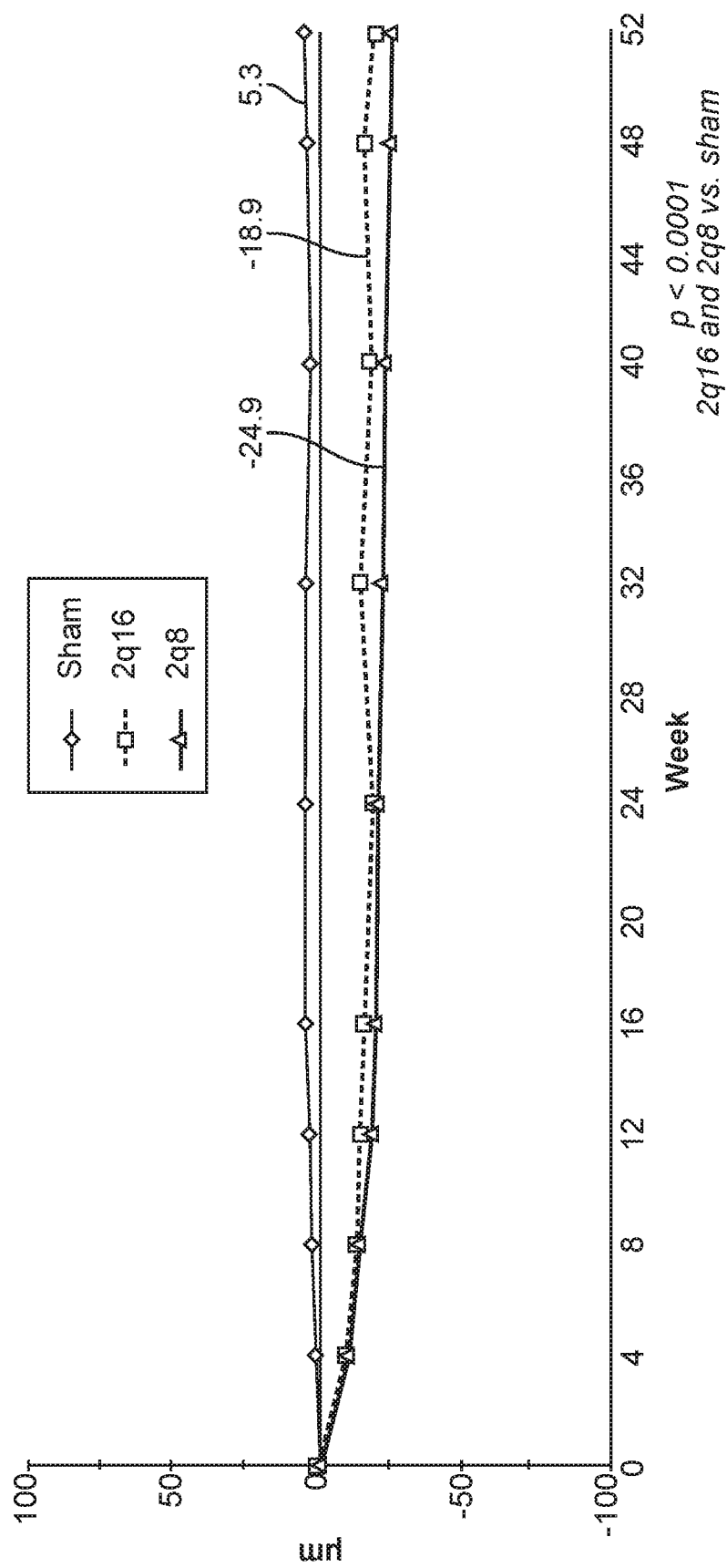
FIG. 27 summarizes the central retinal thickness (μm) for subjects in each treatment group (sham, 2q16 and 2q8) over 52 weeks.

The changes in best corrected visual acuity (BCVA) experienced by patients in each treatment group at 24 and 52 weeks are summarized FIGS. 11 and 26. The changes to central retinal thickness of each treatment group is summarized in FIGS. 12 and 27.

Efficacy outcomes were similar in the 2Q16 (Group 1) and the 2Q8 (Group 2) groups.

Ocular treatment emergent adverse events at 24 and 52 weeks (TEAEs) (FIGS. 13 and 28, respectively), ocular serious TEAEs at 24 and 52 weeks (FIGS. 14 and 29, respectively), intra-ocular inflammation at 24 and 52 weeks (FIGS. 15 and 30, respectively), and Anti-Platelet Trialists' Collaboration (APTC) events at 24 and 52 weeks (FIGS. 16 and 31, respectively) and deaths at 24 weeks (FIG. 17) are provided. At 52 weeks, there was a total of 7 deaths (7 in the sham treatment group and 1 in the q8w treatment group). (APTC: See Antithrombotic Trialists' Collaboration. Collaborative overview of randomized trial of antiplatelet therapy—II: Maintenance of vascular graft or arterial patency by antiplatelet therapy. Br Med J 1994; 308:168-171; and Antithrombotic Trialists' Collaboration. Collaborative meta-analysis of randomised trials of antiplatelet therapy for prevention of death, myocardial infarction, and stroke in high risk patients. Br Med J 2002; 324:71-86).

SEQUENCES

SEQ ID NO: 1 (DNA sequence having 1377 nucleotides):
ATGGTCAGCTACTGGGACACCGGGGTCCTGCTGTGCGCGCTGCTCAGCTG
TCTGCTTCTCACAGGATCTAGTTCCGGAAGTGATACCGGTAGACCTTTCG
TAGAGATGTACAGTGAAATCCCCGAAATTATACACATGACTGAAGGAAGG
GAGCTCGTCATTCCCTGCCGGGTTACGTCACCTAACATCACTGTTACTTT
AAAAAAGTTTCCACTTGACACTTTGATCCCTGATGGAAAACGCATAATCT
GGGACAGTAGAAAGGGCTTCATCATATCAAATGCAACGTACAAAGAAATA
GGGCTTCTGACCTGTGAAGCAACAGTCAATGGGCATTTGTATAAGACAAA
CTATCTCACACATCGACAAACCAATACAATCATAGATGTGGTTCTGAGTC
CGTCTCATGGAATTGAACTATCTGTTGGAGAAAAGCTTGTCTTAAATTGT
ACAGCAAGAACTGAACTAAATGTGGGGATTGACTTCAACTGGGAATACCC
TTCTTCGAAGCATCAGCATAAGAAACTTGTAAACCGAGACCTAAAAACCC
AGTCTGGGAGTGAGATGAAGAAATTTTTGAGCACCTTAACTATAGATGGT
GTAACCCGGAGTGACCAAGGATTGTACACCTGTGCAGCATCCAGTGGGCT
GATGACCAAGAAGAACAGCACATTTGTCAGGGTCCATGAAAAGGACAAAA
CTCACACATGCCCACCGTGCCCAGCACCTGAACTCCTGGGGGGACCGTCA
GTCTTCCTCTTCCCCCCAAAACCCAAGGACACCCTCATGATCTCCCGGAC
CCCTGAGGTCACATGCGTGGTGGTGGACGTGAGCCACGAAGACCCTGAGG
TCAAGTTCAACTGGTACGTGGACGGCGTGGAGGTGCATAATGCCAAGACA
AAGCCGCGGGAGGAGCAGTACAACAGCACGTACCGTGTGGTCAGCGTCCT
CACCGTCCTGCACCAGGACTGGCTGAATGGCAAGGAGTACAAGTGCAAGG
TCTCCAACAAAGCCCTCCCAGCCCCCATCGAGAAAACCATCTCCAAAGCC
AAAGGGCAGCCCCGAGAACCACAGGTGTACACCCTGCCCCCATCCCGGGA
TGAGCTGACCAAGAACCAGGTCAGCCTGACCTGCCTGGTCAAAGGCTTCT
ATCCCAGCGACATCGCCGTGGAGTGGGAGAGCAATGGGCAGCCGGAGAAC
AACTACAAGACCACGCCTCCCGTGCTGGACTCCGACGGCTCCTTCTTCCT
CTACAGCAAGCTCACCGTGGACAAGAGCAGGTGGCAGCAGGGGAACGTCT
TCTCATGCTCCGTGATGCATGAGGCTCTGCACAACCACTACACGCAGAAG
AGCCTCTCCCTGTCTCCGGGTAAATGA SEQ ID NO: 2 (polypeptide sequence having 458 amino acids):
MVSYWDTGVLLCALLSCLLLTGSSSGSDTGRPFVEMYSEIPEIIHMTEGR
ELVIPCRVTSPNITVTLKKFPLDTLIPDGKRIIWDSRKGFIISNATYKEI
GLLICEATVNGHLYKTNYLTHRQINTIIDVVLSPSHGIELSVGEKLVLNC
TARTELNVGIDFNWEYPSSKHQHKKLVNRDLKTQSGSEMKKFLSTLTIDG
VTRSDQGLYTCAASSGLMTKKNSTFVRVHEKDKTHTCPPCPAPELLGGPS
VFLFPPKPKDTLMISRTPEVTCVVVDVSHEDPEVKFNWYVDGVEVHNAKT
KPREEQYNSTYRVVSVLTVLHQDWLNGKEYKCKVSNKALPAPIEKTISKA -continued

SEQUENCES

KGQPREPQVYTLPPSRDELTKNQVSLTCLVKGFYPSDIAVEWESNGQPEN
NYKTTPPVLDSDGSFFLYSKLTVDKSRWQQGNVFSCSVMHEALHNHYTQK
SLSLSPGK

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

What is claimed is:

1. A method for treating diabetic retinopathy in a patient in need of such treatment, said method comprising administering, to an eye of the patient,
   (i) an initial dose;
   (ii) a 2nd dose one month after the initial dose;
   (iii) a 3rd dose one month after 2nd dose;
   (iv) a 4th dose 8 weeks after the 3rd dose; and then
   (v) one or more doses every 16 weeks starting after the 4th dose;
   of about 2 mg of VEGF antagonist that is a VEGF receptor-based chimeric molecule.

2. The method of claim 1 wherein the patient is administered the VEGF antagonist by intravitreal injection.

3. The method of claim 2 wherein the VEGF antagonist comprises
   (1) a VEGFR1 component comprising amino acids 27 to 129 of SEQ ID NO:2;
   (2) a VEGFR2 component comprising amino acids 130-231 of SEQ ID NO:2; and
   (3) a multimerization component comprising amino acids 232-457 of SEQ ID NO:2.

4. The method of claim 2, wherein the VEGF antagonist is aflibercept.

5. The method of claim 2, wherein the VEGF antagonist comprises
   (1) an immunoglobin-like (Ig) domain 2 of VEGFR1;
   (2) Ig domain 3 of VEGFR2, and
   (3) a multimerizing component.

6. The method of claim 2, wherein the VEGF antagonist is conbercept.

7. The method of claim 4 wherein the patient suffers from nonproliferative diabetic retinopathy.

8. The method of claim 4 wherein the patient suffers from moderately severe or severe nonproliferative diabetic retinopathy.

9. The method of claim 4 wherein the patient suffers from nonproliferative diabetic retinopathy which is characterized by a Diabetic Retinopathy Severity Scale level of 47 or 53.

10. The method of claim 4 wherein the patient does not suffer from diabetic macular edema or center involved diabetic macular edema.

11. The method of claim 4 wherein the patient has a baseline best-corrected visual acuity (BCVA) ETDRS letter score of 69 or greater.

12. The method of claim 4 wherein the vision of the patient is characterized by a Snellen visual acuity of 20/40 or better.

13. The method of claim 4, wherein the patient is human.

14. The method of claim 4, wherein the patient is a human 18 years of age or older.

15. The method of claim 4 wherein the patient does not suffer from:
   retinal neovascularization;
   anterior segment neovascularization (ASNV);
   vitreous hemorrhage; and/or
   tractional retinal detachment.

16. The method of claim 4 wherein the patient suffers from proliferative diabetic retinopathy.

17. The method of claim 4 wherein the aflibercept is in a pharmaceutical formulation comprising 40 mg/mL aflibercept, in 10 mM sodium phosphate, 40 mM sodium chloride, 0.03% polysorbate 20, and 5% sucrose, pH 6.2.

18. The method of claim 17 wherein about 50 microliters of the pharmaceutical formulation is administered.

19. The method of claim 18 wherein the pharmaceutical formulation is administered by intravitreal injection with a syringe having a 30-gauge, ½-inch injection needle.

20. The method of claim 4 wherein the aflibercept is in a pharmaceutical formulation comprising 40 mg/mL aflibercept, histidine buffer, a sugar and a surfactant.

21. The method of claim 6 wherein the conbercept is in a pharmaceutical formulation comprising citric acid, sucrose, arginine and polysorbate 20.

\* \* \* \* \*

SEQUENCE LISTING

<160> NUMBER OF SEQ ID NOS: 2

<210> SEQ ID NO 1
<211> LENGTH: 1377
<212> TYPE: DNA
<213> ORGANISM: Artificial Sequence
<220> FEATURE:
<223> OTHER INFORMATION: Synthetic

<400> SEQUENCE: 1

| | | | | | |
|---|---|---|---|---|---|
| atggtcagct | actgggacac | cggggtcctg | ctgtgcgcgc | tgctcagctg | tctgcttctc | 60 |
| acaggatcta | gttccggaag | tgataccggt | agacctttcg | tagagatgta | cagtgaaatc | 120 |
| cccgaaatta | tacacatgac | tgaaggaagg | gagctcgtca | ttccctgccg | ggttacgtca | 180 |
| cctaacatca | ctgttacttt | aaaaaagttt | ccacttgaca | ctttgatccc | tgatggaaaa | 240 |
| cgcataatct | gggacagtag | aaagggcttc | atcatatcaa | atgcaacgta | caaagaaata | 300 |
| gggcttctga | cctgtgaagc | aacagtcaat | gggcatttgt | ataagacaaa | ctatctcaca | 360 |
| catcgacaaa | ccaatacaat | catagatgtg | gttctgagtc | cgtctcatgg | aattgaacta | 420 |
| tctgttggag | aaaagcttgt | cttaaattgt | acagcaagaa | ctgaactaaa | tgtggggatt | 480 |
| gacttcaact | gggaataccc | ttcttcgaag | catcagcata | agaaacttgt | aaaccgagac | 540 |
| ctaaaaaccc | agtctgggag | tgagatgaag | aaattttga | gcaccttaac | tatagatggt | 600 |
| gtaacccgga | gtgaccaagg | attgtacacc | tgtgcagcat | ccagtgggct | gatgaccaag | 660 |
| aagaacagca | catttgtcag | ggtccatgaa | aaggacaaaa | ctcacacatg | cccaccgtgc | 720 |
| ccagcacctg | aactcctggg | gggaccgtca | gtcttcctct | tccccccaaa | acccaaggac | 780 |
| accctcatga | tctcccggac | ccctgaggtc | acatgcgtgg | tggtggacgt | gagccacgaa | 840 |
| gaccctgagg | tcaagttcaa | ctggtacgtg | gacggcgtgg | aggtgcataa | tgccaagaca | 900 |
| aagccgcggg | aggagcagta | caacagcacg | taccgtgtgg | tcagcgtcct | caccgtcctg | 960 |
| caccaggact | ggctgaatgg | caaggagtac | aagtgcaagg | tctccaacaa | agccctccca | 1020 |
| gcccccatcg | agaaaaccat | ctccaaagcc | aaagggcagc | cccgagaacc | acaggtgtac | 1080 |
| accctgcccc | catcccggga | tgagctgacc | aagaaccagg | tcagcctgac | ctgcctggtc | 1140 |
| aaaggcttct | atcccagcga | catcgccgtg | gagtgggaga | gcaatgggca | gccggagaac | 1200 |
| aactacaaga | ccacgcctcc | cgtgctggac | tccgacggct | ccttcttcct | ctacagcaag | 1260 |
| ctcaccgtgg | acaagagcag | gtggcagcag | gggaacgtct | tctcatgctc | cgtgatgcat | 1320 |
| gaggctctgc | acaaccacta | cacgcagaag | agcctctccc | tgtctccggg | taaatga | 1377 |

<210> SEQ ID NO 2
<211> LENGTH: 458
<212> TYPE: PRT
<213> ORGANISM: Artificial Sequence
<220> FEATURE:
<223> OTHER INFORMATION: Synthetic

<400> SEQUENCE: 2

```
Met Val Ser Tyr Trp Asp Thr Gly Val Leu Leu Cys Ala Leu Leu Ser
 1               5                  10                  15

Cys Leu Leu Leu Thr Gly Ser Ser Gly Ser Asp Thr Gly Arg Pro
            20                  25                  30

Phe Val Glu Met Tyr Ser Glu Ile Pro Glu Ile Ile His Met Thr Glu
                35                  40                  45

Gly Arg Glu Leu Val Ile Pro Cys Arg Val Thr Ser Pro Asn Ile Thr
 50                  55                  60

Val Thr Leu Lys Lys Phe Pro Leu Asp Thr Leu Ile Pro Asp Gly Lys
 65                  70                  75                  80

Arg Ile Ile Trp Asp Ser Arg Lys Gly Phe Ile Ile Ser Asn Ala Thr
                85                  90                  95

Tyr Lys Glu Ile Gly Leu Leu Thr Cys Glu Ala Thr Val Asn Gly His
                100                 105                 110

Leu Tyr Lys Thr Asn Tyr Leu Thr His Arg Gln Thr Asn Thr Ile Ile
            115                 120                 125

Asp Val Val Leu Ser Pro Ser His Gly Ile Glu Leu Ser Val Gly Glu
 130                 135                 140

Lys Leu Val Leu Asn Cys Thr Ala Arg Thr Glu Leu Asn Val Gly Ile
145                 150                 155                 160

Asp Phe Asn Trp Glu Tyr Pro Ser Ser Lys His Gln His Lys Lys Leu
                165                 170                 175

Val Asn Arg Asp Leu Lys Thr Gln Ser Gly Ser Glu Met Lys Lys Phe
            180                 185                 190

Leu Ser Thr Leu Thr Ile Asp Gly Val Thr Arg Ser Asp Gln Gly Leu
            195                 200                 205

Tyr Thr Cys Ala Ala Ser Ser Gly Leu Met Thr Lys Lys Asn Ser Thr
 210                 215                 220

Phe Val Arg Val His Glu Lys Asp Lys Thr His Thr Cys Pro Pro Cys
225                 230                 235                 240

Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
            275                 280                 285

Tyr Val Asp Gly Val Glu Val His Asn Ala Lys Thr Lys Pro Arg Glu
            290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
                340                 345                 350

Gln Pro Arg Glu Pro Gln Val Tyr Thr Leu Pro Pro Ser Arg Asp Glu
            355                 360                 365

Leu Thr Lys Asn Gln Val Ser Leu Thr Cys Leu Val Lys Gly Phe Tyr
            370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415
```

```
Leu Tyr Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
            435                 440                 445

Gln Lys Ser Leu Ser Leu Ser Pro Gly Lys
    450                 455
```